US005744489A

United States Patent [19]

Greenwood

[11] Patent Number: 5,744,489
[45] Date of Patent: Apr. 28, 1998

[54] METHOD OF TREATING GASTROINTESTINAL MOTILITY DISORDERS

[76] Inventor: Beverley Greenwood, 6593 Manchester Dr., Fishers, Ind. 46308

[21] Appl. No.: 350,871

[22] Filed: May 30, 1995

Related U.S. Application Data

[63] Continuation of Ser. No. 171,060, Dec. 21, 1993, abandoned.

[51] Int. Cl.⁶ .......................... A61K 31/44; A61K 31/41
[52] U.S. Cl. ............................................ 514/340; 514/342
[58] Field of Search ...................................... 514/342, 340

[56] References Cited

FOREIGN PATENT DOCUMENTS

| | | |
|---|---|---|
| 0 307 142 A1 | 9/1988 | European Pat. Off. . |
| 0 384 288 A2 | 2/1990 | European Pat. Off. . |
| WO 92/03430 | 3/1992 | WIPO . |
| WO 92/03431 | 3/1992 | WIPO . |
| WO 94/20495 | 9/1994 | WIPO . |

OTHER PUBLICATIONS

Sauerberg et al., J. Med. Chem., vol. 35, pp. 2274–2283, 1992.

Abstract 94223546 Medline (1994).

*Primary Examiner*—Phyllis G. Spivack
*Attorney, Agent, or Firm*—Steve T. Zelson; Elias J. Lambiris

[57] ABSTRACT

The present invention relates to a method for treating a mammal suffering from gastrointestinal motility disorders comprising administering certain thiadiazole and oxadiazole compounds that are herein disclosed.

17 Claims, No Drawings

METHOD OF TREATING GASTROINTESTINAL MOTILITY DISORDERS

CROSS-REFERENCE TO RELATED APPLICATION

The instant application is a continuation of Ser. No. 08/171,060 filed Dec. 21, 1993, abandoned which is incorporated herein by reference.

BACKGROUND OF THE INVENTION

This invention provides a novel method for treating a mammal suffering from gastrointestinal motility disorders.

The primary function of the gastrointestinal tract is the absorption of ingested nutrients. To achieve this primary function requires that transit along the esophagus and gastrointestinal tract is at a rate that allows for optimal digestion and absorption of water and electrolytes. Although the etiology and pathophysiology of esophageal and gastrointestinal motility disorders is incompletely understood, abnormal patterns of gastrointestinal motility that result in stimulated motility (hypermotility) may cause many of the symptoms of disorders such as Diffuse Esophageal Spasm (an esophageal obstructive disorder characterized by dysphagia), Achalasia (an obstructive disorder in which the lower esophageal sphincter fails to relax adequately resulting in dysphagia), noncardiac chest pain and Functional Bowel Disorders such as the Irritable Bowel Syndrome (IBS), non-ulcer dyspepsia, and idiopathic constipation.

The afore mentioned esophageal and gastrointestinal disorders are currently incompletely understood, they are however thought to be the result of abnormal motility (smooth muscle activity). Therefore, we believe a rationale therapy would be to reduce the hypermotility and restore normal patterns of esophageal and gastrointestinal motility. In the United States the only drugs approved for treating motility disorders are cisapride and metoclopramide, the latter a dopamine D2 receptor antagonist that releases acetylcholine from the myenteric plexus, consequently such as agent enhances motility which is not desirable in treating hypermotility disorders. Presently, no efficacious therapy exists for the treatment of esophageal and gastrointestinal hypermotility disorders. Observations with anticholinergics and smooth muscle relaxants have been disappointing due to side effects such as dry mouth and blurred vision for the anticholinergics and headaches with smooth muscle relaxants such as nifedipine.

We have discovered a new class of selective muscarinic agents which have not previously been considered for the use in treating motility disorders of the gastrointestinal tract.

SUMMARY OF THE INVENTION

The method of this invention comprises administering to a patient suffering from gastrointestinal disorders an effective amount of a compound of the formula I

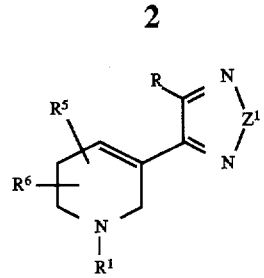

wherein $Z^1$ is oxygen or sulphur;

R is hydrogen, halogen, amino, —NHCO—$R^2$, $C_{3-7}$-cycloalkyl, $C_{4-10}$-(cycloalkylalkyl), —$Z^2$—$C_{3-7}$-cycloalkyl optionally substituted with $C_{1-6}$-alkyl, —$Z^2$—$C_{4-10}$-(cycloalkylalkyl), —$Z^2$—$C_{4-10}$-(cycloalkenylalkyl), —$Z^2$—$C_{4-10}$-(methylenecycloalkylalkyl), —NH—$R^2$, —$NR^2R^3$, —NH—$OR^2$, phenyl, phenoxy, benzoyl, benzyloxycarbonyl, tetrahydronaphtyl, indenyl, X, $R^2$, —$Z^2R^2$, —$SOR^2$, —$SO_2R^2$, —$Z^2$—$R^4$—$Z^3$—$R^3$, —$Z^2$—$R^4$—$Z^3$—$R^7$—$Z^4$—$R^3$, —$Z^2$—$R^4$—CO—$R^3$, —$Z^2$—$R^4$—$CO_2$—$R^3$, —$Z^2$—$R^4$—$O_2C$—$R^3$, —$Z^2$—$R^4$—CONH—$R^3$, —$Z^2$—$R^4$—NHCO—$R^3$, —$Z^2$—$R^4$—X, —$Z^2$—$R^4$—$Z^3$—X, wherein $Z^2$, $Z^3$ and $Z^4$ independently are oxygen or sulphur, and $R^2$ and $R^3$ independently are straight or branched $C_{1-5}$-alkyl, straight or branched $C_{2-15}$-alkenyl, straight or branched $C_{2-15}$-alkynyl, each of which is optionally substituted with halogen(s), —OH, —CN, —$CF_3$, —SH, —COOH, —NH—$R^2$, —$NR^2R^3$, $C_{1-6}$-alkyl ester, one or two phenyl, phenoxy, benzoyl or benzyloxycarbonyl wherein each aromatic group is optionally substituted with one or two halogen, —CN, $C_{1-4}$-alkyl or $C_{1-4}$-alkoxy, and wherein $R^4$ and $R^7$ independently are straight or branched $C_{1-10}$-alkylene, straight or branched $C_{2-10}$-alkenylene, straight or branched $C_{2-10}$-alkynylene, each of which is optionally substituted with halogen(s), —OH, —CN, —$CF_3$, —SH, —COOH, —NH—$R^2$, —$NR^2R^3$, $C_{1-6}$-alkyl ester, one or two phenyl, phenoxy, benzoyl or benzyloxycarbonyl, and X is a 5 or 6 membered heterocyclic group containing one to four N, O or S atom(s) or a combination thereof, which heterocyclic group is optionally substituted at carbon or nitrogen atom(s) with straight or branched $C_{1-6}$-alkyl, phenyl, benzyl or pyridine, or a carbon atom in the heterocyclic group together with an oxygen atom form a carbonyl group, or which heterocyclic group is optionally fused with a phenyl group; and $R^5$ and $R^6$ may be present at any position, including the point of attachment of the thiadiazole or oxadiazole ring, and independently are hydrogen, straight or branched $C_{1-5}$-alkyl, straight or branched $C_{2-5}$-alkenyl, straight or branched $C_{2-5}$-alkynyl, straight or branched $C_{1-10}$-alkoxy, straight or branched $C_{1-5}$-alkyl substituted with —OH, —OH, halogen, —$NH_2$ or carboxy;

$R^1$ is hydrogen, straight or branched $C_{1-5}$-alkyl, straight or branched $C_{2-5}$-alkenyl or straight or branched $C_{2-5}$-alkynyl; or a pharmaceutically acceptable salt thereof.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically acceptable inorganic or organic acid addition salts, and include the pharmaceutically acceptable salts listed in Journal of Pharmaceutical Science, 66, 2 (1977) which are hereby incorporated by reference.

Especially preferred salts include tartrate and hydrochloride.

As used herein, the term "patient" includes any mammal which could benefit from treatment of gastrointestinal disorders. The term particularly refers to a human patient, but is not intended to be so limited.

The thiadiazole and oxadiazole compounds used in the presently claimed method have been disclosed and claimed in U.S. Pat. Nos. 5,041,455, 5,043,345, European Patent Application 384288, PCT/DK91/00234 and PCT/DK91/00235. The thiadiazole and oxadiazole derivatives are known to be cholinergic muscarinic agents useful in the treatment of presenile and senile dementia. The compounds are believed to be useful for treating Alzheimer's disease, glaucoma, and painful conditions. Other disclosures suggest that thiadiazole compounds may be useful for the treatment of illnesses whose clinical manifestations are due to cholinergic deficiency, (European Patent Application 307142). Such illnesses include Huntington's chorea, tardive dyskinesia, hyperkinesia, mania, and Tourette Syndrome.

The compounds of the present invention are chemically and biologically different from that previously reported by Schiavone et al. (1988) and the compounds inhibit small intestinal and colonic motility through a cholinergic mechanism since the inhibition of motility is blocked by atropine (10 and 100 μg/kg i.v.). In addition these motility inhibiting compounds have the desirable feature of having minimal effects on salivation and heart rate.

In addition, the compounds of this method have been found to have a favourable profile of activity in a number of in vitro binding assays, designed to measure the degree of binding to neural receptors.

The compounds have $IC_{50}$ levels of less than 1 μM in the $^3$H-oxotremorine-M binding assay, indicating that the compounds have muscarinic receptor affinity.

This profile of activity in in vitro receptor binding assays, like that observed in the motility tests, would indicate that the compounds are effective in the treatment of gastrointestinal motility disorders.

Methods

Animals. Experiments were performed on fasted male ferret weighing 0.8–1.5 kg). Anaesthesia was induced with urethane (1.5 g/kg i.p.), a tracheal tube was inserted to provide a clear airway for spontaneous breathing and the body temperature was maintained at 38° C. using a homeothermic blanket. The left jugular vein was cannulated for the subsequent administration of drugs and the carotid artery for the continual measurement of blood pressure and heart rate.

Motility Measurements. Following a laporatomy segments of jejunum and colon were isolated from the remainder of the GI tract. In order to record motility of predominantly the circular smooth muscle, a saline-filled cannula was inserted in an oral directed into the jejunum and colon.

Experimental Protocol. After an initial stabilization period, spontaneous motility was recorded for 30 min. then a bolus injection of drug was administered i.v. and flushed through the cannula with 1 ml of physiological saline (37° C.). After 10 min. a second dose was investigated and changes in motility recorded for 10 min. If motility did not return to basal (pretreatment levels) more time was allowed between doses (up to 20 min.). All drugs were made up in physiological saline and made fresh daily.

Data Analysis. Following the bolus injection of compound the duration of loss of gastrointestinal motility was calculated. Most of the compounds were tested at screening doses of 1, 3, 10 and 30 μg/kg i.v.

The affinity of the compounds for the muscarinic receptors was determined using the non-selective agonist ligand, $^3$H-oxotremorine-M. Birdsdall N. J. M., Hulme E. C., and Burgen A. S. V., "The Character of Muscarinic Receptors in Different Regions of the Rat Brain", 207 Proc. Roy. Soc. 1 (London, Series B, 1980). The results of this assay are described in Table I below. Each compound was tested to determine the affinity of the compound for the muscarinic receptors using the following procedure.

For each in vitro binding, male Sprague-Dawley (Harlan Sprague-Dawley, Indianapolis, Ind.) rats weighing from about 100 to about 150 grams each were sacrificed by decapitation. The brains were quickly removed and the cerebral cortex were dissected from the brain. The cerebral cortex tissue was homogenized in 10 volumes of 0.32M sucrose and homogenized for about 10 minutes at about 1000×g. The supernatant was centrifuged at about 12,000×g for about 10 minutes and the resulting pellet was resuspended in 20 mM tris-Cl, pH 7.4. The resuspended pellet was centrifuged again for about 10 minutes at about 50,000× g. The resulting homogenate was preincubated for about 10 minutes at about 25° C. and centrifuged again for about 10 minutes at about 50,000×g. The pellet was resuspended at 1 gram of pellet per 3 ml of buffer and frozen at about −80° C. until used.

The inhibition of binding of $^3$H-oxotremorine-M binding to muscarinic receptors was determined by mixing the compound of the Example, 3 nM $^3$H-oxotremorine-M (about 87 Ci/mmoles, New England Nuclear, Boston Mass.), and cerebral cortical membranes equivalent to about 10 mg wet weight, which is about 100 μg of cortical membrane protein, in about 1 ml total volume of 20 nM tris-Cl buffer, pH 7.4, containing 1 mM $MnCl_2$. The aforementioned homogenates mixture was incubated for about 15 minutes at about 25° C. and then the homogenates were filtered through glass filters (Whatman, GF/C) with vacuum. The filters were washed 3 times with about 2 ml of cold tris-Cl buffer, and placed in scintillation vials containing about 10 ml of scintillation fluid (Ready Protein+, Beckman, Fullerton, Calif.). Radioactivity trapped on the filters was determined by liquid scintillation spectrometry. Nonspecific binding was determined using 1 μM atropine. The concentration of compound required to inhibit specific binding 50% ($IC_{50}$) was determined using standardized computer assisted calculations. DeLean, A. et al. Am. J. Physiol., 235, (1978).

Test results obtained by testing some compounds of the present invention will appear from the following Table 1:

TABLE 1

| Compound No. | Inhibition of $^3$H—Oxo (nM) | Jejunal motility (μg/kg i.v.) | Colonic Motility (μg/kg i.v.) |
|---|---|---|---|
| 1 | 22 | | |
| 2 | 5.7 | | |
| 3 | 1.6 | | |
| 4 | 2.0 | | |
| 33 | 2.7 | 30 | 10 |
| 47 | 0.90 | | |
| 48 | 1.7 | | |
| 49 | 2.3 | | |
| 65 | 1.9 | | |
| 66 | 4.8 | | |
| 133 | 10.0 | 10 | 30 |
| 215 | 10.5 | | |
| 216 | 6.5 | | |
| 217 | 1.2 | | |
| 218 | 3.5 | | |
| 219 | 5.8 | | |
| 220 | 3.0 | | |
| 222 | 0.42 | | |
| 223 | 7.4 | | |
| 228 | 0.60 | | |

The compounds used in this method are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from gastrointestinal motility disorders it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula I or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

The compounds used in this method may be prepared by commonly known chemical methods. Most of the compounds may be prepared using the methods taught in in U.S. Pat. Nos. 5,041,455, 5,043,345, European Patent Application 384288, PCT/DK91/00234 and PCT/DK91/00235 which are hereby incorporated by reference. The following description is intended to illustrate possible synthetic routes for the preparation of the compounds utilized in this method.

The compounds may be prepared by a) alkylating a compound of formula II

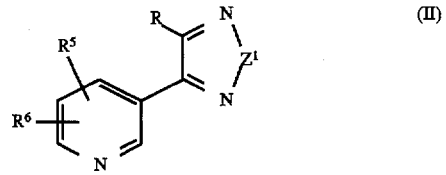

wherein $Z^1$, R, $R^5$ and $R^6$ have the meanings defined above with an alkyl halide and reducing the compound thus formed with hydride ions to form a compound of formula I

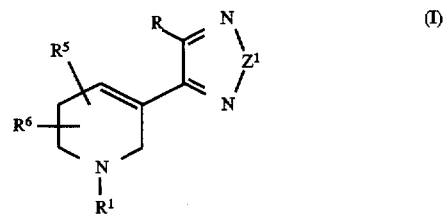

wherein $Z^1$, R, $R^1$, $R^5$ and $R^6$ have the meanings defined above, or b) oxidizing a compound of formula III

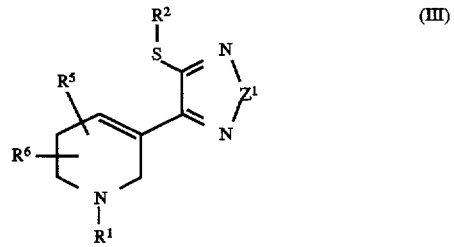

wherein $Z^1$, $R^1$, $R^2$, $R^5$ and $R^6$ have the meanings defined above by standard procedures to form a compound of formula IV

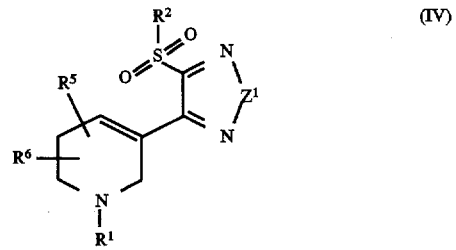

and subsequent displacement of —$SO_2$—$R^2$ with an appropriate nucleophile to form a compound of formula I.

It is to be understood that the invention extends to each of the stereoisomeric forms of the compounds of formula I as well as the racemates.

The following examples are included to more specifically describe the preparation of the compounds used in the method of this invention. The examples are not intended to limit the present invention in any way and should not be so construed.

EXAMPLE 1

A. 3-(3-Chloro-1,2,5-thiadiazol-4-yl)pyridine

To a solution of sulfurmonochloride (2.4 ml, 30 mmol) in N,N-dimethylformamide (5 ml) was slowly added alphaaminoalpha(3-pyridyl)acetonitrile (Archive der Pharmazie 289 (4) (1956)) (1.70 g, 10 mmol). The reaction mixture was stirred at room temperature for 18 h. Water (20 ml) was added and the aqueous phase was extracted with ether and the ether phase discharged. A 50% potassium hydroxide solution was added to the aqueous phase to pH>9. The aqueous phase was extracted several times with ether and the ether phases were dried and evaporated. The residue was purified by column chromatography (SiO$_2$, eluent: ethyl acetate/methylene chloride (1:1)). The title compound was collected in 45% (880 mg) yield. M$^+$: 197.

B. 3-(3-Methoxy-1,2,5-thiadiazol-4-yl)pyridine

To a solution of sodium (460 mg, 20 mmol) in methanol (10 ml) was added 3-(3-chloro-1,2,5-thiadiazol-4-yl)pyridine (750 mg, 3.8 mmol). The mixture was stirred at 50° C. for 1 h and evaporated. The residue was dissolved in water and extracted with methylene chloride. The combined organic phases were dried and evaporated to give the title compound, which crystallized with petroleum ether in a 630 mg (86%) yield.

C. 3-(3-Methoxy-1,2,5-thiadiazol-4-yl)-1-methylpyridinium iodide

A mixture of methyl iodide (0.37 ml, 6 mmol) and 3-(3-methoxy-1,2,5-thiadiazol-4-yl)pyridine (500 mg, 2.5 mmol) in acetone (10 ml) was stirred at room temperature for 18 h. The title compound precipitated from the solution and was collected by filtration. Yield: 1.0 g (100%).

D. 1,2,5,6-Tetrahydro-3-(3-methoxy-1,2,5-thiadiazol-4-yl)-1-methylpyridine oxalate Sodium borohydride (460 mg, 12 mmol) was added to a solution of 3-(3-methoxy-1,2,5-thiadiazol-4-yl)-1-methylpyridinium iodide (1.0 g, 3 mmol) in ethanol (99.9%, 20 ml) and the reaction mixture was stirred at room temperature for 1 h. After evaporation the residue was dissolved in water and extracted with methylene chloride. The dried organic phases were evaporated and the residue purified by column chromatography (SiO$_2$, eluent: ethyl acetate/methanol (4:1)). The title compound was crystallized as the oxalate salt from acetone. Yield: 390 mg. (M.p. 150° C.; M$^+$: 211; Compound 1).

EXAMPLE 2

A. 3-(3-Ethoxy-1,2,5-thiadiazol-4-yl)pyridine

To a solution of sodium (440 mg, 17 mmol) in ethanol (10 ml) was added 3-(3-chloro-1,2,5-thiadiazol-4-yl)pyridine (540 mg, 3.3 mmol). The mixture was stirred at 40° C. for 10 h and evaporated. The residue was dissolved in water and extracted with methylene chloride. The combined organic phases were dried and evaporated to yield 520 mg (76%) of the title compound.

B. 3-(3-Ethoxy-1,2,5-thiadiazol-4-yl)-1-methylpyridinium iodide

A mixture of methyl iodide (0.3 ml, 5 mmol) and 3-(3-ethoxy-1,2,5-thiadiazol-4-yl)pyridine (520 mg, 2.5 mmol) in acetone (10 ml) was stirred at room temperature for 18 h. The title compound precipitated from the solution and was collected by filtration to yield 0.72 g (83%).

C. 3-(3-Ethoxy-1,2,5-thiadiazol-4-yl)-1,2,5,6-tetrahydro-1-methylpyridine oxalate Sodium borohydride (300 mg, 8 mmol) was added to a solution of 3-(3-ethoxy-1,2,5-thiadiazol-4-yl)-1-methylpyridinium iodide (0.72 g, 2 mmol) in ethanol (99.9%, 20 ml) and the reaction mixture was stirred at room temperature for 1 h. After evaporation the residue was dissolved in water and extracted with methylene chloride. The dried organic phases were evaporated and the residue purified by column chromatography (SiO$_2$, eluent: ethyl acetate/methanol (4:1)). The title compound was crystallized as the oxalate salt from acetone, and recrystallized from methanol to yield 190 mg. (M.p. 137° C.; M$^+$: 225; Compound 2).

EXAMPLE 3

A. 3-(3-Propoxy-1,2,5-thiadiazol-4-yl)pyridine

To a solution of sodium (440 mg, 17 mmol) in 1-propanol (10 ml) was added 3-(3-chloro-1,2,5-thiadiazol-4-yl)pyridine (650 mg, 3.3 mmol). The mixture was stirred at 50° C. for 2 h and evaporated. The residue was dissolved in water and extracted with methylene chloride. The combined organic phases were dried and evaporated to yield 700 mg (96%) of the title compound.

B. 3-(3-Propoxy-1,2,5-thiadiazol-4-yl)-1-methylpyridinium iodide

A mixture of methyl iodide (0.37 ml, 6 mmol) and 3-(3-propoxy-1,2,5-thiadiazol-4-yl)pyridine (700 mg, 3.1 mmol) in acetone (10 ml) was stirred at room temperature for 18 h. The title compound precipitated from the solution and was collected by filtration to yield 0.98 g (88%).

C. 1,2,5,6-Tetrahydro-1-methyl-3-(3-propoxy-1,2,5-thiadiazol-4-yl)-pyridine oxalate Sodium borohydride (380 mg, 10 mmol) was added to a solution of 3-(3-propoxy-1,2,5-thiadiazol-4-yl)-1-methylpyridinium iodide (980 mg, 2.7 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$ eluent: ethyl acetate/methanol (4:1)). The title compound was crystallized as the oxalate salt from acetone to yield 440 mg. (M.p. 148° C.; M$^+$: 239; Compound 3).

EXAMPLE 4

A. 3-(3-Butoxy-1,2,5-thiadiazol-4-yl)pyridine

To a solution of sodium (290 mg, 12.5 mmol) in n-butanol (10 ml) was added 3-(3-chloro-1,2,5-thiadiazol-4-yl)pyridine (490 mg, 2.5 mmol). The mixture was stirred at 25° C. for 18 h and evaporated. The residue was dissolved in water and extracted with methylene chloride. The combined organic phases were dried and evaporated to yield 580 mg (100%) of the title compound.

B. 3-(3-Butoxy-1,2,5-thiadiazol-4-yl)-1-methylpyridinium iodide

A mixture of methyl iodide (0.3 ml, 5 mmol) and 3-(3-butoxy-1,2,5-thiadiazol-4-yl)pyridine (580 mg, 2.5 mmol) in acetone (5 ml) was stirred at room temperature for 18 h. The title compound precipitated from the solution and was collected by filtration to yield 0.60 g (64%).

C. 3-(3-Butoxy-1,2,5-thiadiazol-4-yl)-1,2,5,6-tetrahydro-1-methylpyridine oxalate Sodium borohydride (240 mg, 6.4 mmol) was added to a solution of 3-(3-butoxy-1,2,5-thiadiazol-4-yl)-1-methylpyridinium iodide (0.60 g, 1.6 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 280 mg. (M.p. 158° C.; M$^+$: 253; Compound 4).

EXAMPLE 5

A. 3-(3-Isopropoxy-1,2,5-thiadiazol-4-yl)pyridine

To a solution of sodium (290 mg, 12.5 mmol) in isopropanol (10 ml) was added 3-(3-chloro-1,2,5-thiadiazol-4-yl)

pyridine (490 mg, 2.5 mmol). The mixture was stirred at 25° C. for 18 h and evaporated. The residue was dissolved in water and extracted with ethyl acetate. The combined organic phases were dried and evaporated to yield 540 mg (98%) of the title compound.

B. 3-(3-Isopropoxy-1,2,5-thiadiazol-4-yl)-1-methylpyridinium iodide

A mixture of methyl iodide (0.3 ml, 5 mmol) and 3-(3-isopropoxy-1,2,5-thiadiazol-4-yl)pyridine (540 mg, 2.4 mmol) in acetone (5 ml) was stirred at room temperature for 18 h. The title compound precipitated from the solution and was collected by filtration to yield 0.68 g (77%).

C. 1,2,5,6-Tetrahydro-3-(3-isopropoxy-1,2,5-thiadiazol-4-yl)-1-methylpyridine oxalate Sodium borohydride (280 mg, 7.2 mmol) was added to a solution of 3-(3-isopropoxy-1,2,5-thiadiazol-4-yl)-1-methylpyridinium iodide (650 mg, 1.8 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 280 mg. (M.p. 164° C.; M$^+$: 239; Compound 5).

EXAMPLE 6

A. 3-(3-Pentyloxy-1,2,5-thiadiazol-4-yl)pyridine

To a solution of sodium (230 mg, 10 mmol) in 1-pentanol (20 ml) was added 3-(3-chloro-1,2,5-thiadiazol-4-yl)pyridine (490 mg, 2.5 mmol). The mixture was stirred at 50° C. for 3 h and evaporated. The residue was dissolved in water and extracted with methylene chloride. The combined organic phases were dried and evaporated to give the wanted compound.

B. 3-(3-Pentyloxy-1,2,5-thiadiazol-4-yl)-1-methylpyridinium iodide

A mixture of methyl iodide (0.3 ml, 5 mmol) and 3-(3-pentyloxy-1,2,5-thiadiazol-4-yl)pyridine (620 mg, 2.5 mmol) in acetone (5 ml) was stirred at room temperature for 18 h. The title compound precipitated from the solution and was collected by filtration to yield 0.81 g (84%).

C. 1,2,5,6-Tetrahydro-1-methyl-3-(3-pentyloxy-1,2,5-thiadiazol-4-yl)-pyridine oxalate Sodium borohydride (300 mg, 8 mmol) was added to a solution of 3-(3-pentyloxy-3,2,5-thiadiazol-4-yl)-1-methylpyridinium iodide (0.81 g, 2 mmol) in ethanol (99.9%, 20 ml) and the reaction mixture was stirred at 0° C. for 1 h. After evaporation the residue was dissolved in water and extracted with ether. The dried organic phases were evaporated and the residue purified by column chromatography (SiO$_2$, eluent: ethyl acetate/methanol (4:1)). The title compound was crystallized as the oxalate salt from acetone, and recrystallized from methanol to yield 220 mg. (M.p. 150° C.; M$^+$: 267; Compound 6).

EXAMPLE 7

A. 3-(3-isobutoxy-1,2,5-thiadiazol-4-yl)pyridine

To a solution of sodium (230 mg, 10 mmol) in isobutanol (10 ml) was added 3-(3-chloro-1,2,5-thiadiazol-4-yl)pyridine (490 mg, 2.5 mmol). The mixture was stirred at 50° C. for 3 h and evaporated. The residue was dissolved in water and extracted with methylene chloride. The combined organic phases were dried and evaporated to give the wanted compound.

B. 3-(3-Isobutoxy-1,2,5-thiadiazol-4-yl)-1-methylpyridinium iodide

A mixture of methyl iodide (0.6 ml, 10 mmol) and 3-(3-isobutoxy-1,2,5-thiadiazol-4-yl)pyridine (588 mg, 2.5 mmol) in acetone (5 ml) was stirred at room temperature for 18 h. The title compound precipitated from the solution and was collected by filtration to yield 0.88 g (87%).

C. 1,2,5,6-Tetrahydro-3-(3-isobutoxy-1,2,5-thiadiazol-4-yl)-1-methylpyridine oxalate Sodium borohydride (160 mg, 4.3 mmol) was added to a solution of 3-(3-isobutoxy-1,2,5-thiadiazol-4-yl)-1-methylpyridinium iodide (0.82 g, 2.2 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 400 mg. (M.p. 135° C.; M$^+$: 253; Compound 7).

EXAMPLE 8

A. 3-(3-Isopentyloxy-1,2,5-thiadiazol-4-yl)pyridine

To a solution of sodium (230 mg, 10 mmol) in isopentanol (20 ml) was added 3-(3-chloro-1,2,5-thiadiazol-4-yl)pyridine (490 mg, 2.5 mmol). The mixture was stirred at 50° C. for 2 h and evaporated. The residue was dissolved in water and extracted with ether. The combined organic phases were dried and evaporated to give the wanted compound.

B. 3-(3-Isopentyloxy-1,2,5-thiadiazol-4-yl)-1-methylpyridinium iodide

A mixture of methyl iodide (0.5 ml, 10 mmol) and 3-(3-isopentyloxy-1,2,5-thiadiazol-4-yl)pyridine (622 mg, 2.5 mmol) in acetone (5 ml) was stirred at room temperature for 18 h. The title compound precipitated from the solution and was collected by filtration to yield 0.78 g (81%).

C. 1,2,5,6-Tetrahydro-3-(3-isopentyloxy-1,2,5-thiadiazol-4-yl)-1-methylpyridine oxalate Sodium borohydride (150 mg, 4 mmol) was added to a solution of 3-(3-isopentyloxy-1,2,5-thiadiazol-4-yl)-1-methylpyridinium iodide (780 mg, 2 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 350 mg. (M.p. 152° C.; M$^+$: 267; Compound 8).

EXAMPLE 9

A. 3-(3-Hexyloxy-1,2,5-thiadiazol-4-yl)pyridine

To a solution of sodium (230 mg, 10 mmol) in 1-hexanol (15 ml) was added 3-(3-chloro-1,2,5-thiadiazol-4-yl)pyridine (490 mg, 2.5 mmol). The mixture was stirred at 50° C. for 2 h and evaporated. The residue was dissolved in water and extracted with ether. The combined organic phases were dried and evaporated to give the wanted compound.

B. 3-(3-Hexyloxy-1,2,5-thiadiazol-4-yl)-1-methylpyridinium iodide

A mixture of methyl iodide (0.5 ml, 7.5 mmol) and 3-(3-hexyloxy-1,2,5-thiadiazol-4-yl)pyridine (658 mg, 2.5 mmol) in acetone (5 ml) was stirred at room temperature for 18 h. The title compound precipitated from the solution and was collected by filtration to yield 0.81 g (80%).

C. 3-(3-Hexyloxy-1,2,5-thiadiazol-4-yl)-1,2,5,6-tetrahydro-1-methylpyridine oxalate Sodium borohydride (230 mg, 6 mmol) was added to a solution of 3-(3-hexyloxy-1,2,5-thiadiazol-4-yl)-1-methylpyridinium iodide (810 mg, 2 mmol) in ethanol (99.9%, 20 ml) and the reaction mixture was stirred at room temperature for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 350 mg. (M.p. 148° C.; M$^+$: 281; Compound 9).

EXAMPLE 10

A. 3-(3-Benzyloxy-1,2,5-thiadiazol-4-yl)pyridine

To a solution of sodium (490 mg, 2.5 mmol) in benzyl alcohol (15 ml) was added 3-(3-chloro-1,2,5-thiadiazol-4-yl)pyridine (490 mg, 2.5 mmol). The mixture was stirred at 50° C. for 2 h and evaporated. The residue was dissolved in water and extracted with ether. The combined organic phases were dried and evaporated to give the wanted compound.

B. 3-(3-Benzyloxy-1,2,5-thiadiazol-4-yl)-1-methylpyridinium iodide

A mixture of methyl iodide (0.5 ml, 7.5 mmol) and 3-(3-benzyloxy-1,2,5-thiadiazol-4-yl)pyridine (673 mg, 2.5 mmol) in acetone (5 ml) was stirred at room temperature for 18 h. The title compound precipitated from the solution and was collected by filtration to yield 0.75 g (73%).

C. 3-(3-Benzyloxy-1,2,5-thiadiazol-4-yl)-1,2,5,6-tetrahydro-1-methylpyridine oxalate Sodium borohydride (230 mg, 6 mmol) was added to a solution of 3-(3-benzyloxy-1,2,5-thiadiazol-4-yl)-1-methylpyridinium iodide (750 mg, 1.8 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 340 mg. (M.p. 149° C.; M$^+$: 287; Compound 10).

EXAMPLE 11

A. 3-(3-(3-Butenyloxy)-1,2,5-thiadiazol-4-yl)pyridine

To a solution of 3-buten-1-ol (540 mg, 7.5 mmol) and sodium hydride (180 mg, 7.5 mmol) in dry tetrahydrofuran was added a solution of 3-(3-chloro-1,2,5-thiadiazol-4-yl)pyridine (490 mg, 2.5 mmol) in dry tetrahydrofuran. The reaction mixture was stirred at room temperature for 1 h. Water was added and the mixture was extracted with ether. The ether phase was dried and evaporated to yield 650 mg of the title compound.

B. 3-(3-(3-Butenyloxy)-1,2,5-thiadiazol-4-yl)-1-methylpyridinium iodide

A mixture of methyl iodide (0.5 ml, 7.5 mmol) and 3-(3-(3-butenyloxy)-1,2,5-thiadiazol-4-yl)pyridine (583 mg, 2.5 mmol) in acetone (5 ml) was stirred at room temperature for 18 h. The title compound precipitated from the solution and was collected by filtration to yield 890 mg (96%).

C. 3-(3-(3-Butenyloxy)-1,2,5-thiadiazol-4-yl)-1,2,5,6-tetrahydro-1-methylpyridine oxalate Sodium borohydride (210 mg, 5.5 mmol) was added to a solution of 3-(3-(3-butenyloxy)-1,2,5-thiadiazol-4-yl)-1-methylpyridinium iodide (1.03 g, 2.8 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 380 mg. (M.p. 141° C.; M$^+$: 251; Compound 11).

EXAMPLE 12

A. 3-(3-(2-Butynyloxy)-1,2,5-thiadiazol-4-yl)pyridine

To a solution of 2-butyn-1-ol (530 mg, 7.5 mmol) and sodiumhydride (180 mg, 7.5 mmol) in dry tetrahydrofuran was added a solution of 3-(3-chloro-1,2,5-thiadiazol-4-yl)pyridine (490 mg, 2.5 mmol) in dry tetrahydrofuran. The reaction mixture was stirred at room temperature for 2 h. Water was added and the mixture was extracted with ether. The ether phase was dried and evaporated to give the title compound.

B. 3-(3-(2-Butynyloxy)-1,2,5-thiadiazol-4-yl)-1-methylpyridinium iodide

A mixture of methyl iodide (0.5 ml, 7.5 mmol) and 3-(3-(2-butynyloxy)-1,2,5-thiadiazol-4-yl)pyridine (578 mg, 2.5 mmol) in acetone (5 ml) was stirred at room temperature for 18 h. The title compound precipitated from the solution and was collected by filtration to yield 0.88 g (95%).

C. 3-(3-(2-Butynyloxy)-1,2,5-thiadiazol-4-yl)-1,2,5,6-tetrahydro-1-methylpyridine oxalate Sodium borohydride (180 mg, 4.7 mmol) was added to a solution of 3-(3-(2-butynyloxy)-1,2,5-thiadiazol-4-yl)-1-methylpyridinium iodide (0.88 g, 2.35 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone, and recrystallized in methanol to yield 140 mg. (M.p. 158° C.; M$^+$: 249; Compound 12).

EXAMPLE 13

A. 3-(3-Propargyloxy-1,2,5-thiadiazol-4-yl)pyridine

To a solution of propargyl alcohol (420 mg, 7.5 mmol) and sodium hydride (180 mg, 7.5 mmol) in dry tetrahydrofuran was added a solution of 3-(3-chloro-1,2,5-thiadiazol-4-yl)pyridine (490 mg, 2.5 mmol) in dry tetrahydrofuran. The reaction mixture was stirred at room temperature for 2 h. Water was added and the mixture was extracted with ether. The ether phase was dried and evaporated to yield 530 mg (98%) of the title compound.

B. 3-(3-Propargyloxy-1,2,5-thiadiazol-4-yl)-1-methylpyridinium iodide

A mixture of methyl iodide (0.45 ml, 7.2 mmol) and 3-(3-propargyloxy-1,2,5-thiadiazol-4-yl)pyridine (430 mg, 2.4 mmol) in acetone (5 ml) was stirred at room temperature for 18 h. The title compound precipitated from the solution and was collected by filtration to yield 0.58 g (67%).

C. 1,2,5,6-Tetrahydro-1-methyl-3-(3-propargyloxy-1,2,5-thiadiazol-4-yl)pyridine oxalate Sodium borohydride (230 mg, 6 mmol) was added to a solution of 3-(3-propargyloxy-1,2,5-thiadiazol-4-yl)-1-methylpyridinium iodide (0.68 g, 1.9 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 200 mg. (M.p. 155° C.; M$^+$: 235; Compound 13).

EXAMPLE 14

A. 3-(3-Cyclopropylmethoxy-1,2,5-thiadiazol-4-yl)pyridine

To a solution of cyclopropylcarbinol (360 mg, 5 mmol) and sodium hydride (110 mg, 5 mmol) in dry tetrahydrofuran was added a solution of 3-(3-chloro-1,2,5-thiadiazol-4- yl)pyridine (490 mg, 2.5 mmol) in dry tetrahydrofuran. The reaction mixture was stirred at room temperature for 3 h. Water was added and the mixture was extracted with ether. The ether phase was dried and evaporated to yield 400 mg (69%) of the title compound.

B. 3-(3-Cyclopropylmethoxy-1,2,5-thiadiazol-4-yl)-1-methylpyridinium iodide

A mixture of methyl iodide (0.25 ml, 4 mmol) and 3-(3-cyclopropylmethoxy-1,2,5-thiadiazol-4-yl)pyridine (400 mg, 1.7 mmol) in acetone (5 ml) was stirred at room temperature for 36 h. The title compound precipitated from the solution and was collected by filtration to yield 0.41 g (65%).

C. 3-(3-Cyclopropylmethoxy-1,2,5-thiadiazol-4-yl)-1,2,5,6-tetrahydro-1-methylpyridine oxalate Sodium borohydride (170 mg, 4.4 mmol) was added to a solution of 3-(3-cyclopropylmethoxy-1,2,5-thiadiazol-4-yl)-1-methylpyridinium iodide (410 mg, 1.1 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 130 mg. (M.p. 153° C.; M$^+$: 251; Compound 14).

EXAMPLE 15

A. 3-(3-Chloro-1,2,5-thiadiazol-4-yl)-1-methylpyridinium iodide

A solution of 3-(3-chloro-1,2,5-thiadiazol-4-yl)pyridine (1.98 g, 10 mmol) and methyl iodide (4.25 g, 30 mmol) in acetone (10 ml) was stirred at room temperature for 16 h. The precipitate was collected by filtration to yield 3.40 g (100%) of the title compound.

B. 3-(3-Chloro-1,2,5-thiadiazol-4-yl)-1,2,5,6-tetrahydro-1-methylpyridine oxalate To a suspension of sodium borohydride (330 mg, 8.6 mmol) in ethanol (20 ml) was added 3-(3-chloro-1,2,5-thiadiazol-4-yl)-1-methylpyridinium iodide (1.46 g, 4.3 mmol) at 0° C. The reaction mixture was stirred for 1 h at 0° C. Water was added and the mixture was extracted with ethyl acetate. After drying, the ethyl acetate phase was evaporated and the residue purified by column chromatography (eluent: ethyl acetate:methanol (4:1)). Yield: 880 mg (95%). Crystallization with oxalic acid from acetone gave the title compound. (M.p. 124° C.; M$^+$: 215 and 217; Compound 16).

C. 1,2,5,6-Tetrahydro-3-(3-methoxyethoxy-1,2,5-thiadiazol-4-yl)-1-methylpyridine oxalate To a solution of sodium (120 mg, 5 mmol) in 2-methoxyethanol (10 ml) was added 3-(3-chloro-1,2,5-thiadiazol-4-yl)-1,2,5,6-tetrahydro-1-methylpyridine oxalate (310 mg, 1 mmol). The mixture was stirred at 50° C. for 18 h and evaporated. The residue was dissolved in water and extracted with ethyl acetate. The combined organic phases were dried and evaporated. The title compound was crystallized as the oxalate salt from acetone to yield 270 mg. (M.p. 152.1° C.; M$^+$: 253; Compound 15).

D. 3-(3-Chloro-1,2,5-thiadiazol-4-yl)-1,2,5,6-tetrahydropyridine hydrochloride

To a solution of 3-(3-chloro-1,2,5-thiadiazol-4-yl)-1,2,5,6-tetrahydro-1-methylpyridine (670 mg, 3.1 mmol) in 1,2-dichloroethane (20 ml) was added a solution of 1-chloroethyl-chloroformate (440 mg, 3.1 mmol) in 1,2-dichloroethane at 0° C. The reaction mixture was heated to 40° C. for 2 h and evaporated. The residue was dissolved in methanol and heated to reflux for 1 h. After cooling to room temperature the precipitate was collected by filtration to yield 320 mg (41%). (M.p. 224° C.; M$^+$: 201 and 203; Compound 17).

E. 3-(3-Butoxy-1,2,5-thiadiazol-4-yl)-1,2,5,6-tetrahydropyridine oxalate

To a solution of sodium (150 mg, 6.5 mmol) in 1-butanol (15 ml) was added 3-(3-chloro-1,2,5-thiadiazol-4-yl)-1,2,5,6-tetrahydropyridine hydrochloride (240 mg, 1 mmol). The reaction mixture was stirred at 50° C. for 1 h. After evaporation the residue was dissolved in water and extracted with ethyl acetate. The ethyl acetate phase was dried and evaporated to give an oil (200 mg). Crystallization as the oxalate salt from acetone gave the title compound. Yield: 170 mg (52%). (M.p. 173°–174° C.; M$^+$: 239; Compound 18).

EXAMPLE 16

A. 3-(3-Chloro-1,2,5-thiadiazol-4-yl)-1-ethylpyridiniumiodide

A solution of 3-(3-chloro-1,2,5-thiadiazol-4-yl)pyridine (1.13 g, 5.7 mmol) and ethyl iodide (22.65 g, 17 mmol) in acetone (15 ml) was stirred at 40° C. for 16 h. The precipitate was collected by filtration giving the title compound. Yield: 510 mg (26%).

B. 3-(3-Chloro-1,2,5-thiadiazol-4-yl)-1-ethyl-1,2,5,6-tetrahydropyridine oxalate To a suspension of sodium borohydride (170 mg, 4.5 mmol) in ethanol (10 ml) was added 3-(3-chloro-1,2,5-thiadiazol-4-yl)-1-ethylpyridinium iodide (510 mg, 1.5 mmol) at 0° C. The mixture was stirred for 1 h at 0° C. Water was added and the mixture was extracted with ethyl acetate. After drying, the ethyl acetate phase was evaporated and the residue purified by column chromatography (eluent: ethyl acetate/methanol (4:1)). Crystallization with oxalic acid from acetone gave the title compound to yield 70 mg. (M.p. 143° C.; M$^+$: 229 and 231; Compound 19).

EXAMPLE 17

A. 3-(3-Ethoxy-1,2,5-thiadiazol-4-yl)-1-ethylpyridinium iodide

A solution of 3-(3-ethoxy-1,2,5-thiadiazol-4-yl)pyridine (0.90 g, 4.3 mmol) and ethyl iodide (2.03 g, 13 mmol) in acetone (4 ml) was stirred at 40° C. for 16 h. The precipitate was collected by filtration giving the title compound to yield 1.34 g (86%).

B. 3-(3-Ethoxy-1,2,5-thiadiazol-4-yl)-1-ethyl-1,2,5,6-tetrahydropyridine oxalate To a suspension of sodium borohydride (410 mg, 10.8 mmol) in ethanol (10 ml) was added 3-(3-ethoxy-1,2,5-thiadiazol-4-yl)-1-ethylpyridinium iodide (1.32 g, 3.6 mmol) at 0° C. The mixture was stirred for 1 h at 0° C. Water was added and the mixture was extracted with ethyl acetate. After drying, the ethyl acetate phase was evaporated and the residue purified by column chromatography (eluent: ethyl acetate/methanol (4:1)). Crystallization with oxalic acid from acetone gave a yield of 0.49 g of the title compound. (M.p. 120°–122° C.; M$^+$: 239; Compound 20).

The following compounds were prepared in exactly the same manner:

3-(3-Hexylthio-1,2,5-thiadiazol-4-yl)-1,2,5,6-tetrahydro-1-ethylpyridine oxalate from 3-(3-Hexylthio-1,2,5-thiadiazol-4-yl)pyridine. M.p. 134°–135° C. Compound 209.

3-(3-Ethylthio-1,2,5-thiadiazol-4-yl)-1,2,5,6-tetrahydro-1-ethylpyridine oxalate from 3-(3-ethylthio-1,2,5-thiadiazol-4-yl)pyridine. M.p. 151°–152° C. Compound 210.

3-(3-Hexyloxy-1,2,5-thiadiazol-4-yl)-1,2,5,6-tetrahydro-1-ethylpyridine oxalate from 3-(3-hexyloxy-1,2,5-thiadiazol-4-yl)pyridine. M.p. 138°–139° C. Compound 211.

EXAMPLE 18

3-(3-Heptyloxy-1,2,5-thiadiazol-4-yl)-1,2,5,6-tetrahydro-1-methylpyridine oxalate To a solution of sodium (120 mg, 5 mmol) in 1-heptanol (10 ml) was added 3-(3-chloro-1,2,5-thiadiazol-4-yl)-1,2,5,6-tetrahydro-1-methylpyridine oxalate (310 mg, 1 mmol). The reaction mixture was stirred at 50° C. for 18 h. After evaporation the residue was dissolved in water and extracted with ethyl acetate. The ethyl acetate phase was dried and evaporated to give an oil. Crystallization as the oxalate salt from acetone gave the title compound. Yield: 270 mg (70%). (M.p. 152° C.; M$^+$: 295; Compound 21).

EXAMPLE 19

A. 3-(3-(3-Pentynyloxy)-1,2,5-thiadiazol-4-yl)pyridine

To a solution of 3-pentyn-1-ol (750 mg, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. 3-(3-(3-Pentynyloxy)-1,2,5-thiadiazol-4-yl)-1-methylpyridinium iodide

A mixture of methyl iodide (0.6 ml, 9 mmol) and 3-(3-(3-pentynyloxy)-1,2,5-thiadiazol-4-yl)pyridine (3 mmol) in acetone (10 ml) was stirred at room temperature for 18 h. The title compound precipitated from the solution and was collected by filtration to yield 0.68 g (59%).

C. 3-(3-(3-Pentynyloxy)-1,2,5-thiadiazol-4-yl)-1,2,5,6-tetrahydro-1-methylpyridine oxalate Sodium borohydride (150 mg, 4 mmol) was added to a solution of 3-(3-(3-pentynyloxy)-1,2,5-thiadiazol-4-yl)-1-methylpyridinium iodide (0.68 g, 1.7 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 240 mg. (M.p. 166°–167° C.; M$^+$: 263; Compound 22).

EXAMPLE 20

A. 3-(3-(4-Pentenyloxy)-1,2,5-thiadiazol-4-yl)pyridine

To a solution of 4-penten-1-ol (640 mg, 7.5 mmol) and sodium hydride (260 mg, 7.5 mmol) in dry tetrahydrofuran was added a solution of 3-(3-chloro-1,2,5-thiadiazol-4-yl)pyridine (490 mg, 2.5 mmol) in dry tetrahydrofuran. The reaction mixture was stirred at room temperature for 1 h. Water was added and the mixture was extracted with ether. The ether phase was dried and evaporated to give the title compound.

B. 3-(3-(4-Pentenyloxy)-1,2,5-thiadiazol-4-yl)-1-methylpyridinium iodide

A mixture of methyl iodide (0.5 ml, 7.5 mmol) and 3-(3-(4-pentenyloxy)-1,2,5-thiadiazol-4-yl)pyridine (2.5 mmol) in acetone (10 ml) was stirred at room temperature for 18 h. The title compound precipitated from the solution and was collected by filtration to yield 0.67 g (69%).

C. 3-(3-(4-Pentenyloxy)-1,2,5-thiadiazol-4-yl)-1,2,5,6-tetrahydro-1-methylpyridine oxalate Sodium borohydride (150 mg, 4 mmol) was added to a solution of 3-(3-(4-pentenyloxy)-1,2,5-thiadiazol-4-yl)-1-methylpyridinium iodide (0.67 g, 1.7 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 150 mg. (M.p. 141°–142° C.; M$^+$: 265; Compound 23).

EXAMPLE 21

A. 3-(3-(2-Propenyloxy)-1,2,5-thiadiazol-4-yl)pyridine

To a solution of allyl alcohol (650 mg, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. 3-(3-(2-Propenyloxy)-1,2,5-thiadiazol-4-yl)-1-methylpyridinium iodide

A mixture of methyl iodide (0.4 ml, 6 mmol) and 3-(3-(2-propenyloxy)-1,2,5-thiadiazol-4-yl)pyridine (3 mmol) in acetone (5 ml) was stirred at room temperature for 18 h. The title compound precipitated from the solution and was collected by filtration to give 0.96 g (88%).

C. 3-(3-(2-Propenyloxy)-1,2,5-thiadiazol-4-yl)-1,2,5,6-tetrahydro-1-methylpyridine oxalate Sodium borohydride (210 mg, 5.5 mmol) was added to a solution of 3-(3-(2-propenyloxy)-1,2,5-thiadiazol-4-yl)-1-methylpyridinium iodide (0.96 g, 2.6 mmol) in ethanol (99.9%, 25 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 270 mg. (M.p. 136°–137° C.; M$^+$: 237; Compound 24).

EXAMPLE 22

A. 3-(3-Octyloxy-1,2,5-thiadiazol-4-yl)pyridine

To a solution of sodium (350 mg, 15 mmol) in 1-octanol (10 ml) was added 3-(3-chloro-1,2,5-thiadiazol-4-yl)pyridine (590 mg, 3 mmol). The mixture was stirred at 50° C. for 1 h and evaporated. The residue was dissolved in water and extracted with methylene chloride. The combined organic phases were dried and evaporated to give the title compound.

B. 3-(3-Octyloxy-1,2,5-thiadiazol-4-yl)-1-methylpyridinium iodide

A mixture of methyl iodide (1 ml, 15 mmol) and 3-(3-octyloxy-1,2,5-thiadiazol-4-yl)pyridine (3 mmol) in acetone (5 ml) was stirred at room temperature for 18 h. The title compound precipitated from the solution and was collected by filtration to yield 0.81 g (62%).

C. 3-(3-Octyloxy-1,2,5-thiadiazol-4-yl)-1,2,5,6-tetrahydro-1-methylpyridine oxalate Sodium borohydride (210 mg, 5.6 mmol) was added to a solution of 3-(3-octyloxy-1,2,5-thiadiazol-4-yl)-1-methylpyridinium iodide (0.81 g, 1.87 mmol) in ethanol (99.9%, 10 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 330 mg. (M.p. 144°–145° C.; M$^+$: 309; Compound 25).

EXAMPLE 23

A. 3-(3-(3-Hexynyloxy)-1,2,5-thiadiazol-4-yl)pyridine

To a solution of 3-hexyn-1-ol (880 mg, 9 mmol) and sodium hydride (310 mg, 9 mmol) in dry tetrahydrofuran was added a solution of 3-(3-chloro-1,2,5-thiadiazol-4-yl) pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. 3-(3-(3-Hexynyloxy)-1,2,5-thiadiazol-4-yl)-1-methylpyridinium iodide

A mixture of methyl iodide (1 ml, 15 mmol) and 3-(3-(3-hexynyloxy)-1,2,5-thiadiazol-4-yl)pyridine (3 mmol) in acetone (5 ml) was stirred at room temperature for 18 h. The title compound precipitated from the solution and was collected by filtration to yield 0.85 g (71%).

C. 3-(3-(3-Hexynyloxy)-1,2,5-thiadiazol-4-yl)-1,2,5,6-tetrahydro-1-methylpyridine oxalate Sodium borohydride (190 mg, 5 mmol) was added to a solution of 3-(3-(3-hexynyloxy)-1,2,5-thiadiazol-4-yl)-1-methylpyridinium iodide (0.85 g, 2.1 mmol) in ethanol (99.9%, 10 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 350 mg. (M.p. 174°–175° C.; M$^+$: 277; Compound 26).

EXAMPLE 24

A. 3-(3-(3-Methyl-2-butenyloxy)-1,2,5-thiadiazol-4-yl) pyridine

To a solution of 3-methyl-2-buten-1-ol (780 mg, 9 mmol) and sodiumhydride (310 mg, 9 mmol) in dry tetrahydrofuran was added a solution of 3-(3-chloro-1,2,5-thiadiazol-4-yl) pyridine (590 mg, 3 mmol) in dry tetrahydrofuran. The reaction mixture was stirred at room temperature for 0.3 h. Water was added and the mixture was extracted with ether. The ether phase was dried and evaporated to give the title compound.

B. 3-(3-(3-Methyl-2-butenyloxy)-1,2,5-thiadiazol-4-yl)-1-methylpyridinium iodide A mixture of methyl iodide (1 ml, 15 mmol) and 3-(3-(3-methyl-2-butenyloxy)-1,2,5-thiadiazol-4-yl)pyridine (3 mmol) in acetone (3 ml) was stirred at room temperature for 18 h. The title compound precipitated from the solution and was collected by filtration to yield 0.92 g (79%).

C. 3-(3-(3-Methyl-2-butenyloxy)-1,2,5-thiadiazol-4-yl)-1,2,5,6-tetrahydro-1-methylpyridine oxalate Sodium borohydride (220 mg, 6 mmol) was added to a solution of 3-(3-(3-methyl-2-butenyloxy)-1,2,5-thiadiazol-4-yl)-1-methylpyridinium iodide (0.92 g, 2.3 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 380 mg. (M.p. 150°–151° C.; M$^+$: 265; Compound 27).

EXAMPLE 25

A. 3-(3-(3-Butenyl-2-oxy)-1,2,5-thiadiazol-4-yl)pyridine

To a solution of 3-buten-2-ol (650 mg, 9 mmol) and sodium hydride (310 mg, 9 mmol) in dry tetrahydrofuran was added a solution of 3-(3-chloro-1,2,5-thiadiazol-4-yl) pyridine (590 mg, 3 mmol) in dry tetrahydrofuran. The reaction mixture was stirred at room temperature for 18 h. Water was added and the mixture was extracted with ether. The ether phase was dried and evaporated to give the title compound.

B. 3-(3-(3-Butenyl-2-oxy)-1,2,5-thiadiazol-4-yl)-1-methylpyridinium iodide

A mixture of methyl iodide (1 ml, 15 mmol) and 3-(3-(3-butenyl-2-oxy)-1,2,5-thiadiazol-4-yl)pyridine (3 mmol) in acetone (3 ml) was stirred at room temperature for 18 h. The title compound precipitated from the solution and was collected by filtration to yield 0.73 g (65%).

C. 3-(3-(3-Butenyl-2-oxy)-1,2,5-thiadiazol-4-yl)-1,2,5,6-tetrahydro-1-methylpyridine oxalate Sodium borohydride (190 mg, 5 mmol) was added to a solution of 3-(3-(3-butenyl-2-oxy)-1,2,5-thiadiazol-4-yl)-1-methylpyridinium iodide (0.73 g, 1.9 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 270 mg. (M.p. 134°–135° C.; M$^+$: 251; Compound 28).

EXAMPLE 26

A. 3-(3-(4-Hexenyloxy)-1,2,5-thiadiazol-4-yl)pyridine

To a solution of 4-hexen-1-ol (900 mg, 9 mmol) and sodium hydride (310 mg, 9 mmol) in dry tetrahydrofuran was added a solution of 3-(3-chloro-1,2,5-thiadiazol-4-yl) pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. 3-(3-(4-Hexenyloxy)-1,2,5-thiadiazol-4-yl)-1-methylpyridinium iodide

A mixture of methyl iodide (1 ml, 15 mmol) and 3-(3-(4-hexenyloxy)-1,2,5-thiadiazol-4-yl)pyridine (3 mmol) in acetone (5 ml) was stirred at room temperature for 18 h. The title compound precipitated from the solution and was collected by filtration to yield 0.54 g (45%).

C. 3-(3-(4-Hexenyloxy)-1,2,5-thiadiazol-4-yl)-1,2,5,6-tetrahydro-1-methylpyridine oxalate Sodium borohydride (150 mg, 4 mmol) was added to a solution of 3-(3-(4-hexenyloxy)-1,2,5-thiadiazol-4-yl)-1-methylpyridinium iodide (0.54 g, 1.3 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 190 mg. (M.p. 151°–152° C.; M$^+$: 279; Compound 29).

EXAMPLE 27

A. trans-3-(3-(3-Hexenyloxy)-1,2,5-thiadiazol-4-yl) pyridine

To a solution of trans-3-hexen-1-ol (900 mg, 9 mmol) and sodium hydride (310 mg, 9 mmol) in dry tetrahydrofuran was added a solution of 3-(3-chloro-1,2,5-thiadiazol-4-yl) pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. trans-3-(3-(3-Hexenyloxy)-1,2,5-thiadiazol-4-yl)-1-methylpyridinium iodide

A mixture of methyl iodide (1 ml, 15 mmol) and trans-3-(3-(3-hexenyloxy)-1,2,5-thiadiazol-4-yl)pyridine (3 mmol) in acetone (5 ml) was stirred at room temperature for 18 h. The title compound precipitated from the solution and was collected by filtration to yield 0.90 g (75%).

C. trans-3-(3-(3-Hexenyloxy)-1,2,5-thiadiazol-4-yl)-1,2,5,6-tetrahydro-1-methylpyridine oxalate Sodium borohydride (190 mg, 5 mmol) was added to a solution of trans-3-(3-(3-hexenyloxy)-1,2,5-thiadiazol-4-yl)-1-methylpyridinium iodide (0.90 g, 2.2 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography ($SiO_2$, eluent: ethyl acetate/methanol (4:1)). The title compound was crystallized as the oxalate salt from acetone to yield 420 mg. (M.p. 163°–164° C.; $M^+$: 279; Compound 30).

EXAMPLE 28

A. cis-3-(3-(2-Pentenyloxy)-1,2,5-thiadiazol-4-yl)-pyridine

To a solution of cis-2-penten-1-ol (780 mg, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. cis-3-(3-(2-Pentenyloxy)-1,2,5-thiadiazol-4-yl)-1-methylpyridinium iodide

A mixture of methyl iodide (1 ml, 15 mmol) and cis-3-(3-(2-pentenyloxy)-1,2,5-thiadiazol-4-yl)pyridine (3 mmol) in acetone (5 ml) was stirred at room temperature for 18 h. The title compound precipitated from the solution and was collected by filtration to yield 0.53 g (46%).

C. cis-3-(3-(2-Pentenyloxy)-1,2,5-thiadiazol-4-yl)-1,2,5,6-tetrahyro-1-methylpyridine oxalate Sodium borohydride (150 mg, 4 mmol) was added to a solution of cis-3-(3-(2-pentenyloxy)-1,2,5-thiadiazol-4-yl)-1-methylpyridinium iodide (0.53 g, 1.3 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography ($SiO_2$, eluent: ethyl acetate/methanol (4:1)). The title compound was crystallized as the oxalate salt from acetone to yield 210 mg. (M.p. 143°–144° C.; $M^+$: 265; Compound 31).

EXAMPLE 29

A. cis-3-(3-(2-Hexenyloxy)-1,2,5-thiadiazol-4-yl)pyridine

To a solution of cis-2-hexen-1-ol (900 mg, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. cis-3-(3-(2-Hexenyloxy)-1,2,5-thiadiazol-4-yl)-1-methylpyridinium iodide

A mixture of methyl iodide (0.5 ml, 7.5 mmol) and cis-3-(3-(2-hexenyloxy)-1,2,5-thiadiazol-4-yl)pyridine (3 mmol) in acetone (4 ml) was stirred at room temperature for 18 h. The title compound precipitated from the solution and was collected by filtration.

C. cis-3-(3-(2-Hexenyloxy)-1,2,5-thiadiazol-4-yl)-1,2,5,6-tetrahydro-1-methylpyridine oxalate Sodium borohydride (150 mg, 4 mmol) was added to a solution of cis-3-(3-(2-hexenyloxy)-1,2,5-thiadiazol-4-yl)-1-methylpyridinium iodide (0.6 g, 1 mmol) in ethanol (99.9%, 20 ml) and the reaction mixture was stirred at −10° C. for 0.5 h. After evaporation the residue was dissolved in water and extracted with ethyl acetate. The dried organic phases were evaporated and the residue purified by column chromatography ($SiO_2$, eluent: ethyl acetate/methanol (4:1)). The title compound was crystallized as the oxalate salt from acetone to yield 150 mg. (M.p. 122°–123° C.; $M^+$: 279; Compound 32).

EXAMPLE 30

A. 3-(3-(5-Hexenyloxy)-1,2,5-thiadiazol-4-yl)pyridine

To a solution of 5-hexen-1-ol (900 mg, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. 3-(3-(5-Hexenyloxy)-1,2,5-thiadiazol-4-yl)-1-methylpyridinium iodide

A mixture of methyl iodide (0.5 ml, 7.5 mmol) and 3-(3-(5-hexenyloxy)-1,2,5-thiadiazol-4-yl)pyridine (3 mmol) in acetone (5 ml) was stirred at room temperature for 18 h. The title compound precipitated from the solution and was collected by filtration to yield 0.75 g (62%).

C. 3-(3-(5-Hexenyloxy)-1,2,5-thiadiazol-4-yl)-1,2,5,6-tetrahydro-1-methylpyridine oxalate Sodium borohydride (150 mg, 4 mmol) was added to a solution of 3-(3-(5-hexenyloxy)-1,2,5-thiadiazol-4-yl)-1-methylpyridinium iodide (0.75 g, 1.8 mmol) in ethanol (99.9%, 20 ml) and the reaction mixture was stirred at −10° C. for 0.5 h. After evaporation the residue was dissolved in water and extracted with ethyl acetate. The dried organic phases were evaporated and the residue purified by column chromatography ($SiO_2$, eluent: ethyl acetate/ methanol (4:1)). The title compound was crystallized as the oxalate salt from acetone to yield 250 mg. (M.p. 137°–138° C.; $M^+$: 279; Compound 33).

EXAMPLE 31

A. cis-3-(3-(3-Hexenyloxy)-1,2,5-thiadiazol-4-yl)pyridine

To a solution of cis-3-hexen-1-ol (900 mg, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. cis-3-(3-(3-Hexenyloxy)-1,2,5-thiadiazol-4-yl)-1-methylpyridinium iodide

A mixture of methyl iodide (0.5 ml, 7.5 mmol) and cis-3-(3-(3-hexenyloxy)-1,2,5-thiadiazol-4-yl)pyridine (3 mmol) in acetone (5 ml) was stirred at room temperature for 18 h. The title compound precipitated from the solution and was collected by filtration to yield 0.9 g (46%).

C. cis-3-(3-(3-Hexenyloxy)-1,2,5-thiadiazol-4-yl)-1,2,5,6-tetrahydro-1-methylpyridine oxalate Sodium borohydride (230 mg, 6 mmol) was added to a solution of cis-3-(3-(3-hexenyloxy)-1,2,5-thiadiazol-4-yl)-1-methylpyridinium iodide (0.90 g, 2.2 mmol) in ethanol (99.9%, 15 ml) and the reaction mixture was stirred at −10°

C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 300 mg. (M.p. 149°–150° C.; M$^+$: 279; Compound 34).

EXAMPLE 32

A. trans-3-(3-(2-Hexenyloxy)-1,2,5-thiadiazol-4-yl) pyridine

To a solution of trans-2-hexen-1-ol (900 mg, 9 mmol) and sodium hydride (310 mg, 9 mmol) in dry tetrahydrofuran was added a solution of 3-(3-chloro-1,2,5-thiadiazol-4-yl) pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. trans-3-(3-(2-Hexenyloxy)-1,2,5-thiadiazol-4-yl)-1-methylpyridinium iodide

A mixture of methyl iodide (0.5 ml, 7.5 mmol) and trans-3-(3-(2-hexenyloxy)-1,2,5-thiadiazol-4-yl)pyridine (3 mmol) in acetone (5 ml) was stirred at room temperature for 18 h. The title compound precipitated from the solution and was collected by filtration to yield 1.09 g (90%).

C. trans-3-(3-(2-Hexenyloxy)-1,2,5-thiadiazol-4-yl)-1,2,5,6-tetrahydro-1-methylpyridine oxalate Sodium borohydride (270 mg, 4 mmol) was added to a solution of trans-3-(3-(2-hexenyloxy)-1,2,5-thiadiazol-4-yl)-1-methylpyridinium iodide (1.09 g, 2.7 mmol) in ethanol (99.9%, 20 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 400 mg. (M.p. 130°–131° C.; M$^+$: 279; Compound 35).

EXAMPLE 33

A. 3-(1,2,5-Thiadiazol-3-yl)pyridine

To a solution of 1-butanethiol (2.7 g, 30 mmol) and sodium hydride (1.2 g, 30 mmol) in dry tetrahydrofuran was added a solution of 3-(3-chloro-1,2,5-thiadiazol-4-yl) pyridine (1.2 g, 6 mmol) in dry tetrahydrofuran. The reaction mixture was stirred at −10° C. for 0.5 h. Water was added and the mixture was extracted with ether. The ether phase was dried and evaporated. The residue was purified by column chromatography (SiO$_2$, eluent: ethyl acetate/ methylene chloride (1:1)) to give the title compound.

B. 3-(1,2,5-Thiadiazol-3-yl)-1-methylpyridinium iodide

A mixture of methyl iodide (1 ml, 15 mmol) and 3-(1,2, 5-thiadiazol-3-yl)pyridine (6 mmol) in acetone (5 ml) was stirred at room temperature for 18 h. The title compound precipitated from the solution and was collected by filtration to yield 1.2 g (74%).

C. 3-(1,2,5-Thiadiazol-3-yl)-1,2,5,6-tetrahydro-1-methylpyridine oxalate

Sodium borohydride (380 mg, 10 mmol) was added to a solution of 3-(1,2,5-thiadiazol-3-yl)-1-methylpyridinium iodide (1.2 g, 4.4 mmol) in ethanol (99.9%, 20 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 430 mg. (M.p. 189°–190° C.; M$^+$: 181; Compound 36).

EXAMPLE 34

1,2,5,6-Tetrahydro-3-(3-hexyloxy-1,2,5-thiadiazol-4-yl)pyridine oxalate

To a solution of 3-(3-hexyloxy-1,2,5-thiadiazol-4-yl)-1,2, 5,6-tetrahydro-1-methylpyridine (0.70 g, 2.4 mmol) in 1,2-dichloroethane (20 ml) was added a solution of 1-chloroethyl-chloroformate (0.35 g, 2.4 mmol) in 1,2-dichloroethane at 0° C. The reaction mixture was heated to 40° C. for 2 h and evaporated. The residue was dissolved in methanol and heated to reflux for 1 h and evaporated. The residue was dissolved in diluted sodium hydroxide and extracted with ether. The combined ether phases were dried and evaporated. Crystallization as the oxalate salt from acetone gave the title compound in 72% (620 mg) yield. (M.p. 157°–159° C.; M$^+$: 267; Compound 37).

In exactly the same manner the following compounds were prepared:

3-(3-Ethoxy-1,2,5-thiadiazol-4-yl)-1,2,5,6-tetrahydropyridine hydrochloride. M.p. 217°–218° C. Compound 215.

3-(3-Ethylthio-1,2,5-thiadiazol-4-yl)-1,2,5,6-tetrahydropyridine hydrochloride. M.p. 181°–182° C. Compound 216.

3-(3-Propylthio-1,2,5-thiadiazol-4-yl)-1,2,5,6-tetrahydropyridine oxalate. M.p. 190°–191° C. Compound 217.

3-(3-Butylthio-1,2,5-thiadiazol-4-yl)-1,2,5,6-tetrahydropyridine oxalate. M.p. 182°–183° C. Compound 218.

3-(3-Pentylthio-1,2,5-thiadiazol-4-yl)-1,2,5,6-tetrahydropyridine oxalate. M.p. 181°–182° C. Compound 219.

3-(3-Hexylthio-1,2,5-thiadiazol-4-yl-1,2,5,6-tetrahydropyridine oxalate. M.p. 173°–175° C. Compound 220.

3-(3-(4-Pentynylthio)-1,2,5-thiadiazol-4-yl)-1,2,5,6-tetrahydropyridine oxalate. M.p. 140°–142° C. Compound 221.

3-(3-(2,2,2-Trifluoroethylthio)-1,2,5-thiadiazol-4-yl)-1,2,5, 6-tetrahydropyridine hydrochloride. M.p. 105°–110° C. Compound 222.

3-(3-(2,2,2-Trifluoroethoxy)-1,2,5-thiadiazol-4-yl)-1,2,5,6-tetrahydropyridine hydrochloride. M.p. 149°–151° C. Compound 223.

3-(3-(2-Phenoxyethylthio)-1,2,5-thiadiazol-4-yl)-1,2,5,6-tetrahydropyridine oxalate. M.p. 191°–192° C. Compound 224.

EXAMPLE 35

A. 3-(3-(2-(2-Methoxyethoxy)ethoxy)-1,2,5-thiadiazol-4-yl)pyridine

To a solution of sodium (210 mg, 9 mmol) in 2-(2-methoxyethoxy)ethanol (10 ml) was added 3-(3-chloro-1,2, 5-thiadiazol-4-yl)pyridine (590 mg, 3 mmol). The mixture was stirred at 50° C. for 4 h and evaporated. The residue was dissolved in water and extracted with ether. The combined organic phases were dried and evaporated to give the title compound.

B. 3-(3-(2-(2-Methoxyethoxy)ethoxy)-1,2,5-thiadiazol-4-yl)-1-methylpyridinium iodide A mixture of methyl iodide (0.5 ml, 9 mmol) and 3-(3-(2-(2-methoxyethoxy)ethoxy)-1,2,5-thiadiazol-4-yl) pyridine (3 mmol) in acetone (10 ml) was stirred at room temperature for 18 h. The title compound precipitated from the solution and was collected by filtration to yield 0.76 g (60%).

C. 3-(3-(2-(2-Methoxyethoxy)ethoxy)-1,2,5-thiadiazol-4-yl)-1,2,5,6-tetrahydro-1-methylpyridine oxalate Sodium borohydride (150 mg, 4 mmol) was added to a solution of 3-(3-(2(2-methoxyethoxy)ethoxy)-1,2,5-thiadiazol-4-yl)-1-methylpyridinium iodide (0.76 g, 1.8 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/ methanol (4:1)). The title compound was crystallized as the oxalate salt from acetone to yield 70 mg. (M.p. 142°–143° C.; M$^+$: 299; Compound 38).

EXAMPLE 36

A. 3-(3-(3-Ethoxy-1-propoxy)-1,2,5-thiadiazol-4-yl)pyridine

To a solution of 3-ethoxy-1-propanol (940 mg, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 2 h. Water was added and the mixture was extracted with ether. The ether phase was dried and evaporated to give the title compound.

B. 3-(3-(3-Ethoxy-1-propoxy)-1,2,5-thiadiazol-4-yl)-1-methylpyridinium iodide

A mixture of methyl iodide (0.5 ml, 9 mmol) and 3-(3-ethoxy-1-propoxy-1,2,5-thiadiazol-4-yl)pyridine (3 mmol) in acetone (5 ml) was stirred at room temperature for 18 h. The title compound precipitated from the solution and was collected by filtration.

C. 3-(3-(3-Ethoxy-1-propoxy)-1,2,5-thiadiazol-4-yl)-1,2,5,6-tetrahydro-1-methylpyridine oxalate Sodium borohydride (190 mg, 5 mmol) was added to a solution of 3-(3-(3-ethoxy-1-propoxy)-1,2,5-thiadiazol-4-yl)-1-methylpyridinium iodide (3 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 210 mg. (M.p. 149°–150° C.; M$^+$: 283; Compound 39).

EXAMPLE 37

A. 3-(3-(2-Ethoxyethoxy)-1,2,5-thiadiazol-4-yl)pyridine

To a solution of 2-ethoxyethanol (1.08 g, 12 mmol) and sodium hydride (410 mg, 12 mmol) in dry tetrahydrofuran was added a solution of 3-(3-chloro-1,2,5-thiadiazol-4-yl)pyridine (790 mg, 4 mmol) in dry tetrahydrofuran. The mixture was stirred at room temperature for 2 h. Water was added and the mixture was extracted with ether. The ether phase was dried and evaporated to give the title compound.

B. 3-(3-(2-Ethoxyethoxy)-1,2,5-thiadiazol-4-yl)-1-methylpyridinium iodide

A mixture of methyl iodide (0.5 ml, 9 mmol) and 3-(3-(2-ethoxyethoxy)-1,2,5-thiadiazol-4-yl)pyridine (4 mmol) in acetone (3 ml) was stirred at room temperature for 18 h. The title compound precipitated from the solution and was collected by filtration to yield 1.45 g (92%).

C. 3-(3-(2-Ethoxyethoxy)-1,2,5-thiadiazol-4-yl)-1,2,5,6-tetrahydro-1-methylpyridine oxalate Sodium borohydride (350 mg, 9 mmol) was added to a solution of 3-(3-(2-ethoxyethoxy)-1,2,5-thiadiazol-4-yl)-1-methylpyridinium iodide (1.45 g, 3.7 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/ methanol (4:1)). The title compound was crystallized as the oxalate salt from acetone to yield 640 mg. (M.p. 153°–156° C.; M$^+$: 269; Compound 40).

EXAMPLE 38

A. 3-(3-(2-Butoxyethoxy)-1,2,5-thiadiazol-4-yl)pyridine

To a solution of 2-butoxyethanol (1.06 g, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 2 h. Water was added and the mixture was extracted with ether. The ether phase was dried and evaporated to give the title compound.

B. 3-(3-(2-Butoxyethoxy)-1,2,5-thiadiazol-4-yl)-1-methylpyridinium iodide

A mixture of methyl iodide (0.5 ml, 9 mmol) and 3-(3-(2-butoxyethoxy)-1,2,5-thiadiazol-4-yl)pyridine (3 mmol) in acetone (4 ml) was stirred at room temperature for 18 h. The title compound precipitated from the solution and was collected by filtration to yield 1.07 g (85%).

C. 3-(3-(2-Butoxyethoxy)-1,2,5-thiadiazol-4-yl)-1,2,5,6-tetrahydro-1-methylpyridine oxalate Sodium borohydride (230 mg, 6 mmol) was added to a solution of 3-(3-(2-butoxyethoxy)-1,2,5-thiadiazol-4-yl)-1-methylpyridinium iodide (1.07 g, 2.5 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 490 mg. (M.p. 152°–153° C.; M$^+$: 297; Compound 41).

EXAMPLE 39

A. 3-(3-(2-(2-Butoxyethoxy)ethoxy)-1,2,5-thiadiazol-4-yl)pyridine

To a solution of 2-(2-butoxyethoxy)ethanol (1.46 g, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. 3-(3-(2-(2-Butoxyethoxy)ethoxy)-1,2,5-thiadiazol-4-yl)-1-methylpyridinium iodide A mixture of methyl iodide (0.5 ml, 9 mmol) and 3-(3-(2-(2-butoxyethoxy)ethoxy)-1,2,5-thiadiazol-4-yl)pyridine (3 mmol) in acetone (5 ml) was stirred at room temperature for 18 h. The title compound precipitated from the solution and was collected by filtration.

C. 3-(3-(2-(2-Butoxyethoxy)ethoxy)-1,2,5-thiadiazol-4-yl)-1,2,5,6-tetrahydro1-methylpyridine oxalate Sodium borohydride (230 mg, 6 mmol) was added to a solution of 3-(3-(2(2-butoxyethoxy)ethoxy)-1,2,5-thiadiazol-4-yl)-1-methylpyridinium iodide (3 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/ methanol (4:1)). The title compound was crystallized as the oxalate salt from acetone to yield 340 mg. (M.p. 90°–91° C.; M⁺: 341; Compound 42).

EXAMPLE 40

A. 3-(3-(2-(2-Ethoxyethoxy)ethoxy)-1,2,5-thiadiazol-4-yl) pyridine

To a solution of 2-(2-ethoxyethoxy)ethanol (1.21 g, 9 mmol) and sodium hydride (310 mg, 9 mmol) in dry tetrahydrofuran was added a solution of 3-(3-chloro-1,2,5-thiadiazol-4-yl)pyridine (590 mg, 3 mmol) in dry tetrahydrofuran. The reaction mixture was stirred at room temperature for 2 h. Water was added and the mixture was extracted with ether. The ether phase was dried and evaporated to give the title compound.

B. 3-(3-(2-(2-Ethoxyethoxy)ethoxy)-1,2,5-thiadiazol-4-yl)-1-methylpyridinium iodide A mixture of methyl iodide (0.5 ml, 9 mmol) and 3-(3-(2-(2-ethoxyethoxy)ethoxy)-1,2,5-thiadiazol-4-yl)pyridine (3 mmol) in acetone (5 ml) was stirred at room temperature for 18 h. The title compound precipitated from the solution and was collected by filtration.

C. 3-(3-(2-(2-Ethoxyethoxy)ethoxy)-1,2,5-thiadiazol-4-yl)-1,2,5,6-tetrahydro-1methylpyridine oxalate Sodium borohydride (230 mg, 6 mmol) was added to a solution of 3-(3-(2-(2-ethoxyethoxy)ethoxy)-1,2,5-thiadiazol-4-yl)-1-methylpyridinium iodide (3 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO₂, eluent: ethyl acetate/methanol (4:1)). The title compound was crystallized as the oxalate salt from acetone to yield 290 mg. (M.p. 115°–116° C.; M⁺: 313; Compound 43).

EXAMPLE 41

A. 3-(3-(4-Methylpiperidino)-1,2,5-thiadiazol-4-yl)pyridine

A solution of 3-(3-chloro-1,2,5-thiadiazol-4-yl)pyridine (10.80 g, 4 mmol) and 4-methylpiperidine (1.96 g, 20 mmol) in DMF (10 ml) was heated at 100° C. for 3 h. After evaporation water was added to the residue and extracted with ether. The combined and dried organic phases were evaporated and the residue purified by column chromatography (SiO₂, eluent: ethyl acetate/methylene chloride (1:2)). Yield: 0.8 g (77%).

B. 3-(3-(4-Methylpiperidino)-1,2,5-thiadiazol-4-yl)-1-methylpyridinium iodide

A mixture of methyl iodide (0.5 ml, 8 mmol) and 3-(3-(4-methylpiperidino)-1,2,5-thiadiazol-4-yl)pyridine (0.8 g, 3.1 mmol) in acetone (5 ml) was stirred at room temperature for 18 h. The title compound precipitated from the solution and was collected by filtration to yield 1.14 g (92%).

C. 3-(3-(4-Methylpiperidino)-1,2,5-thiadiazol-4-yl)-1,2,5,6-tetrahydro-1-methylpyridine oxalate Sodium borohydride (270 mg, 7 mmol) was added to a solution of 3-(3-(4-methylpiperidino)-1,2,5-thiadiazol-4-yl)-1-methylpyridinium iodide (1.14 g, 2.8 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO₂, eluent: ethyl acetate/methanol (4:1)). The title compound was crystallized as the oxalate salt from acetone to yield 450 mg. (M.p. 106°–107° C.; M⁺: 278; Compound 44).

EXAMPLE 42

A. 3-(3-Morpholino-1,2,5-thiadiazol-4-yl)pyridine

A solution of 3-(3-chloro-1,2,5-thiadiazol-4-yl)pyridine (0.59 g, 3 mmol) and morpholine (1.3 g, 15 mmol) in DMF (5 ml) was heated at 100° C. for 3 h. After evaporation water was added to the residue and extracted with ether. The combined and dried organic phases were evaporated and the residue purified by column chromatography (SiO₂, eluent: ethyl acetate/methylene chloride (1:1)). Yield: 0.68 g (91%).

B. 3-(3-Morpholino-1,2,5-thiadiazol-4-yl)-1-methylpyridinium iodide

A mixture of methyl iodide (0.5 ml, 8 mmol) and 3-(3-morpholino-1,2,5-thiadiazol-4-yl)pyridine (680 mg, 2.7 mmol) in acetone (5 ml) was stirred at room temperature for 18 h. The title compound precipitated from the solution and was collected by filtration to yield 1.0 g (94%).

C. 3-(3-Morpholino-1,2,5-thiadiazol-4-yl)-1,2,5,6-tetrahydro-1-methylpyridine oxalate Sodium borohydride (380 mg, 10 mmol) was added to a solution of 3-(3-morpholino-1,2,5-thiadiazol-4-yl)-1-methylpyridinium iodide (1.53 g, 39 mmol) in ethanol (99.9%, 30 ml) and the reaction mixture was stirred at −10° C. for 1 h. After evaporation the residue was dissolved in water and extracted with ethyl acetate. The dried organic phases were evaporated and the residue purified by column chromatography (SiO₂, eluent: ethyl acetate/methanol (4:1)). The title compound was crystallized as the oxalate salt from acetone to yield 470 mg. (M.p. 177°–178° C.; M⁺: 266; Compound 45).

EXAMPLE 43

A. 3-(3-Hexylamino-1,2,5-thiadiazol-4-yl)pyridine

A solution of 3-(3-chloro-1,2,5-thiadiazol-4-yl)pyridine (0.59 g, 3 mmol) and hexylamine (1.52 g, 15 mmol) in DMSO (5 ml) was heated at 100° C. for 48 h. After evaporation, water was added to the residue and extracted with ether. The combined organic extracts were dried and evaporated to give the title compound.

B. 3-(3-Hexylamino-1,2,5-thiadiazol-4-yl)-1-methylpyridinium iodide

A mixture of methyl iodide (0.6 ml, 9.6 mmol) and 3-(3-hexylamino-1,2,5-thiadiazol-4-yl)pyridine (3.2 mmol) in acetone (5 ml) was stirred at room temperature for 18 h and evaporated.

C. 3-(3-Hexylamino-1,2,5-thiadiazol-4-yl)-1,2,5,6-tetrahydro-1-methylpyridine oxalate Sodium borohydride (380 mg, 10 mmol) was added to a solution of 3-(3-hexylamino-1,2,5-thiadiazol-4-yl)-1-methylpyridinium iodide (4.2 mmol) in ethanol (99.9%, 25 ml) and the reaction mixture was stirred at −10° C. for 1 h. After evaporation the residue was dissolved in water and extracted with ethyl acetate. The dried organic phases were evaporated and the residue purified by column chromatography (SiO₂, eluent: ethyl acetate/methanol (4:1)). The title compound was crystallized as the oxalate salt from acetone to yield 490 mg. (M.p. 102°–103° C.; M⁺: 280; Compound 46).

EXAMPLE 44

A. 3-(3-Propylthio-1,2,5-thiadiazol-4-yl)pyridine

Sodium hydrogen sulfide (220 mg, 3 mmol) was added over 30 min. to a solution of 3-(3-chloro-1,2,5-thiadiazol-4-yl)pyridine (0.59 g, 3 mmol) in DMF (20 ml) at room temperature. Potassium carbonate (1.24 g, 9 mmol) and iodopropan (0.76 g, 4.5 mmol) were added. The reaction mixture was stirred at room temperature for 30 min. Water was added and the mixture extracted with ether. The combined ether phases were dried and evaporated to give the title compound in 89% (0.63 g) yield.

B. 3-(3-Propylthio-1,2,5-thiadiazol-4-yl)-1-methylpyridinium iodide

A mixture of methyl iodide (0.5 ml, 8 mmol) and 3-(3-propylthio-1,2,-5-thiadiazol-4-yl)pyridine (0.63 g, 2.6 mmol) in acetone (5 ml) was stirred at room temperature for 18 h and evaporated.

C. 3-(3-Propylthio-1,2,5-thiadiazol-4-yl)-1 ,2,5,6-tetrahydro-1-methylpyridine oxalate Sodium borohydride (200 mg, 5 mmol) was added to a solution of 3-(3-propylthio-1,2,5-thiadiazol-4-yl)-1-methylpyridinium iodide (2.6 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)).The title compound was crystallized as the oxalate salt from acetone to yield 310 mg. (M.p. 138°–139° C.; M$^+$: 255; Compound 47).

EXAMPLE 45

A. 3-(3-Butylthio-1,2,5-thiadiazol-4-yl)pyridine

Sodium hydrogen sulfide (0.5 g, 6.8 mmol) was added to a solution of 3-(3-chloro-1,2,5-thiadiazol-4-yl)pyridine (0.5 g, 2.5 mmol) in DMF (20 ml) at room temperature and the reaction mixture was stirred for 30 min. Potassium carbonate (2 g, 14.5 mmol) and butyl iodide (1 ml, 8.8 mmol) were added and the reaction mixture was stirred for additionally 10 min. Water (50 ml) was added and extracted with ether. The combined ether phases were dried and evaporated to give the title compound. Yield: 0.6 g.

B. 3-(3-Butylthio-1,2,5-thiadiazol-4-yl)-1-methylpyridinium iodide

Methyl iodide (1 ml, 15 mmol) was added to a solution of 3-(3-butylthio-1,2,5-thiadiazol-4-yl)pyridine (0.6 g, 2.3 mmol) and the reaction mixture was stirred at room temperature for 48 h and evaporated.

C. 3-(3-Butylthio-1,2,5-thiadiazol-4-yl)-1,2,5,6-tetrahydro-1-methylpyridine oxalate Sodium borohydride (250 mg, 6.2 mmol) was added to a solution of 3-(3-butylthio-1,2,5-thiadiazol-4-yl)-1-methylpyridinium iodide (2.3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 300 mg. (M.p. 148°–150° C.; M$^+$: 269; Compound 48).

EXAMPLE 46

A. 3-(3-Methylthio-1,2,5-thiadiazol-4-yl)pyridine

Sodium hydrogen sulfide (0.5 g, 6.8 mmol) was added to a solution of 3-(3-chloro-1,2,5-thiadiazol-4-yl)pyridine (0.5 g, 2.5 mmol) in DMF (20 ml) at room temperature and the reaction mixture was stirred for 30 min. Potassium carbonate (2 g, 14.5 mmol) and methyl iodide (1 ml, 15 mmol) were added and the reaction mixture was stirred for additionally 10 min. Water (50 ml) was added and extracted with ether. The combined ether phases were dried and evaporated to give the title compound. Yield: 0.5 g.

B. 3-(3-Methylthio-1,2,5-thiadiazol-4-yl)-1-methylpyridinium iodide

Methyl iodide (1 ml, 15 mmol) was added to a solution of 3-(3-methylthio-1,2,5-thiadiazol-4-yl)pyridine (0.5 g, 2.3 mmol) and the reaction mixture was stirred at room temperature for 48 h and evaporated.

C. 3-(3-Methylthio-1,2,5-thiadiazol-4-yl)-1,2,5,6-tetrahydro-1-methylpyridine oxalate Sodium borohydride (250 mg, 6.2 mmol) was added to a solution of 3-(3-methylthio-1,2,5-thiadiazol-4-yl)-1-methylpyridinium iodide (2.3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 300 mg. (M.p. 169°–170° C.; M$^+$: 227; Compound 49).

EXAMPLE 47

A. Alpha-oximido-3-pyridylacetonitrile 3-pyridylacetonitrile (47.2 g, 400 mmol) was dissolved in a solution of sodium hydroxide (16 g, 400 mmol) in methanol (100 ml). Methylnitrite, generated by dropping a solution of concentrated sulphuric acid (12.8 ml) and water (26 ml) to a solution of sodium nitrite (33.2 g, 480 mmol) in water (20 ml) and methanol (20 ml), was bobled through the 3-pyridylacetonitrile solution at 0° C. The reaction mixture was stirred at 0° C. for 1 h and the precipitate collected by filtration. The precipitate was washed with a little methanol to give the wanted product in 70% (41.1 g) yield. M$^+$: 147.

B. Alpha-oximido-3-pyridylacetamidoxime

A mixture of alpha-oximido-3-pyridylacetonitrile (41.0 g, 279 mmol), hydroxylamine hydrochloride (21.5 g, 310 mmol) and sodium acetate (50.8 g, 620 mmol) in ethanol (99.9%, 500 ml) was refluxed for 4 h. After cooling, the precipitate was collected by filtration and dried. The precipitate contained the wanted product and sodium acetate (85 g, 168%); M$^+$: 180.

C. 3-(3-Amino-1,2,5-oxadiazol-4-yl)pyridine

Crude alpha-oximido-3-pyridylacetamidoxime (5 g) and phosphorus pentachloride (5 g) was refluxed in dry ether (250 ml) for 6 h. Water and potassium carbonate to alkaline pH was added and the phases separated. The aqueous phase was extracted with ether and the combined ether phases dried. Evaporation of the ether phases gave the title compound in 850 mg yield; M$^+$: 162.

D. 3-(3-Amino-1,2,5-oxadiazol-4-yl)-1-methylpyridinium iodide

To a solution of 3-(3-amino-1,2,5-oxadiazol-4-yl)pyridine (870 mg, 5.3 mmol) in acetone (20 ml) was added methyl iodide (990 μl, 16 mmol) and the reaction mixture was stirred overnight at room temperature. The title compound precipitated and was collected by filtration (1.1 g, 69%).

E. 3-(3-Amino-1,2,5-oxadiazol-4-yl)-1,2,5,6-tetrahydro-1-methylpyridine oxalate

Sodium borohydride (262 mg, 6.9 mmol) was added to a solution of 3-(3-amino-1,2,5-oxadiazol-4-yl)-1-methylpyridinium iodide (1.05 g, 3.45 mmol) in methanol (80 ml) at 0° C. After 15 min. water (40 ml) was added and the mixture extracted with ether. The ether phase was dried, evaporated and purified by column chromatography (eluent: ethyl acetate:methanol (2:1)). Crystallization from acetone with oxalic acid gave the title compound in 310 mg (50%) yield. (M.p. 181°–183° C.; M$^+$: 180; Compound 50).

EXAMPLE 48

A. 3-(3-Acetylamino-1,2,5-oxadiazol-4-yl)pyridine

Crude hydroxyimino-3-pyridylmethylamidoxime (4.5 g) and polyphosphoric acid (49 g) was stirred at 100° C. for 18 h. After cooling to room temperature aqueous ammonia (25%) was added slowly to pH>9 and the precipitate collected by filtration. The precipitate was dissolved in water and extracted with methylene chloride. The organic phases were dried and evaporated to give the title compound in 430 mg yield.

B. 3-(3-Acetylamino-1,2,5-oxadiazol-4-yl)-1-methylpyridinium iodide

Methyl iodide (450 μl, 7.2 mmol) was added to a solution of 3-(3-acetylamino-1,2,5-oxadiazol-4-yl)pyridine (490 mg, 2.4 mmol) in acetone. The reaction mixture was stirred at room temperature for 18 h and the precipitate collected by filtration. Yield: 640 mg (77%).

C. 3-(3-Acetylamino-1,2,5-oxadiazol-4-yl)-1,2,5,6-tetrahydro-1-methylpyridine oxalate Sodium borohydride (140 mg, 3.7 mmol) was added to a solution of 3-(3-acetylamino-1,2,5-oxadiazol-4-yl)-1-methylpyridinium iodide (640 mg, 1.85 mmol) in methanol (15 ml) at 0° C. After 15 min. water (10 ml) was added and the reaction mixture extracted with ether. The combined ether phases were dried and evaporated. Crystallization from acetone with oxalic acid gave the title compound in 140 mg yield. (M.p. 180°–184° C.; M$^+$: 222; Compound 51).

EXAMPLE 49

A. 3-(1,2,5-Oxadiazol-3-yl)pyridine and 3-(3-chloro-1,2,5-oxadiazol-4-yl)pyridine To a solution of 3-(3-amino-1,2,5-oxadiazol-4-yl)pyridine (1.0 g, 6.2 mmol) in glacial acetic acid (16 ml) and concentrated hydrochloric acid (5.2 ml) was added CuCl$_2$ (938 mg, 7 mmol) and cupper coils (100 mg) at 0° C. After 10 min. a solution of sodium nitrite (483 mg, 7 mmol) in water (3 ml) was added dropwise at 5° C. The reaction mixture was stirred additionally 30 min. at 0° C. Aqueous sodium hydroxide (2N) was added to alkaline pH and the mixture extracted with ether. The ether phases were dried and evaporated to give a mixture of the title compounds. Separation by column chromatography (SiO$_2$, eluent: ethyl acetate) gave the chloro compound, upper spot, in 230 mg yield, and the unsubstituted product, lower spot, in 60 mg yield.

B. 3-(3-Chloro-1,2,5-oxadiazol-4-yl)-1-methylpyridinium iodide

Methyl iodide (1 ml, 15 mmol) was added to a solution of 3-(3-chloro-1,2,5-oxadiazol-4-yl)pyridine (230 mg, 1.2 mmol) in acetone. The reaction mixture was stirred at room temperature for 18 h and evaporated to give the title compound.

C. 3-(3-Chloro-1,2,5-oxadiazol-4-yl)-1,2,5,6-tetrahydro-1-methylpyridine oxalate Sodium borohydride (119 mg, 3.2 mmol) was added to a solution of 3-(3-chloro-1,2,5-oxadiazol-4-yl)-1-methylpyridinium iodide (1.2 mmol) in methanol (5 ml) at 0° C. After 15 min. water was added and the mixture extracted with ether. The ether phases were dried and evaporated. Crystallization from acetone with oxalic acid and recrystallization from acetone gave the title compound in 60 mg yield. (M.p. 126°–129° C.; M$^+$: 198 and 200; Compound 52).

EXAMPLE 50

A. 3-(1,2,5-Oxadiazol-3-yl)-1-methylpyridinium iodide

Methyl iodide (1 ml, 15 mmol) was added to a solution of 3-(1,2,5-oxadiazol-3-yl)pyridine (430 mg, 2.9 mmol) in acetone (20 ml). The reaction mixture was stirred at room temperature for 18 h. The product precipitated from the solution and the title compound was collected by filtration in 82% (700 mg) yield.

B. 3-(1,2,5-Oxadiazol-3-yl)-1,2,5,6-tetrahydro-1-methylpyridine oxalate

Sodium borohydride (168 mg, 4.4 mmol) was added to a solution of 3-(1,2,5-oxadiazol-3-yl)-1-methylpyridinium iodide (640 mg, 2.2 mmol) in methanol (15 ml) and water (2 ml) at 0° C. After 15 min. water was added and the mixture extracted with ether. The combined ether phases were dried and evaporated. The residue was crystallized as the oxalate salt from acetone giving the title compound in 100 mg yield. (M.p. 238°–240° C. dec.; M$^+$: 165; Compound 53).

EXAMPLE 51

A. 3-(3-Hexyloxy-1,2,5-oxadiazol-4-yl)pyridine

To a solution of sodium (100 mg, 4.3 mmol) in 1-hexanol (10 ml) was added 3-(3-chloro-1,2,5-oxadiazol-4-yl) pyridine (180 mg, 1 mmol). The mixture was stirred at 25° C. for 18 h and evaporated. The residue was dissolved in water and extracted with ether. The combined organic phases were dried and evaporated to give the title compound.

B. 3-(3-Hexyloxy-1,2,5-oxadiazol-4-yl)-1-methylpyridinium iodide

A mixture of methyl iodide (1 ml, 15 mmol) and 3-(3-hexyloxy-1,2,5-oxadiazol-4-yl)pyridine (1 mmol) in acetone (5 ml) was stirred at room temperature for 18 h and evaporated to give the title compound.

C. 3-(3-Hexyloxy-1,2,5-oxadiazol-4-yl)-1,2,5,6-tetrahydro-1-methylpyridine oxalate Sodium borohydride (76 mg, 2 mmol) was added to a solution of 3-(3-hexyloxy-1,2,5-oxadiazol-4-yl)-1-methylpyridinium iodide (1 mmol) in methanol (5 ml) and the reaction mixture was stirred at 0° C. for 15 min. After evaporation the residue was dissolved in water and extracted with ether. The dried organic phases were evaporated and the residue purified by column chromatography (SiO$_2$, eluent: ethyl acetate/methanol (4:1)). The title compound was crystallized as the oxalate salt from acetone to yield 60 mg. (M.p. 143°–147° C.; M$^+$: 265; Compound 54).

EXAMPLE 52

A. 3-(3-Butyloxy-1,2,5-oxadiazol-4-yl)pyridine

To a solution of sodium (150 mg, 6.5 mmol) in 1-butanol (5 ml) was added 3-(3-chloro-1,2,5-oxadiazol-4-yl)pyridine (350 mg, 1.9 mmol). The mixture was stirred at 25° C. for 2 h and evaporated. The residue was dissolved in water and extracted with ether. The combined organic phases were dried and evaporated to give the title compound.

B. 3-(3-Butyloxy-1,2,5-oxadiazol-4-yl)-1-methylpyridinium iodide

A mixture of methyl iodide (1 ml, 15 mmol) and 3-(3-butyloxy-1,2,5-oxadiazol-4-yl)pyridine (1.9 mmol) in acetone (10 ml) was stirred at room temperature for 18 h and evaporated.

C. 3-(3-Butyloxy-1,2,5-oxadiazol-4-yl)-1,2,5,6-tetrahydro-1-methylpyridine oxalate Sodium borohydride (148 mg, 3.8 mmol) was added to a solution of 3-(3-butyloxy-1,2,5-oxadiazol-4-yl)-1-methylpyridinium iodide (1.9 mmol) in methanol (20 ml) and the reaction mixture was stirred at 0° C. for 15 min. After evaporation the residue was dissolved in water and extracted with ether. The dried organic phases were evaporated and the residue purified by column chromatography (SiO$_2$, eluent: ethyl acetate/methanol (4:1)). The title compound was crystallized as the oxalate salt from acetone to yield 120 mg. (M.p. 132°–135° C.; M$^+$: 237; Compound 55).

EXAMPLE 53

A. 3-(3-(3-Hexynyloxy)-1,2,5-oxadiazol-4-yl)pyridine

To a solution of 3-hexyn-1-ol (980 mg, 10 mmol) and sodium hydride (240 mg, 10 mmol) in dry tetrahydrofuran was added a solution of 3-(3-chloro-1,2,5-oxadiazol-4-yl) pyridine (450 mg, 2.5 mmol) in dry tetrahydrofuran. The reaction mixture was stirred at room temperature for 2 h. Water was added and the mixture was extracted with ether. The ether phase was dried and evaporated to give the title compound.

B. 3-(3-(3-Hexynyloxy)-1,2,5-oxadiazol-4-yl)-1-methylpyridinium iodide

A mixture of methyl iodide (1.5 ml, 22 mmol) and 3-(3-(3-hexynyloxy)-1,2,5-oxadiazol-4-yl)pyridine (2.5 mmol) in acetone (20 ml) was stirred at room temperature for 18 h and evaporated to give the title compound.

C. 3-(3-(3-Hexynyloxy)-1,2,5-oxadiazol-4-yl)-1,2,5,6-tetrahydro-1-methylpyridine oxalate Sodium borohydride (190 mg, 5 mmol) was added to a solution of 3-(3-(3-hexynyloxy)-1,2,5-oxadiazol-4-yl)-1-methylpyridinium iodide (2.5 mmol) in methanol (20 ml) and the reaction mixture was stirred at 0° C. for 15 min. After evaporation the residue was dissolved in water and extracted with ether. The dried organic phases were evaporated and the residue purified by column chromatography (SiO₂, eluent: ethyl acetate/methanol (4:1)). The title compound was crystallized as the oxalate salt from acetone to yield 50 mg. (M.p. 159°–161° C.; M⁺: 261; Compound 56).

EXAMPLE 54

3-(3-Pentyl-1,2,5-thiadiazol-4-yl)-1,2,5,6-tetrahydro-1-methylpyridinium oxalate To a solution of 3-(3-chloro-1,2,5-thiadiazol-4-yl)-1,2,5,6-tetrahydro-1-methylpyridine (450 mg, 1.5 mmol) in tetrahydrofuran (20 ml) was added slowly a solution of pentylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was crystallized as the oxalate salt from acetone in 300 mg (58%) yield. Recrystallization from ethanol gave the title compound in 125 mg (24%) yield. (M.p. 156°–157° C.; M⁺: 251; Compound 57).

EXAMPLE 55

3-(3-Heptyl-1,2,5-thiadiazol-4-yl)-1,2,5,6-tetrahydro-1-methylpyridinium oxalate To a solution of 3-(3-chloro-1,2,5-thiadiazol-4-yl)-1,2,5,6-tetrahydro-1-methylpyridine (450 mg, 1.5 mmol) in tetrahydrofuran (20 ml) was added slowly a solution of heptylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was crystallized as the oxalate salt from acetone in 400 mg (73%) yield. (M.p. 151°–152° C.; M⁺: 274; Compound 58).

EXAMPLE 56

3-(3-(5-Hexenyl)-1,2,5-thiadiazol-4-yl)-1,2,5,6-tetrahydro-1-methylpyridinium oxalate To a solution of 3-(3-chloro-1,2,5-thiadiazol-4-yl)-1,2,5,6-tetrahydro-1-methylpyridine (450 mg, 1.5 mmol) in tetrahydrofuran (20 ml) was added slowly a solution of 5-hexenylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was purified by column chromatography (SiO₂, eluent: ethyl acetate/methanol (4:1)). The title compound was crystallized as the oxalate salt from acetone in 340 mg (64%) yield. (M.p. 113°–115° C.; M⁺: 263; Compound 59).

EXAMPLE 57

3-(3-Octyl-1,2,5-thiadiazol-4-yl)-1,2,5,6-tetrahydro-1-methylpyridinium oxalate

To a solution of 3-(3-chloro-1,2,5-thiadiazol-4-yl)-1,2,5,6-tetrahydro-1-methylpyridine (450 mg, 1.5 mmol) in tetrahydrofuran (20 ml) was added slowly a solution of octylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was purified by column chromatography (SiO₂, eluent: ethyl acetate/methanol (4:1)). The title compound was crystallized as the oxalate salt from acetone in 430 mg (75%) yield. (M.p. 157°–158° C.; M⁺: 293; Compound 60).

EXAMPLE 58

3-(3-Isobutyl-1,2,5-thiadiazol-4-yl)-1,2,5,6-tetrahydro-1-methylpyridinium oxalate To a solution of 3-(3-chloro-1,2,5-thiadiazol-4-yl)-1,2,5,6-tetrahydro-1-methylpyridine (300 mg, 1.5 mmol) in tetrahydrofuran (20 ml) was added slowly a solution of isobutylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was purified by column chromatography (SiO₂, eluent: ethyl acetate/methanol (4:1)). The title compound was crystallized as the oxalate salt from acetone in 350 mg (76%) yield. (M.p. 148°–149° C.; M⁺: 237; Compound 61).

EXAMPLE 59

3-(3-Cyclopropylmethyl-1,2,5-thiadiazol-4-yl)-1,2,5,6-tetrahydro-1-methylpyridinium oxalate To a solution of 3-(3-chloro-1,2,5-thiadiazol-4-yl)-1,2,5,6-tetrahydro-1-methylpyridine (300 mg, 1.4 mmol) in tetrahydrofuran (20 ml) was added slowly a solution of cyclopropylmethylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was purified by column chromatography (SiO₂, eluent: ethyl acetate/methanol (4:1)). The title compound was crystallized as the oxalate salt from acetone in 380 mg (83%) yield. (M.p. 147°–148° C.; M⁺: 235; Compound 62).

EXAMPLE 60

3-(3-Propyl-1,2,5-thiadiazol-4-yl)-1,2,5,6-tetrahydro-1-methylpyridinium oxalate To a solution of 3-(3-chloro-1,2,5-thiadiazol-4-yl)-1,2,5,6-tetrahydro-1-methylpyridine (450 mg, 1.5 mmol) in tetrahydrofuran (20 ml) was added slowly a solution of propylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was crystallized as the oxalate salt from acetone in 350 mg (75%) yield. (M.p. 141°–142° C.; M⁺: 223; Compound 63).

EXAMPLE 61

A. 3-(3-Octylthio-1,2,5-thiadiazol-4-yl)pyridine

Sodium hydrogen sulfide (0.25 g, 3.3 mmol) was added to a solution of 3-(3-chloro-1,2,5-thiadiazol-4-yl)pyridine (0.59 g, 3 mmol) in DMF (20 ml) at room temperature and the reaction mixture was stirred for 30 min. Potassium carbonate (1.24 g, 9 mmol) and 1-bromooctane (0.80 ml, 4.5 mmol) were added and the reaction mixture was stirred for additionally 10 min. Water (50 ml) was added and extracted with ether. The combined ether phases were dried and evaporated to give the title compound.

B. 3-(3-Octylthio-1,2,5-thiadiazol-4-yl)-1-methylpyridinium iodide

Methyl iodide (0.5 ml, 7.5 mmol) was added to a solution of 3-(3-octylthio-1,2,5-thiadiazol-4-yl)pyridine (3 mmol) and the reaction mixture was stirred at room temperature for 48 h and evaporated.

C. 3-(3-Octylthio-1,2,5-thiadiazol-4-yl)-1,2,5,6-tetrahydro-1-methylpyridine oxalate Sodium borohydride (270 mg, 7 mmol) was added to a solution of 3-(3-octylthio-1,2,5-thiadiazol-4-yl)-1-methylpyridinium iodide (3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 400 mg. (M.p. 121°–122° C.; M$^+$: 325; Compound 64).

EXAMPLE 62

A. 3-(3-Ethylthio-1,2,5-thiadiazol-4-yl)pyridine

Sodium hydrogen sulfide (0.25 g, 3.3 mmol) was added to a solution of 3-(3-chloro-1,2,5-thiadiazol-4-yl)pyridine (0.59 g, 3 mmol) in DMF (20 ml) at room temperature and the reaction mixture was stirred for 30 min. Potassium carbonate (1.24 g, 9 mmol) and ethyl iodide (0.36 ml, 4.5 mmol) were added and the reaction mixture was stirred for additionally 10 min. Water (50 ml) was added and extracted with ether. The combined ether phases were dried and evaporated to give the title compound.

B. 3-(3-Ethylthio-1,2,5-thiadiazol-4-yl)-1-methylpyridinium iodide

Methyl iodide (0.5 ml, 7.5 mmol) was added to a solution of 3-(3-ethylthio-1,2,5-thiadiazol-4-yl)pyridine (3 mmol) and the reaction mixture was stirred at room temperature for 48 h and evaporated.

C. 3-(3-Ethylthio-1,2,5-thiadiazol-4-yl)-1,2,5,6-tetrahydro-1-methylpyridine oxalate Sodium borohydride (270 mg, 7 mmol) was added to a solution of 3-(3-ethylthio-1,2,5-thiadiazol-4-yl)-1-methylpyridinium iodide (3 mmol) in ethanol (99.9%, 20 ml) and the reaction mixture was stirred at 0° C for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 490 mg. (M.p. 145°–146° C.; M$^+$: 241; Compound 65).

EXAMPLE 63

A. 3-(3-Pentylthio-1,2,5-thiadiazol-4-yl)pyridine

Sodium hydrogen sulfide (0.25 g, 3.3 mmol) was added to a solution of 3-(3-chloro-1,2,5-thiadiazol-4-yl)pyridine (0.59 g, 3 mmol) in DMF (20 ml) at room temperature and the reaction mixture was stirred for 30 min. Potassium carbonate (1.24 g, 9 mmol) and pentyl bromide (700 mg, 4.5 mmol) were added and the reaction mixture was stirred for additionally 10 min. Water (50 ml) was added and extracted with ether. The combined ether phases were dried and evaporated to give the title compound.

B. 3-(3-Pentylthio-1,2,5-thiadiazol-4-yl)-1-methylpyridinium iodide

Methyl iodide (0.5 ml, 7.5 mmol) was added to a solution of 3-(3-pentylthio-1,2,5-thiadiazol-4-yl)pyridine (3 mmol) and the reaction mixture was stirred at room temperature for 48 h and evaporated.

C. 3-(3-Pentylthio-1,2,5-thiadiazol-4-yl)-1,2,5,6-tetrahydro-1-methylpyridine oxalate Sodium borohydride (300 mg, 8 mmol) was added to a solution of 3-(3-pentylthio-1,2,5-thiadiazol-4-yl)-1-methylpyridinium iodide (3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 430 mg. (M.p. 136°–138° C.; M$^+$: 283; Compound 66).

EXAMPLE 64

A. 3-(3-Hexylthio-1,2,5-thiadiazol-4-yl)pyridine

Sodium hydrogen sulfide (0.25 g, 3.3 mmol) was added to a solution of 3-(3-chloro-1,2,5-thiadiazol-4-yl)pyridine (0.59 g, 3 mmol) in DMF (20 ml) at room temperature and the reaction mixture was stirred for 30 min. Potassium carbonate (1.24 g, 9 mmol) and hexyl bromide (0.63 ml, 4.5 mmol) were added and the reaction mixture was stirred for additionally 10 min. Water (50 ml) was added and extracted with ether. The combined ether phases were dried and evaporated to give the title compound.

B. 3-(3-Hexylthio-1,2,5-thiadiazol-4-yl)-1-methylpyridinium iodide

Methyl iodide (1 ml, 15 mmol) was added to a solution of 3-(3-hexylthio-1,2,5-thiadiazol-4-yl)pyridine (3 mmol) and the reaction mixture was stirred at room temperature for 48 h and evaporated.

C. 3-(3-Hexylthio-1,2,5-thiadiazol-4-yl)-1,2,5,6-tetrahydro-1-methylpyridine oxalate Sodium borohydride (230 mg, 6 mmol) was added to a solution of 3-(3-hexylthio-1,2,5-thiadiazol-4-yl)-1-methylpyridinium iodide (3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 350 mg. (M.p. 126°–127° C.; M$^+$: 297; Compound 67).

EXAMPLE 65

A. 3-(3-(5-Cyanopentylthio)-1,2,5-thiadiazol-4-yl)pyridine

Sodium hydrogen sulfide monohydrate (0.25 g, 3.3 mmol) was added to a solution of 3-(3-chloro-1,2,5-thiadiazol-4-yl)pyridine (0.59 g, 3.0 mmol) in DMF (20 ml) at room temperature and the reaction mixture was stirred for 1 h. Potassium carbonate (1.24 g, 9 mmol) and 6-bromocapronitrile (0.80 g, 4.5 mmol) were added and the reaction mixture was stirred for additionally 24 h. Water (50 ml) was added and extracted with ether. The combined ether phases were dried and evaporated to give the title compound.

B. 3-(3-(5-Cyanopentylthio)-1,2,5-thiadiazol-4-yl)-1-methylpyridinium iodide

Methyl iodide (1 ml, 15 mmol) was added to a solution of 3-(3-(5-cyanopentylthio)-1,2,5-thiadiazol-4-yl)pyridine (3 mmol) in acetone and the reaction mixture was stirred at room temperature for 20 h. and evaporated.

C. 3-(3-(5-Cyanopentylthio)-1,2,5-thiadiazol-4-yl)-1,2,5,6-tetrahydro-1-methylpyridine oxalate Sodium borohydride (290 mg, 7.5 mmol) was added to a solution of 3-(3-(5-cyanopentylthio)-1,2,5-thiadiazol-4-yl)-

1-methylpyridinium iodide (3 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO₂, eluent: ethyl acetate/methanol (4:1)). The title compound was crystallized as the oxalate salt from acetone to yield 410 mg. M.p. 139°–140° C. Compound 68.

The following compounds were made in exactly the same manner, starting with the appropriate alkyl halogenide:

3-(3-(3-Chloropropylthio)-1,2,5-thiadiazol-4-yl)-1,2,5,6-tetrahydro-1-methylpyridine oxalate. M.p. 136°–138° C. Compound 69.

3-(3-(3-Cyanopropylthio)-1,2,5-thiadiazol-4-yl)-1,2,5,6-tetrahydro-1-methylpyridine oxalate. M.p. 117.5°–118° C. Compound 70.

3-(3-(3-Phenylpropylthio)-1,2,5-thiadiazol-4-yl)-1,2,5,6-tetrahydro-1-methylpyridine oxalate. M.p. 110°–110.5° C. Compound 71.

3-(3-(2-Phenoxyethylthio)-1,2,5-thiadiazol-4-yl)-1,2,5,6-tetrahydro-1-methylpyridine oxalate. M.p. 125.5°–126° C. Compound 72.

3-(3-(4-Cyanobutylthio)-1,2,5-thiadiazol-4-yl)-1,2,5,6-tetrahydro-1-methylpyridine oxalate. M.p. 127°–127.5° C. Compound 73.

3-(3-(8-Hydroxyoctylthio)-1,2,5-thiadiazol-4-yl)-1,2,5,6-tetrahydro-1-methylpyridine oxalate. M.p. 112.5°–113.5° C. Compound 74.

3-(3-(4-Chlorobutylthio)-1,2,5-thiadiazol-4-yl)-1,2,5,6-tetrahydro-1-methylpyridine oxalate. M.p. 136°–137° C. Compound 75.

3-(3-(4,4-Bis-(4-fluorophenyl)-butylthio)-1,2,5-thiadiazol-4-yl)-1,2,5,6-tetrahydro-1-methylpyridine oxalate. M.p. 117.5°–118° C. Compound 76.

3-(3-(2-(1,3-Dioxolane-2-yl)-ethylthio)-1,2,5-thiadiazol-4-yl)-1,2,5,6-tetrahydro-1-methylpyridine oxalate. M.p. 117°–118° C. Compound 77.

3-(3-(4-Cyanobenzylthio)-1,2,5-thiadiazol-4-yl)-1,2,5,6-tetrahydro-1-methylpyridine oxalate. M.p. 138°–140° C. Compound 78.

3-(3-(2-Phenylethylthio)-1,2,5-thiadiazol-4-yl)-1,2,5,6-tetrahydro-1-methylpyridine oxalate. M.p. 155°–156° C. Compound 79.

3-(3-(4-Bromobenzylthio)-1,2,5-thiadiazol-4-yl)-1,2,5,6-tetrahydro-1-methylpyridine oxalate. M.p. 139°–140° C. Compound 80.

3-(3-(4-Methylbenzylthio)-1,2,5-thiadiazol-4-yl)-1,2,5,6-tetrahydro-1-methylpyridine oxalate. M.p. 162°–165° C. Compound 81.

3-(3-(4-Pyridylmethylthio)-1,2,5-thiadiazol-4-yl)-1,2,5,6-tetrahydro-1-methylpyridine oxalate. M.p. 140°–142° C. Compound 82.

3-(3-(2-Benzoylethylthio)-1,2,5-thiadiazol-4-yl)-1,2,5,6-tetrahydro-1-methylpyridine oxalate. M.p. 99°–100° C. Compound 83.

3-(3-(4-Oxo-4-(4-fluorophenyl)-butylthio)-1,2,5-thiadiazol-4-yl)-1,2,5,6-tetrahydro-1-methylpyridine oxalate. M.p. 131°–132° C. Compound 84.

3-(3-Benzyloxycarbonylmethylthio-1,2,5-thiadiazol-4-yl)-1,2,5,6-tetrahydro-1-methylpyridine oxalate. M.p. 179°–180° C. Compound 85.

3-(3-Benzylthio-1,2,5-thiadiazol-4-yl)-1,2,5,6-tetrahydro-1-methylpyridine oxalate. M.p. 195°–197° C. Compound 86.

3-(3-(4,4,4-Trifluorobutylthio)-1,2,5-thiadiazol-4-yl)-1,2,5,6-tetrahydro-1-methylpiperidine oxalate. M.p. 163°–165° C. Compound 87.

3-(3-(5,5,5-Trifluoropentylthio)-1,2,5-thiadiazol-4-yl)-1,2,5,6-tetrahydro-1-methylpyridine oxalate. M.p. 134°–136° C. Compound 88.

3-(3-(6,6,6-Trifluorohexylthio)-1,2,5-thiadiazol-4-yl)-1,2,5,6-tetrahydro-1-methylpyridine oxalate. M.p. 128°–129° C. Compound 89.

3-(3-Ethoxycarbonylpentylthio-1,2,5-thiadiazol-4-yl)-1,2,5,6-tetrahydro-1-methylpyridine oxalate. M.p. 78°–81° C. Compound 90.

3-(3-(2,2,2-Trifluoroethylthio)-1,2,5-thiadiazol-4-yl)-1,2,5,6-tetrahydro-1-methylpyridine oxalate. M.p. 159°–163° C. Compound 225.

3-(3-Isohexylthio-1,2,5-thiadiazol-4-yl)-1,2,5,6-tetrahydro-1-methylpyridine oxalate. M.p. 131°–134° C. Compound 226.

3-(3-Ethoxycarbonylpropylthio-1,2,5-thiadiazol-4-yl)-1,2,5,6-tetrahydro-1-methylpyridine hydrochloride. M.p. 109°–111° C. Compound 227.

3-(3-(2-(2-Thienylthio)ethylthio))-1,2,5-thiadiazol-4-yl)-1,2,5,6-tetrahydro-1-methylpyridineoxalate. M.p. 112°–115° C. Compound 228.

3-(3-(5-Ethyl-2-thienylmethylthio)-1,2,5-thiadiazol-4-yl)-1,2,5,6-tetrahydro-1-methylpyridine oxalate. M.p. 106°–110° C. Compound 229.

3-(3-(6-Hydroxyhexylthio)-1,2,5-thiadiazol-4-yl)-1,2,5,6-tetrahydro-1-methylpyridine oxalate. M.p. 108°–110° C. Compound 230.

3-(3-(3-Methyl-2-thienylmethylthio)-1,2,5-thiadiazol-4-yl)-1,2,5,6-tetrahydro-1-methylpyridine oxalate. M.p. 184°–186° C. Compound 231.

3-(3-(2-(2-Thienylthio)propylthio))-1,2,5-thiadiazol-4-yl)-1,2,5,6-tetrahydro-1-methylpyridine oxalate. M.p. 193°–196° C. Compound 232.

3-(3-(4-Ethoxy-1,2,5-thiadiazol-3-ylthio)-1,2,5-thiadiazol-4-yl)-1,2,5,6-tetrahydro-1-methylpyridine oxalate. M.p. 173°–174° C. Compound 233.

3-(3-(5-Methyl-2-thienylmethylthio)-1,2,5-thiadiazol-4-yl)-1,2,5,6-tetrahydro-1-methylpyridine oxalate. M.p. 148°–149° C. Compound 234.

3-(3-(4-Ethylthio-1,2,5-thiadiazol-3-ylthio)-1,2,5-thiadiazol-4-yl)-1,2,5,6-tetrahydro-1-methylpyridine oxalate. M.p. 187°–189° C. Compound 235.

3-(3-(4-Butylthio-1,2,5-thiadiazol-3-ylthio)-1,2,5-thiadiazol-4-yl)-1,2,5,6-tetrahydro-1-methylpyridine oxalate. M.p. 162°–164° C. Compound 236.

3-(3-(4-Propoxy-1,2,5-thiadiazol-3-ylthio)-1,2,5-thiadiazol-4-yl)-1,2,5,6-tetrahydro-1-methylpyridine oxalate. M.p. 182°–183° C. Compound 237.

cis 3-(3-(3-Hexenylthio)-1,2,5-thiadiazol-4-yl)-1,2,5,6-tetrahydro-1-methylpyridine oxalate. M.p. 101°–102° C. Compound 238.

3-(3-(1-Cyclopropylmethylthio)-1,2,5-thiadiazol-4-yl)-1,2,5,6-tetrahydro-1-methylpyridine oxalate. M.p. 145°–146° C. Compound 239.

3-(3-(1-Ethoxycarbonylpentylthio)-1,2,5-thiadiazol-4-yl)-1,2,5,6-tetrahydro1-methylpyridine oxalate. M.p. 94°–95° C. Compound 240.

3-(3-(5-Hexenylthio)-1,2,5-thiadiazol-4-yl)-1,2,5,6-tetrahydro-1-methylpyridine oxalate. M.p. 115°–116° C. Compound 241.

3-(3-Cyclopentylthio-1,2,5-thiadiazol-4-yl)-1,2,5,6-tetrahydro-1-methylpyridine oxalate. M.p. 144°–145° C. Compound 242.

3-(3-(2-Methoxyethylthio)-1,2,5-thiadiazol-4-yl)-1,2,5,6-tetrahydro-1-methylpyridine oxalate. M.p. 150°–151 ° C. Compound 243.

3-(3-(2-(2-Ethoxymethoxy)-ethylthio)-1,2,5-thiadiazol-4-yl)-1,2,5,6-tetrahydro1-methylpyridine oxalate. M.p. 117°–118° C. Compound 244.

3-(3-(4-Pentynylthio)-1,2,5-thiadiazol-4-yl)-1,2,5,6-tetrahydro-1-methylpyridine oxalate. M.p. 121°–122° C. Compound 245.

3-(3-Heptylthio-1,2,5-thiadiazol-4-yl)-1,2,5,6-tetrahydro-1-methylpyridine oxalate. M.p. 122°–123° C. Compound 246.

3-(3-(2-Ethylbutylthio)-1,2,5-thiadiazol-4-yl)-1,2,5,6-tetrahydro-1-methylpyridine oxalate. M.p. 141°–142° C. Compound 247.

3-(3-Cyclohexylmethylthio-1,2,5-thiadiazol-4-yl)-1,2,5,6-tetrahydro-1-methylpyridine oxalate. M.p. 153°–155° C. Compound 248.

3-(3-(7-Octenylthio)-1,2,5-thiadiazol-4-yl)-1,2,5,6-tetrahydro-1-methylpyridine oxalate. M.p. 115°–116° C. Compound 249.

3-(3-(3-Butenylthio)-1,2,5-thiadiazol-4-yl)-1,2,5,6-tetrahydro-1-methylpyridine oxalate. M.p. 140°–141° C. Compound 250.

3-(3-(4-Pentenylthio)-1,2,5-thiadiazol-4-yl)-1,2,5,6-tetrahydro-1-methylpyridine oxalate. M.p. 137°–138° C. Compound 251.

3-(3-(3,3,3-Trifluoropropylthio)-1,2,5-thiadiazol-4-yl)-1,2,5,6-tetrahydro-1-methylpyridine oxalate. M.p. 131°–135° C. Compound 252.

3-(3-(1-Oxo-1-phenylpropylthio-1,2,5-thiadiazol-4-yl)-1,2,5,6-tetrahydro-1-methylpyridine oxalate. M.p. 99°–100° C. Compound 253.

3-(3-(4-Phenylthiobutylthio)-1,2,5-thiadiazol-4-yl)-1,2,5,6-tetrahydro-1-methylpyridine oxalate. M.p. 97°–99° C. Compound 254.

3-(3-Cyanomethylthio-1,2,5-thiadiazol-4-yl)-1,2,5,6-tetrahydro-1-methylpyridine oxalate. M.p. 176°–177° C. Compound 255.

3-(3-(6-Chlorohexylthio)-1,2,5-thiadiazol-4-yl)-1,2,5,6-tetrahydro-1-methylpyridine oxalate. M.p. 125°–126° C. Compound 256.

3-(3-(5-Chloropentylthio)-1,2,5-thiadiazol-4-yl)-1,2,5,6-tetrahydro-1-methylpyridine oxalate. M.p. 106°–107° C. Compound 257.

EXAMPLE 66

A. 3-(3-(6,6,6-Trifluorohexyloxy-1,2,5-thiadiazol-4-yl)pyridine

To a mixture of sodium hydride (12.8 mmol) and 6,6,6-trifluoro-1-hexanol (3.0 g, 19.2 mmol) in tetrahydrofuran (40 ml) was added 3-(3-chloro-1,2,5-thiadiazol-4-yl)pyridine (1.3 g, 6.4 mmol). The mixture was refluxed for 36 h. and evaporated. After evaporation the residue was dissolved in water then extracted with diethyl ether. The dried organic phases were evaporated and the residue purified by column chromatography (silica gel, eluent: ethyl acetate/hexanes) to yield 630 mg (31%) of the title compound.

B. 3-(3-(6,6,6-Trifluorohexyloxy-1,2,5-thiadiazol-4-yl)-1-methylpyridinium iodide A solution of methyl iodide (852 mg, 6.0 mmol) and 3-(3-(6,6,6-trifluorohexyloxy-1,2,5-thiadiazol-4-yl)pyridine (630 mg, 2.0 mmol) in acetone (25 ml) was refluxed for 7 h. The solution was evaporated and the residue was used directly in the next step.

C. 1,2,5,6-Tetrahydro-1-methyl-3-(3-(6,6,6-trifluorohexyloxy)-1,2,5-thiadiazol-4-yl)pyridine oxalate Sodium borohydride (380 mg, 10 mmol) was added to a solution of 3-(3-(6,6,6-trifluorohexyloxy-1,2,5-thiadiazol-4-yl)-1-methylpyridinium iodide (2.0 mmol) in ethanol (15 ml) and the reaction mixture was stirred at room temperature overnight. After evaporation the residue was dissolved in water and extracted with diethyl ether. The dried organic phases were evaporated and the residue was purified by column chromatography (silica gel, eluent: 25% ethyl acetate in hexanes). The title compound was crystallized as the oxalate salt from acetone to yield 180 mg (21%) M.p. 138°–140° C. Theoretical %C=45.17, %H=5.21, %N=9.88. Found %C=45.13, %H=5.18, %N=9.62. Compound 91.

The following compounds were made in exactly the same manner using the appropriate alkoxy derivative:

1,2,5,6-Tetrahydro-1-methyl-3-(3-(3-(2-thienyl)-1-propoxy)-1,2,5-thiadiazol-4-yl)pyridine oxalate M.p. 130°–133° C., $M^+$: 321. Compound 92.

1,2,5,6-Tetrahydro-1-methyl-3-(3-(3-(4-methoxyphenyl)-1-propoxy)-1,2,5-thiadiazol-4-yl)pyridine oxalate M.p. 166°–167° C., $M^+$: 345. Compound 93.

1,2,5,6-Tetrahydro-1-methyl-3-(3-(2-(4-methoxyphenyl)-1-ethoxy)-1,2,5-thiadiazol-4-yl)pyridine oxalate M.p. 166°–167° C., $M^+$: 331. Compound 94.

1,2,5,6-Tetrahydro-1-methyl-3-(3-(2-(2-thienyl)-1-ethoxy)-1,2,5-thiadiazol-4-yl)pyridine oxalate. M.p. 145°–146° C., $M^+$: 306. Compound 95.

1,2,5,6-Tetrahydro-1-methyl-3-(3-(2-(3-thienyl)-1-ethoxy)-1,2,5-thiadiazol-4-yl)pyridine oxalate. M.p. 138°–140° C., $M^+$: 306. Compound 96.

1,2,5,6-Tetrahydro-1-methyl-3-(3-(3-hydroxy-1-propoxy)-1,2,5-thiadiazol-4-yl)pyridine oxalate. M.p. 105°–107° C., $M^+$: 256. Compound 97.

1,2,5,6-Tetrahydro-1-methyl-3-(3-(2-phenyl-1-ethoxy)-1,2,5-thiadiazol-4-yl)pyridine oxalate. M.p. 146°–147° C., $M^+$: 301. Compound 98.

1,2,5,6-Tetrahydro-1-methyl-3-(3-(2-thienylmethoxy)-1,2,5-thiadiazol-4-yl)pyridine oxalate. M.p. 161°–162° C., $M^+$: 294. Compound 99.

1,2,5,6-Tetrahydro-1-methyl-3-(3-(3-hydroxy-1-hexyloxy)-1,2,5-thiadiazol-4-yl)pyridine oxalate. M.p. 147°–148° C., $M^+$: 297. Compound 100.

1,2,5,6-Tetrahydro-1-methyl-3-(3-(3-thienylmethoxy)-1,2,5-thiadiazol-4-yl)pyridine oxalate. M.p. 175°–176° C., $M^+$: 293. Compound 101.

1,2,5,6-Tetrahydro-1-methyl-3-(3-(3-phenyl-1-propoxy)-1,2,5-thiadiazol-4-yl)pyridine oxalate. M.p. 136°–138° C., $M^+$: 315. Compound 102.

1,2,5,6-Tetrahydro-1-methyl-3-(3-(3-(2-pyrrolidon-1-yl)-1-propoxy)-1,2,5-thiadiazol-4-yl)pyridine oxalate. M.p. 160°–161° C., $M^+$: 322. Compound 103.

1,2,5,6-Tetrahydro-1-methyl-3-(3-(6-acetamido-1-hexyloxy)-1,2,5-thiadiazol-4-yl)pyridine oxalate. M.p. 114°–116° C., $M^+$: 338. Compound 104.

1,2,5,6-Tetrahydro-1-methyl-3-(3-(2-acetamido-1-ethoxy)-1,2,5-thiadiazol-4-yl)pyridine oxalate. M.p. 145°–148° C., $M^+$: 283. Compound 105.

1,2,5,6-Tetrahydro-1-methyl-3-(3-(2-(2-pyrrolidon-1-yl)-1-ethoxy)-1,2,5-thiadiazol-4-yl)pyridine oxalate. M.p. 170°–171° C., $M^+$: 309. Compound 106.

1,2,5,6-Tetrahydro-1-methyl-3-(3-(2-propionamido-1-ethoxy)-1,2,5-thiadiazol-4-yl)pyridine oxalate. M.p. 142°–143° C., $M^+$: 296. Compound 107.

1,2,5,6-Tetrahydro-1-methyl-3-(3-(2-(2-oxazolidon-3-yl)-1-ethoxy)-1,2,5-thiadiazol-4-yl)pyridine oxalate. M.p. 157°–159° C., $M^+$: 310. Compound 108.

1,2,5,6-Tetrahydro-1-methyl-3-(3-(2-benzylthio-1-ethoxy)-1,2,5-thiadiazol-4-yl)pyridine oxalate. M.p. 133°–134° C., $M^+$: 347. Compound 109.

1,2,5,6-Tetrahydro-1-methyl-3-(3-(3-(1-pyrrolidyl)-1-propoxy)-1,2,5-thiadiazol-4-yl)pyridine oxalate. M.p. 141°–142° C., $M^+$: 308. Compound 110.

1,2,5,6-Tetrahydro-1-methyl-3-(3-(2-ureido-1-ethoxy)-1,2,5-thiadiazol-4-yl)pyridine oxalate. M.p. 200° C. (decompose), $M^+$: 265. Compound 111.

3-(3-(2,4-Dimethylphenylpropoxy)-1,2,5-thiadiazol-4-yl)-1,2,5,6-tetrahydrol-methylpyridine oxalate from 3-(3-chloro-1,2,5-thiadiazol-4-yl)pyridine and 1-(2,4-dimethylphenyl)-3-propanol. M.p. 159°–162° C. Compound 161.

3-(3-(3,4-Dimethylphenylpropoxy)-1,2,5-thiadiazol-4-yl)-1,2,5,6-tetrahydro-1methylpyridine oxalate from 3-(3-chloro-1,2,5-thiadiazol-4-yl)pyridine and 1-(3,4-dimethylphenyl)-3-propanol. M.p. 119°–121° C. Compound 162.

3-(3-(5-Ethyl-2-thienylmethoxy)-1,2,5-thiadiazol-4-yl)-1,2,5,6-tetrahydro-1-methylpyridine oxalate from 3-(3-chloro-1,2,5-thiadiazol-4-yl)pyridine and 1-hydroxymethyl-5-ethylthiophene. M.p. 146°–148° C. Compound 163.

3-(3-(Pyrrolidin-1-yl)propoxy-1,2,5-thiadiazol-4-yl)-1,2,5,6-tetrahydro-1-methylpyridine dioxalate from 3-(3-chloro-1,2,5-thiadiazol-4-yl)pyridine and 1-pyrrolidin-1-yl-3-propanol. M.p. 141° C. decomp. Compound 164.

3-(3-(4-Fluorophenylpropoxy)-1,2,5-thiadiazol-4-yl)-1,2,5,6-tetrahydro-1-methylpyridine oxalate from 3-(3-chloro-1,2,5-thiadiazol-4-yl)pyridine and 1-(4-fluorophenyl)-3-propanol. M.p. 143°–146° C. Compound 165.

3-(3-(4-Chlorophenylpropoxy)-1,2,5-thiadiazol-4-yl)-1,2,5,6-tetrahydro-1-methylpyridine oxalate from 3-(3-chloro-1,2,5-thiadiazol-4-yl)pyridine and 1-(4-chlorophenyl)-3-propanol. M.p. 154°–155° C. Compound 166.

3-(3-(3-Methylphenylpropoxy)-1,2,5-thiadiazol-4-yl)-1,2,5,6-tetrahydro-1-methylpyridine oxalate from 3-(3-chloro-1,2,5-thiadiazol-4-yl)pyridine and 1-(3methylphenyl)-3-propanol. M.p 138°–1390. Compound 167.

3-(3-(2,3-Dihydro-1-indenyloxy)-1,2,5-thiadiazol-4-yl)-1,2,5,6-tetrahydro-1-methylpyridine oxalate from 3-(3-chloro-1,2,5-thiadiazol-4-yl)pyridine and 1-hydroxy-2,3-dihydroindene. M.p. 157°–159° C. Compound 168.

3-(3-(4-Methylphenylpropoxy)-1,2,5-thiadiazol-4-yl)-1,2,5,6-tetrahydro-1-methylpyridine oxalate from 3-(3-chloro-1,2,5-thiadiazol-4-yl)pyridine and 1-(4-methylphenyl)-3-propanol. M.p. 155°–159° C. Compound 169.

3-(3-(1,2,3,4-Tetrahydro-2-naphtalyloxy)-1,2,5-thiadiazol-4-yl)-1,2,5,6-tetrahydro-1-methylpyridine oxalate from 3-(3-chloro-1,2,5-thiadiazol-4-yl)pyridine and 1,2,3,4-tetrahydro-2-naphthol. M.p. 100°–103°. Compound 170.

3-(3-Phenylbutoxy-1,2,5-thiadiazol-4-yl)-1,2,5,6-tetrahydro-1-methylpyridine oxalate from 3-(3-chloro-1,2,5-thiadiazol-4-yl)pyridine and-1-phenyl-4-butanol. M.p. 128°–130° C. Compound 171.

3-(3-(2-Methylphenylpropoxy)-1,2,5-thiadiazol-4-yl)-1,2,5,6-tetrahydro-1-methylpyridine oxalate from 3-(3-chloro-1,2,5-thiadiazol-4-yl)pyridine and 1-(2-methylphenyl)-3-propanol. M.p. 145°–148°. Compound 172.

3-(3-(2,5-Dimethylphenylpropoxy)-1,2,5-thiadiazol-4-yl)-1,2,5,6-tetrahydro-1-methylpyridine oxalate from 3-(3-chloro-1,2,5-thiadiazol-4-yl)pyridine and 1-(2,5-dimethylphenyl)-3-propanol. M.p. 130°–134° C. Compound 173.

3-(3-Methylthioethoxy-1,2,5-thiadiazol-4-yl)-1,2,5,6-tetrahydro-1-methylpyridine oxalate from 3-(3-chloro-1,2,5-thiadiazol-4-yl)pyridine and methylthioethanol. M.p. 146°–147° C. Compound 174.

3-(3-Dimethylaminoethoxy-1,2,5-thiadiazol-4-yl)-1,2,5,6-tetrahydro-1-methylpyridine dioxalate from 3-(3-chloro-1,2,5-thiadiazol-4-yl)pyridine and dimethylaminoethanol. M.p. 148°–150° C. Compound 175.

3-(3-(3,4-Dichlorophenylpropoxy)-1,2,5-thiadiazol-4-yl)-1,2,5,6-tetrahydro-1-methylpyridine oxalate from 3-(3-chloro-1,2,5-thiadiazol-4-yl)pyridine and 1-(3,4-dichlorophenyl)-3-propanol. M.p. 149°–151° C. Compound 176.

3-(3-Dimethylaminopropoxy-1,2,5-thiadiazol-4-yl)-1,2,5,6-tetrahydro-1-methylpyridine dioxalate from 3-(3-chloro-1,2,5-thiadiazol-4-yl)pyridine and 1-dimethylamino-3-propanol. M.p. 144°–146° C. Compound 177.

3-(3-(4-Ethylbenzyloxy)-1,2,5-thiadiazol-4-yl)-1,2,5,6-tetrahydro-1-methylpyridine oxalate from 3-(3-chloro-1,2,5-thiadiazol-4-yl)pyridine and 1-ethyl-4hydroxymethylbenzene. M.p. 187°–190° C. Compound 178.

3-(3-(4-Methylphenylpropoxy)-1,2,5-thiadiazol-4-yl)-1,2,5,6-tetrahydro-1-methylpyridine oxalate from 3-(3-chloro-1,2,5-thiadiazol-4-yl)pyridine and 1-(4-methylphenyl)-3-propanol. M.p. 147°–149° C. Compound 179.

3-(3-(4-Butylbenzyloxy)-1,2,5-thiadiazol-4-yl)-1,2,5,6-tetrahydro-1-methylpyridine oxalate from 3-(3-chloro-1,2,5-thiadiazol-4-yl)pyridine and 1-butyl-4-hydroxymethylbenzene. M.p. 187°–190° C. Compound 180.

3-(3-(1-Ethylpentyloxy)-1,2,5-thiadiazol-4-yl)-1,2,5,6-tetrahydro-1-methylpyridine fumarate from 3-(3-chloro-1,2,5-thiadiazol-4-yl)pyridine and 3-octanol. M.p. 117°–120° C. Compound 181.

3-(3-(1-Ethylbutoxy)-1,2,5-thiadiazol-4-yl)-1,2,5,6-tetrahydro-1-methylpyridine fumarate from 3-(3-chloro-1,2,5-thiadiazol-4-yl)pyridine and 3-heptanol. M.p. 139°–140° C. Compound 182.

3-(3-(1-Methylpentyloxy)-1,2,5-thiadiazol-4-yl)-1,2,5,6-tetrahydro-1-methylpyridine fumarate from 3-(3-chloro-1,2,5-thiadiazol-4-yl)pyridine and 2-hexanol. M.p. 143°–144° C. Compound 183.

3-(3-(5-Hexynyloxy)-1,2,5-thiadiazol-4-yl)-1,2,5,6-tetrahydro-1-methylpyridine oxalate from 3-(3-chloro-1,2,5-thiadiazol-4-yl)pyridine and 6-hydroxy-1-hexyne. M.p. 120°–122° C. Compound 184.

3-(3-(4-Cyclohexylbutoxy)-1,2,5-thiadiazol-4-yl)-1,2,5,6-tetrahydro-1-methylpyridine oxalate from 3-(3-chloro-1,2,5-thiadiazol-4-yl)pyridine and 1-cyclohexyl-4-butanol. M.p. 145°–147° C. Compound 185.

3-(3-(5-Hydroxyhexyloxy)-1,2,5-thiadiazol-4-yl)-1,2,5,6-tetrahydro-1-methylpyridine oxalate from 3-(3-chloro-1,2,5-thiadiazol-4-yl)pyridine and 1,5-dihydroxyhexane. M.p. 128°–129° C. Compound 186.

3-(3-(5-Oxyhexyloxy)-1,2,5-thiadiazol-4-yl)-1,2,5,6-tetrahydro-1-methylpyridine oxalate from 3-(3-chloro-1,2,5-thiadiazol-4-yl)pyridine and 5-oxo-1-hexanol. M.p. 143°–144° C. Compound 187.

3-(3-(3-Methyl-4-pentenyloxy)-1,2,5-thiadiazol-4-yl)-1,2,5,6-tetrahydro-1-methylpyridine oxalate from 3-(3-chloro-1,2,5-thiadiazol-4-yl)pyridine and 1-hydroxy-3-methyl-4-penten. M.p. 150°–151° C. Compound 188.

3-(3-(4-Methylenecyclohexylmethyl)-1,2,5-thiadiazol-4-yl)-1,2,5,6-tetrahydro-1-methylpyridine oxalate from 3-(3-chloro-1,2,5-thiadiazol-4-yl)pyridine and 1-hydroxymethyl-4-methylenecyclohexan. M.p. 160°–161° C. Compound 189.

3-(3-(2,3-Dimethylpentyloxy)-1,2,5-thiadiazol-4-yl)-1,2,5,6-tetrahydro-1-methylpyridine oxalate from 3-(3-chloro-1,2,5-thiadiazol-4-yl)pyridine and 1-hydroxy-2,3-dimethylpentan. M.p. 160°–161° C. Compound 190.

3-(3-(3-Cyclohexenylmethoxy)-1,2,5-thiadiazol-4-yl)-1,2,5,6-tetrahydro-1-methylpyridine oxalate from 3-(3-chloro-1,2,5-thiadiazol-4-yl)pyridine and 1-hydroxymethyl-3-cyclohexen. M.p. 138°–140° C. Compound 191.

3-(3-Isobutylthioethoxy-1,2,5-thiadiazol-4-yl)-1,2,5,6-tetrahydro-1-methylpyridine oxalate from 3-(3-chloro-1, 2,5-thiadiazol-4-yl)pyridine and isobutylthioethanol. M.p. 138°–140° C. Compound 192.

3-(3-Cyclopropylpropoxy-1,2,5-thiadiazol-4-yl)-1,2,5,6-tetrahydro-1-methylpyridine oxalate from 3-(3-chloro-1,2,5-thiadiazol-4-yl)pyridine and 1-cyclopropyl-3-propanol. M.p. 151°–153° C. Compound 193.

3-(3-(2-Methylcyclopropylmethoxy)-1,2,5-thiadiazol-4-yl)-1,2,5,6-tetrahydro1-methylpyridine oxalate from 3-(3-chloro-1,2,5-thiadiazol-4-yl)pyridine and 1-hydroxymethyl-2-methylcyclopropan. Mp 121°–122° C. Compound 194.

3-(3-Cyclopentylpropyloxy-1,2,5-thiadiazol-4-yl)-1,2,5,6-tetrahydro-1-methylpyridine oxalate from 3-(3-chloro-1,2,5-thiadiazol-4-yl)pyridine and 1-cyclopentyl-3-propanol. M.p. 154°–156° C. Compound 195.

3-(3-(4-Methylhexyloxy)-1,2,5-thiadiazol-4-yl)-1,2,5,6-tetrahydro-1-methylpyridine oxalate from 3-(3-chloro-1,2,5-thiadiazol-4-yl)pyridine and 4-methyl-1hexanol. M.p. 136°–139° C. Compound 196.

3-(3-(1-Methylhexyloxy)-1,2,5-thiadiazol-4-yl)-1,2,5,6-tetrahydro-1-methylpyridine oxalate from 3-(3-chloro-1,2,5-thiadiazol-4-yl)pyridine and 2-heptanol. M.p. 118°–119° C. Compound 197.

3-(3-(4,4,4-Trifluorobutoxy)-1,2,5-thiadiazol-4-yl)-1,2,5,6-tetrahydro-1-methylpyridine oxalate from 3-(3-chloro-1,2,5-thiadiazol-4-yl)pyridine and 4,4,4trifluoro-1-butanol. M.p. 157°–160° C. Compound 198.

3-(3-(3-Methylpentyloxy)-1,2,5-thiadiazol-4-yl)-1,2,5,6-tetrahydro-1-methylpyridine fumarate from 3-(3-chloro-1,2,5-thiadiazol-4-yl)pyridine and 3-methyl-1-pentanol. M.p. 133°–134° C. Compound 199.

3-(3-(6,6,6-Trifluorohexyloxy)-1,2,5-thiadiazol-4-yl)-1,2,5,6-tetrahydro-1-methylpyridine oxalate from 3-(3-chloro-1,2,5-thiadiazol-4-yl)pyridine and 6,6,6-trifluoro-1-hexanol. M.p. 144°–146° C. Compound 200.

3-(3-(3-Cyclobutylpropoxy)-1,2,5-thiadiazol-4-yl)-1,2,5,6-tetrahydro-1-methylpyridine oxalate from 3-(3-chloro-1,2,5-thiadiazol-4-yl)pyridine and 3-cyclobutyl-1-propanol. M.p. 146°–148° C. Compound 201.

3-(3-Isopropoxyethoxy-1,2,5-thiadiazol-4-yl)-1,2,5,6-tetrahydro-1-methylpyridine oxalate from 3-(3-chloro-1,2,5-thiadiazol-4-yl)pyridine and isopropoxyethanol. M.p. 142°–143° C. Compound 202.

3-(3-Isoheptyloxy-1,2,5-thiadiazol-4-yl)-1,2,5,6-tetrahydro-1-methylpyridine oxalate from 3-(3-chloro-1,2,5-thiadiazol-4-yl)pyridine and isoheptanol. M.p. 150°–152° C. Compound 203.

3-(3-Isohexyloxy-1,2,5-thiadiazol-4-yl)-1,2,5,6-tetrahydro-1-methylpyridine maleate from 3-(3-chloro-1,2,5-thiadiazol-4-yl)pyridine and isohexanol. M.p. 72°–74° C. Compound 204.

3-(3-(2,2,2-Trifluoroethoxy)-1,2,5-thiadiazol-4-yl)-1,2,5,6-tetrahydro-1-methylpyridine fumarate from 3-(3-chloro-1,2,5-thiadiazol-4-yl)pyridine and 2,2,2-trifluoroethanol. M.p. 131°–133° C. Compound 205.

3-(3-(2-Chlorophenylpropoxy-1,2,5-thiadiazol-4-yl)-1,2,5,6-tetrahydro-1-methylpyridine oxalate from 3-(3-chloro-1,2,5-thiadiazol-4-yl)pyridine and 1-(2-chlorophenyl)-3-propanol. M.p. 147°–149° C. Compound 206.

3-(3-(3-Cyclohexylpropoxy)-1,2,5-thiadiazol-4-yl)-1,2,5,6-tetrahydro-1-methylpyridine fumarate from 3-(3-chloro-1,2,5-thiadiazol-4-yl)pyridine and 1-cyclopropyl-3-propanol. M.p. 89°–90° C. Compound 207.

3-(3-(2-Cyclohexylethoxy)-1,2,5-thiadiazol-4-yl)-1,2,5,6-tetrahydro-1-methylpyridine oxalate from 3-(3-chloro-1,2,5-thiadiazol-4-yl)pyridine and 2-cyclopropylethanol. M.p. 134°–135° C. Compound 208.

1,2,5,6-Tetrahydro-1-methyl-3-(3-(2-ethylsulfinyl-1-ethoxy)-1,2,5-thiadiazol-4-yl)pyridine oxalate 1,2,5,6-tetrahydro-1-methyl-3-(3-(2-ethylsulfinyl-1-ethoxy)-1,2,5-thiadiazol-4-yl)pyridine oxalate was prepared in the same manner using 2-(ethylthio)ethanol as the starting alcohol. The intermediate 3-(4-(2-ethylthio-1-ethoxy)-1,2,5-thiadiazol-3-yl)pyridine was oxidized with 1.1 equivalent of $NaIO_4$ and 1 equivalent $MeSO_3H$ using water as the reaction solvent. After a reaction time of 3.5 h. the solution was made basic with 2N NaOH and extracted with ethyl acetate. The combined extracts were dried over $MgSO_4$ and evaporated under vacuum. The resulting sulfoxide was then converted to the title compound in the same manner described above. M.p. 171°–172° C., $M^+$: 302. Compound 112.

1,2,5,6-Tetrahydro-3-(3-(5-oxohexyl)-1,2,5-thiadiazol-4-yl)-1-methylpyridine 1,2,5,6-tetrahydro-3-(3-(5-hydroxyhexyl)-1,2,5-thiadiazol-4-yl)-1-methylpyridine was prepared in the same manner using 1,5-hexanediol. Oxidation of this compound to the named ketone was carried out under conditions as follows. To a –70° C. solution of oxalylchloride (420 µl, 4.8 mmol) in 25 ml $CH_2Cl_2$ was added DMSO (750 µl, 10.6 mmol) at a rate so as to maintain the reaction temperature below –45° C. Two min. after the addition 1,2,5,6-tetrahydro-3-(3-(5-hydroxyhexyl)-1,2,5-thiadiazol-4-yl)-1-methylpyridine (1.3 g, 4.4 mmol) in 20 ml $CH_2Cl_2$ was added slowly, keeping the temperature below –45° C. After 15 min. $Et_3N$ (3 ml, 21.8 mmol) was added and the reaction was warmed to room temperature. Brine (50 ml) was added and the mixture was extracted three times with 50 ml $CH_2Cl_2$. The combined extracts were dried over $Na_2SO_4$ and evaporated under vacuum. The resulting oil was chromatographed on silica gel (90% $CHCl_3$, 2% MeOH as eluent), affording 810 mg of an oil, which was dissolved in MeOH and treated with oxalic acid (250 mg, 2.8 mmol). The resulting oxalate salt was recrystallized from MeOH/EtOAc, affording 860 mg. M.p. 143°–144° C., $M^+$: 295. Compound 113.

EXAMPLE 67

A. 3-(3-Chloro-1,2,5-oxadiazol-4-yl)pyridine

To a solution of 3-(3-amino-1,2,5-oxadiazol-4-yl)pyridine (1.0 g, 6.2 mmol) in glacial acetic acid (16 ml) and concentrated hydrochloric acid (5.2 ml) was added $CuCl_2$ (938 mg, 7 mmol) and copper coils (100 mg) at 0° C. After 10 min. a solution of sodium nitrite (483 mg, 7 mmol) in water (3 ml) was added dropwise at 5° C. The reaction mixture was stirred additionally 30 min. at 0° C. Aqueous sodium hydroxide (2N) was added to alkaline pH and the mixture extracted with ether. The ether phases were dried and evaporated to give a mixture of the title compounds. Separation by column chromatography ($SiO_2$, eluent: ethyl acetate) gave the chloro compound, upper spot, in 230 mg yield.

B. 3-(3-(3-Phenylpropylthio)-1,2,5-oxadiazol-4-yl)pyridine

Sodium hydrogen sulfide monohydrate (0.74 g, 10.5 mmol) was added to a solution of 3-(3-chloro-1,2,5-oxadiazol-4-yl)pyridine (1.27, 7.0 mmol) in DMF (30 ml) at room temperature and the reaction mixture was stirred for 1 h. Potassium carbonate (2.0 g, 14.5 mmol) and 1-bromo-3-phenylpropane (2.4 g, 12 mmol) were added and the reaction mixture was stirred for additionally 24 h. Water (50 ml) was added and extracted with ether. The combined ether phases were dried and evaporated. Purification by column chromatography ($SiO_2$, eluent: ethyl acetate/methylene chloride (1:1)) gave the title compound.

C. 3-(3-(3-Phenylpropylthio)-1,2,5-oxadiazol-4-yl)-1-methylpyridinium iodide

Methyl iodide (1 ml, 15 mmol) was added to a solution of 3-(3-(3-phenylpropylthio)-1,2,5-oxadiazol-4-yl)pyridine (7 mmol) in acetone and the reaction mixture was stirred at room temperature for 20 h. and evaporated.

D. 3-(3-(3-Phenylpropylthio)-1,2,5-oxadiazol-4-yl)-1,2,5,6-tetrahydro-1-methylpyridine oxalate Sodium borohydride (650 mg, 17 mmol) was added to a solution of 3-(3-(3-phenylpropylthio)-1,2,5-oxadiazol-4-yl)-1-methylpyridinum iodide (7 mmol), in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography ($SiO_2$, eluent: ethyl acetate/methanol (4:1)). The title compound was crystallized as the oxalate salt from acetone and recrystallized to yield 170 mg. M.p. 106°–108° C. Compound 114.

The following compound was made in exactly the same manner using the appropriate alkylhalogenide:

3-(3-(2-Phenoxyethylthio)-1,2,5-oxadiazol-4-yl)-1,2,5,6-tetrahydro-1-methylpyridine oxalate. M.p. 122°–124° C. Compound 115.

3-(3-Pentylthio-1,2,5-oxadiazol-4-yl)-1,2,5,6-tetrahydro-1-methylpyridine oxalate from 3-(3-chloro-1,2,5-oxadiazol-4-yl)pyridine, sodium hydrogensulfide and 1-bromopentane. M.p. 123°–124° C. Compound 212.

3-(3-Hexylthio-1,2,5-oxadiazol-4-yl)-1,2,5,6-tetrahydro-1-methylpyridine oxalate from 3-(3-chloro-1,2,5-oxadiazol-4-yl)pyridine, sodium hydrogensulfide and 1-bromohexane. M.p. 111°–113° C. Compound 213.

3-(3-(4-Pentynylthio)-1,2,5-oxadiazol-4-yl)-1,2,5,6-tetrahydro-1-methylpyridine oxalate from 3-(3-chloro-1,2,5-oxadiazol-4-yl)pyridine, sodium hydrogensulfide and 1-bromo-4-pentyne. M.p. 119°–120° C. Compound 214.

EXAMPLE 68

1-(3-(3-Pyridyl)-1,2,5-thiadiazol-4-ylthio)-4-(3-(1-methyl-1,2,5,6-tetrahydropyridin-3-yl)-1,2,5-thiadiazol-4-ylthio)butane oxalate To a solution of 3-(3-chloro-1,2,5-thiadiazol-4-yl)-1-methyl-1,2,5,6-tetrahydropyridine (0.43 g, 2 mmol) in DMF (30 ml) was added sodium-hydrogensulfide (0.3 g, 4 mmol). The reaction mixture was stirred at room temperature for 1 h. Potassium carbonate (1 g) and 3-(3-(4-chlorobutylthio)-1,2,5-thiadiazol-4-yl)pyridine were added and the reaction mixture stirred at room temperature overnight. Water (200 ml) was added and the water phase extracted with ether (3×100 ml). The ether extracts were dried over magnesium sulfate and evaporated. The residue was purified by column chromatography (eluent: ethyl acetate/methanol 9:1). The free base obtained was crystallized with oxalic acid from acetone in 0.9 g yield. (Compound 116). M.p. 127°–129° C.

EXAMPLE 69

1-(1-Methyltetrazol-5-ylthio)-4-(3-(1-methyl-1,2,5,6-tetrahydropyridin-3-yl)1,2,5-thiadiazol-4-ylthio)butane oxalate To a solution of 3-(3-(4-chlorobutylthio)-1,2,5-thiadiazol-4-yl)-1-methyl-1,2,5,6-tetrahydropyridine (0.30 g, 1 mmol) in DMF (30 ml) were added 1-methyl-5-mercaptotetrazol (0.35 g, 3 mmol) and potassium carbonate (2 g). The reaction mixture was stirred at room temperature for 60 h.

1N hydrochloric acid was added (200 ml) and the water phase was extracted with ether (2×100 ml). The water phase was basified with solid potassium carbonate and extracted with ether (3×100 ml). The ether extracts from the alkaline extractions were combined and dried over magnesium sulfate. The ether phase was evaporated and the residue was crystallized with oxalic acid from acetone giving the title compound in 0.4 g yield. (Compound 117). M.p. 77°–79° C.

EXAMPLE 70

The following compounds were made in exactly the same manner as described in example 69 by using the reagents indicated.

1-(2-Methyl-1,3,4-thiadiazol-5-ylthio)-4-(3-(1-methyl-1,2,5,6-tetrahydropyridin-3-yl)-1,2,5-thiadiazol-4-ylthio)butane oxalate from 3-(3-(4-chlorobutylthio)-1,2,5-thiadiazol-4-yl)-1-methyl-1,2,5,6-tetrahydropyridine and 2-methyl-5-mercapto-1,3,4-thiadiazole. (Compound 118). M.p. 102°–104° C.

1-(2-Thiazolin-2-ylthio)-4-(3-(1-methyl-1,2,5,6-tetrahydropyridin-3-yl)-1,2,5-thiadiazol-4-ylthio)butane oxalate from 3-(3-(4-chlorobutylthio)-1,2,5-thiadiazol-4-yl)-1-methyl-1,2,5,6-tetrahydropyridine and 2-thiazoline-2-thiol. (Compound 119). M.p. 116°–117° C.

1-(2-Benzoxazolylthio)-4-(3-(1-methyl-1,2,5,6-tetrahydropyridin-3-yl)-1,2,5-thiadiazol-4-ylthio)butane oxalate from 3-(3-(4-chlorobutylthio)-1,2,5-thiadiazol-4-yl)-1-methyl-1,2,5,6-tetrahydropyridine and 2-mercaptobenzoxazole. (Compound 120). M.p. 156°–158° C.

1-(2-Methyl-1,3,4-thiadiazol-5-ylthio)-5-(3-(1-methyl-1,2,5,6-tetrahydropyridin-3-yl)-1,2,5-thiadiazol-4-ylthio)pentane oxalate from 3-(3-(5-chloropentylthio)-1,2,5-thiadiazol-4-yl)-1-methyl-1,2,5,6-tetrahydropyridine and 2-methyl-5-mercapto-1,3,4-thiadiazole. (Compound 121). M.p. 69°–70° C.

1-(2-Benzthiazolylthio)-5-(3-(1-methyl-1,2,5,6-tetrahydropyridin-3-yl)-1,2,5-thiadiazol-4-ylthio)pentane oxalate from 3-(3-(5-chloropentylthio)-1,2,5-thiadiazol-4-yl)-1-methyl-1,2,5,6-tetrahydropyridine and 2-mercaptobenzthiazole. (Compound 122). M.p. 116°–117° C.

1-(1-Methyltetrazol-5-ylthio)-5-(3-(1-methyl-1,2,5,6-tetrahydropyridin-3-yl)-1,2,5-thiadiazol-4-ylthio)pentane oxalate from 3-(3-(5-chloropentylthio)-1,2,5-thiadiazol-4-yl)-1-methyl-1,2,5,6-tetrahydropyridine and 1-methyl-5-mercaptotetrazole. (Compound 123). M.p. 96°–97° C.

1-(2-Methyl-1,3,4-thiadiazol-5-ylthio)-6-(3-(1-methyl-1,2,5,6-tetrahydropyridin-3-yl)-1,2,5-thiadiazol-4-ylthio)hexane oxalate from 3-(3-(6-chlorohexylthio)-1,2,5-thiadiazol-4-yl)-1-methyl-1,2,5,6-tetrahydropyridine and 2-methyl-5-mercapto-1,3,4-thiadiazole. (Compound 124). M.p. 85°–86° C.

1-(1-Methyltetrazol-5-ylthio)-6-(3-(1-methyl-1,2,5,6-tetrahydropyridin-3-yl)-1,2,5-thiadiazol-4-ylthio)hexane oxalate from 3-(3-(6-chlorohexylthio)-1,2,5-thiadiazol-4-yl)-1-methyl-1,2,5,6-tetrahydropyridine and 1-methyl-5-mercaptotetrazole. (Compound 125). M.p. 65°–66° C.

1-(2-Thiazolin-2-ylthio)-6-(3-(1-methyl-1,2,5,6-tetrahydropyridin-3-yl)-1,2,5-thiadiazol-4-ylthio)hexane oxalate from 3-(3-(6-chlorohexylthio)-1,2,5-thiadiazol-4-yl)-1-methyl-1,2,5,6-tetrahydropyridine and 2-thiazoline-2-thiol. (Compound 126). M.p. 61°–62° C.

EXAMPLE 71

3-(3-Methylsulfonyl-1,2,5-thiadiazol-4-yl)-1,2,5,6-tetrahydro-1-methylpyridine oxalate hemiacetone A solution of 3-(3-methylthio-1,2,5-thiadiazol-4-yl)-1,2,5,6-tetrahydro-1-methylpyridine oxalate (0.25 g, 0.0079 mol) in H$_2$O (10 ml) was cooled in an ice-water bath as a solution of oxone (0.7 g, 0.00114 mol) in H$_2$O (5 ml) was added dropwise. Cooling was removed and after 5 h excess NaHSO$_3$ was added. The solution was cooled in an ice-water bath, the solution made basic, and the mixture extracted with CH$_2$Cl$_2$ (3×25 ml). The extracts were dried, the solvent evaporated, and the residue purified by radial chromatography (5% EtOH-0.5% NH$_4$OH—CHCl$_3$) to give a white crystalline solid (0.2 g). The oxalate salt recrystallized from acetone to give colorless crystals. M.p. 96°–97.5° C. (Compound 127). Analysis and NMR confirmed that the salt contained 0.5 mol of acetone. Analysis C$_9$H$_{13}$N$_3$O$_2$S—C$_2$H$_2$O$_4$-0.5 C$_3$H$_6$O, C,H,N;

Theory C, 39.68; H, 4.79; N, 11.10; Found C, 39.52; H, 4.85; N, 11.19.

3-(3-[2-(1-Pyrrolidinyl)ethoxy]-1,2,5-thiadiazol-4-yl)-1,2,5,6-tetrahydro-1-methylpyridine dioxalate A suspension of NaH (0.0075 mol) in THF (25 ml) was treated with 2-hydroxyethylpyrrolidine (1 ml, 0.0086 mol) and after 30 min. the free base of (Compound 127) (0.6 g, 0.0023 mol), was added. After another hour, H$_2$O (2 ml) was added and the solvent evaporated. The residue was suspended in H$_2$O and extracted with CH$_2$Cl$_2$ (3×25 ml). The extracts were dried, the solvent evaporated, and the residue purified by radial chromatography (20% EtOH-2% NH$_4$OH—CHCl$_3$) to give a straw colored liquid (0.4 g). The dioxalate salt recrystallized from EtOH to give a white solid. M.p. 186°–188° C. (Compound 128).

Analysis C$_{14}$H$_{22}$N$_4$OS-2C$_2$H$_2$O$_4$, C,H,N; Theory C, 45.57; H, 5.52; N, 11.81; Found C, 45.53; H, 5.50; N, 11.61.

EXAMPLE 72

3-(3-(3-(5-Methyl-2-thienyl)-1-propoxy)-1,2,5-thiadiazol-4-yl)-1,2,5,6-tetrahydro-1-methylpyridine oxalate Sodium hydride (10.2 mmol) was added to a solution of 3-(5-methyl-2-thienyl)-1-propanol (4.0 g, 25.5 mmol) in THF (40 ml). The mixture was stirred for 1 h at room temperature, whereupon a solution of 3-(3-chloro-1,2,5-thiadiazol-4-yl)pyridine (1.0 g, 5.1 mmol) in THF (10 ml) was added dropwise to the reaction mixture. After stirring overnight at room temperature, the reaction was quenched with water then extracted with diethyl ether. The organic phase was dried over NaCl/Na$_2$SO$_4$ then evaporated to yield crude 3-(3-(5-methyl-2-thienyl)propoxy-1,2,5-thiadiazol-4-yl)pyridine. A solution of 3-(3-(5-methyl-2-thienyl)propoxy-1,2,5-thiadiazol-4-yl)pyridine (1.0 g, 3.2 mmol) and iodomethane (2.3 g, 16.0 mmol) in 60 ml of acetone was refluxed overnight. The solution was evaporated to yield 1.5 g of the quaternized product. Sodium borohydride (0.6 g, 16.0 mmol) was carefully added to a solution of the quaternized product (1.5 g) in ethanol (30 ml). The reaction was evaporated and the resulting residue was taken up in water and extracted with methylene chloride (3×100 ml). The organic phase was dried over NaCl/Na$_2$SO$_4$ then evaporated. The residue was purified by radial chromatography eluting with 0.5% NH$_4$OH/5.0% EtOH in CHCl$_3$. The oxalate salt was made to yield 337 mg of the title compound. M.p. 134°–137° C. (Compound 129).

The following compounds were made in the same manner as described above using the indicated alcohol instead of 3-(5-methyl-2-thienyl)-1-propanol:

3-(3-((5-Propyl-2-thienyl)methoxy)-1,2,5-thiadiazol-4-yl)-1,2,5,6-tetrahydro-1-methylpyridine oxalate (Compound 130) from (5-propyl-2-thienyl)-methanol. M.p. 134°–135° C.

3-(3-(3-(5-Pentyl-2-thienyl)-1-propoxy)-1,2,5-thiadiazol-4-yl)-1,2,5,6-tetrahydro-1-methylpyridine oxalate (Compound 131) from 3-(5-pentyl-2-thienyl)-1-propanol. M.p. 138°–140° C.

3-(3-(3-(2-Thienylthio)-1-propoxy)-1,2,5-thiadiazol-4-yl)-1,2,5,6-tetrahydro-1-methylpyridine oxalate (Compound 132) from 3-(2-thienylthio)-1-propanol. M.p. 102°–110° C.

EXAMPLE 73

3-(3-(3-(2-Thienyl)-1-propylthio)-1,2,5-thiadiazol-4-yl)-1,2,5,6-tetrahydro-1-methylpyridine oxalate A solution of 3-(3-chloro-1,2,5-thiadiazol-4-yl)pyridine (2.0 g, 10.1 mmol) in DMF (10 ml) was cooled to 5° C. whereupon potassium carbonate (2.8 g, 20.2 mmol) and sodium hydrosulfide monohydrate (1.5 g, 20.2 mmol) were added to the reaction. Stirred for 1 h then potassium carbonate (1.4 g, 10.1 mmol) and a solution of 3-(2-thienyl)-1-chloropropane (1.8 g, 11.2 mmol) in DMF (5 ml) were added to the reaction and stirred for 1 h at room temperature. The reaction was quenched with water then extracted with methylene chloride (3×75 ml). The organic phase was dried over NaCl/Na$_2$SO$_4$ then evaporated. The residue was purified by flash chromatography eluting with 1:1 ethyl acetate/hexanes to yield 1.0 g of 3-(3-(3-(2-thienyl)-1-propylthio)-1,2,5-thiadiazol-4-yl)pyridine. Quaternization and reduction was done as described in example 72. (Compound 133). M.p. 98°–100° C.

The following compounds were made in exactly the same manner as described above using the indicated alkylhalogenide:

3-(3-(2-Thienylmethylthio)-1,2,5-thiadiazol-4-yl)-1,2,5,6-tetrahydro-1-methylpyridine oxalate (Compound 134) using (2-thienyl)-chloromethane. M.p. 131°–135° C.

3-(3-(3-(2-Oxazolidinon-3-yl)-1-propylthio)-1,2,5-thiadiazol-4-yl)-1,2,5,6-tetrahydro-1-methylpyridine oxalate (Compound 135) using 3-(2-oxazolidinon-3-yl)-1-chloropropane. M.p. 104°–109° C.

3-(3-(3-(2-Thiazolidinon-3-yl)-1-propylthio-1,2,5-thiadiazol-4-yl)-1,2,5,6-tetrahydro-1-methylpyridine oxalate (Compound 136) using 3-(2-thiazolidinon-3-yl)-1-chloropropane. M.p. 75°–81° C.

3-(3-(5-Pentyl-2-thienyl)methylthio-1,2,5-thiadiazol-4-yl)-1,2,5,6-tetrahydro-1-methylpyridine oxalate (Compound 137) using (5-pentyl-2-thienyl)chloromethane. M.p. 143°–146° C.

(R)-(+) 3-(3-(3-(4-Benzyl-2-oxazolidinon-3-yl)-1-propylthio)-1,2,5-thiadiazol-4-yl)-1,2,5,6-tetrahydro-1-methylpyridine oxalate (Compound 138) using (R) 3-(4-benzyl-2-oxazolidinon-3-yl)-1-chloropropane. M.p. 124°–133° C.

(S)-(–) 3-(3-(3-(4-Benzyl-2-oxazolidinon-3-yl)-1-propylthio)-1,2,5-thiadiazol-4-yl)-1,2,5,6-tetrahydro-1-methylpyridine oxalate (Compound 139) using (S)-3-(4-benzyl-2-oxazolidinon-3-yl)-1-chloropropane. M.p. 132°–135° C.

(4R,5S)-3-(3-(3-(4-Methyl-5-phenyl-2-oxazolidinon-3-yl)-1-propylthio)-1,2,5-thiadiazol-4-yl)-1,2,5,6-tetrahydro-1-methylpyridine oxalate (Compound 140) using (4R,5S)-3-(4-methyl-5-phenyl-2-oxazolidinon-3-yl)-1-chloropropane. M.p. 102°–106° C.

(S)-3-(3-(3-(4-Isopropyl-2-oxazolidinon-3-yl)-1-propylthio)-1,2,5-thiadiazol-4-yl)-1,2,5,6-tetrahydro-1-methylpyridine oxalate (Compound 141) using (S)-3-(4-isopropyl-2-oxazolidinon-3-yl)-1-chloropropane. M.p. 75°–79° C.

(S)-3-(3-(3-(4-Ethyl-2-oxazolidinon-3-yl)-1-propylthio)-1,2,5-thiadiazol-4-yl)-1,2,5,6-tetrahydro-1-methylpyridine oxalate (Compound 142) using (S)-3-(4-ethyl-2-oxazolidinon-3-yl)-1-chloropropane. M.p. 69°–71° C.

(S)-3-(3-(3-(4-(2-Butyl)-2-oxazolidinon-3-yl)-1-propylthio-1,2,5-thiadiazol-4-yl)-1,2,5,6-tetrahydro-1-methylpyridine oxalate (Compound 143) using (S)-3-(4-(2-butyl)-2-oxazolidinon-3-yl)-1-chloropropane. M.p. 77°–80° C.

3-(3-(3-(4-Propyl-2-oxazolidinon-3-yl)-1-propylthio)-1,2,5-thiadiazol-4-yl)-1,2,5,6-tetrahydro-1-methylpyridine oxalate (Compound 144) using 3-(4-propyl-2-oxazolidinon-3-yl)-1-chloropropane. M.p. 65°–68° C.

EXAMPLE 74

A. 4-Methyl-1-(phenoxycarbonyl)-1,4-dihydropyridine

In a dry 500 ml three neck flask under nitrogen, a solution of cuprous iodide (0.28 g, 1.5 mmol) and dimethyl sulfide (8 ml) in 30 ml of dry THF was stirred at room temperature for 10 minutes. Pyridine (2.43 ml, 30 mmol) in 120 ml of dry THF was added to the reaction, then cooled to −25° C. Phenylchloroformate (3.9 ml, 30 mmol) in 10 ml dry THF was added to the reaction via an addition funnel (a thick brown precipitate formed immediately upon addition). The mixture was stirred for 15 minutes. Methyl magnesium chloride (10 ml, 30 mmol) was added to the mixture via syringe whereupon the brown precipitate dissolved. The reaction was stirred at −25° C. for 20 minutes then stirred at room temperature for 20 minutes. 20% $NH_4Cl_{(aq)}$ (70 ml) was added to the reaction. The mixture was then extracted with 150 ml diethyl ether. The organic extract was then washed with 40 ml portions of 20% $NH_4Cl_{(aq)}/NH_4OH$ (1:1), water, 10% $HCl_{(aq)}$, water, and brine. The organic layer was then dried over $NaCl/Na_2SO_4$, filtered, and concentrated to yield 5.9 g of a yellow oil. Kugelrohr distillation (bp. 150°–170° C., 1 mmHg) to yield 4.9 g (77%) of the desired compound (A).

B. 3-Formyl-4-methyl-1-(phenoxycarbonyl)-1,4-dihydropyridine

To a dry 50 ml flask under nitrogen, DMF (7.44 ml, 97 mmol) in 10 ml of dichloromethane was cooled to 0° C. Phosphorus oxychloride (4.5 ml, 48 mmol) was slowly added to the solution. The solution was stirred at room temperature for 30 minutes. (A) (4.7 g, 22 mmol) in 40 ml of dichloromethane was stirred in a 100 ml two neck flask under nitrogen at 0° C. The DMF/Phosphorus oxychloride solution was transferred to an addition funnel via cannula then slowly added to the (A)/dichloromethane solution. The ice bath was then removed, and the reaction was stirred at room temperature for 20 hours. The reaction was cooled to 0° C. whereupon a solution of potassium acetate (15 g) in 50 ml of water was carefully added via the addition funnel. The mixture was then allowed to reflux for 20 minutes. The methylene chloride layer was separated then extracted once more with 100 ml methylene chloride. The organic phases were combined then washed with 40 ml portions of water, $K_2CO_{3(aq)}$, water and brine, then dried over $NaCl/Na_2SO_4$. The organics were concentrated on a rotary evaporator to yield 4 g of a brown oil. Purified by flash chromatography over silica gel eluting with ethyl acetate/hexane. Yield 2.0 g (37%) of the desired compound (B).

C. 4-Methyl-3-pyridinecarboxaldehyde

Methanol (85 ml), triethylamine (1.4 g), and (B) (5.0 g, 20.6 mmol) were placed in a 250 ml flask over nitrogen. The solution was refluxed for 3 hours. The reaction was then concentrated and 5% Pd/C (0.5 g) and toluene (85 ml) were added to the flask. This mixture was refluxed for 2 hours, then cooled to room temperature. The 5% Pd/C was removed by filtration and the filtrate was concentrated.

The resulting oil was purified by flash chromatography over silica gel eluting with ethyl acetate/hexane. The yield of (C) was 1.3 g (47%).

D. Alpha-amino-alpha(3-(4-methylpyridyl))acetonitrile

Dissolved potassium cyanide (7.3 g, 112.6 mmol) and ammonium chloride (6.0 g, 112.6 mmol) in water (150 ml) in a 250 ml flask under nitrogen. (C) (10.9 g, 90.1 mmol) was added to the reaction which was stirred at room temperature overnight. The reaction mixture was extracted with ethyl acetate (3×300 ml). The organic extracts were combined, dried over $NaCl/Na_2SO_4$, then concentrated to yield 11 g of a brown oil (D). Used directly in the next step.

E. 3-(3-Chloro-1,2,5-thiadiazol-4-yl)-4-methylpyridine

Sulfurmonochloride (73.5 mmol, 5.9 ml) in DMF (90 ml) was placed in a 250 ml flask under nitrogen and cooled to −25° C. (D) (3.6 g, 24.5 mmol) in DMF (10 ml) was added to the reaction via an addition funnel. The reaction was allowed to stir overnight. After warming to room temperature, water (30 ml) and diethyl ether (60 ml) were added to the reaction and the ether layer was separated, then discarded. The reaction was then basified with 50% NaOH$_{(aq)}$, then extracted with diethyl ether (4×90 ml). The organic extracts were combined, dried over $NaCl/Na_2SO_4$, and concentrated to yield a brown oil. The oil was purified by flash chromatography over 100 g silica gel, eluting with 0.05% $NH_4OH$/0.5% ethanol in chloroform. Yield of (E) was 2 g (38%).

F. 3-(3-Methoxy-1,2,5-thiadiazol-4-yl)-4-methylpyridine

A solution of sodium (0.32 g, 14 mmol) in methanol (10 ml) was prepared in a 25 ml flask under nitrogen. (E) (0.6 g, 2.8 mmol) was added to the reaction and was heated at 50° C. for 3 hours, then stirred overnight at room temperature. Concentrated on the rotary evaporator then dissolved the resulting solid in 1N $HCl_{(aq)}$ and washed with diethyl ether. The aqueous layer was basified with 5N NaOH$_{(aq)}$, then extracted with methylene chloride (4×50 ml). The combined organic extracts were dried over $NaCl/Na_2SO_4$ and concentrated to yield 344 mg of an oil (F) (60%).

G. 3-(3-Methoxy-1,2,5-thiadiazol-4-yl)-4-methylpyridinium iodide

A mixture of (F) (335 mg, 1.6 mmol), iodomethane (1.14 g, 8.0 mmol), and acetone (100 ml) was stirred in a 250 ml flask under nitrogen overnight at room temperature. Concentrated the reaction on the rotary evaporator to yield 500 mg of a yellow solid (G). Used directly in next step.

H. 1,2,5,6-Tetrahydro-3-(3-methoxy-1,2,5-thiadiazol-4-yl)-1,4-dimethylpyridine fumarate Sodium borohydride (300 mg, 8.0 mmol) was added to a solution of (G) (1.6 mmol) and ethanol (15 ml) in a 50 ml flask under nitrogen. The reaction was allowed to stir overnight at room temperature. The reaction was concentrated on the rotary evaporator. Dissolved the resulting solid in 1N $HCl_{(aq)}$ (75 ml), then washing with diethyl ether. The aqueous layer was basified, then extracted with methylene chloride (4×75 ml). The combined organic extracts were dried over $NaCl/Na_2SO_4$, and concentrated to yield an oil which was purified by flash chromatography (silica gel eluting with $NH_4OH$/ethanol in chloroform). Yield was 91 mg. Isolated as fumarate salt, 130.4 mg. M.p. 99°–105° C. Analysis calc. for $C_{14}H_{19}N_3O_5S$. C: 49.26; H: 5.61; N: 12.31. Found C: 49.11; H: 5.53; N: 12.03. Compound 145.

EXAMPLE 75

The following compound was made in exactly the same manner as described in example 74F through H using hexanol instead of methanol:

3-(3-Hexyloxy-1,2,5-thiadiazol-4-yl)-1,2,5,6-tetrahydro-1,4-dimethylpyridine oxalate. M.p. 109°–111° C. Analysis calc. for $C_{17}H_{27}N_3O_5S$. C: 52.97; H: 7.06; N: 10.70. Found C: 53.17; H: 6.88; N: 10.98. Compound 146.

EXAMPLE 76

A. Alpha-amino-alpha-(6-methyl-3-pyridinyl)acetonitrile

To a solution of potassium cyanide (6.96 g, 107 mmol) and ammonium chloride (5.72 g, 107 mmol) in water (5 ml) was added 6-methyl-3-pyridin-carboxaldehyde (8.68 g, 71.5 mmol) and the reaction mixture was stirred at room temperature for 18 h. The reaction mixture was basified with 50% NaOH and extracted with ethyl acetate. The organic phase was dried ($MgSO_4$) and evaporated to give the crude desired product in 7 g yield. The product was used without further purification.

B. 3-(3-Chloro-1,2,5-thiadiazol-4-yl)-6-methylpyridine

A solution of sulphurmonochloride (11.7 ml, 142 mmol) in DMF (50 ml) was slowly added to a solution of alpha-amino-alpha-(6-methyl-3-pyridinyl)acetonitrile (7 g, 47 mmol) at room temperature. The reaction mixture was stirred for 18 h and thereafter basified with 50% NaOH and extracted with ether. The ether phases were dried ($MgSO_4$) and evaporated. The residue was purified by column chromatography (eluent, $EtOAc:CH_2Cl_2$ (1:1)) to give the wanted product in 5.30 g (54%) yield.

C. 3-(3-Hexylthio-1,2,5-thiadiazol-4-yl)-6-methylpyridine

Sodium hydrogen sulfide monohydrate (0.33 g, 4.4 mmol) was added to a solution of 3-(3-chloro-1,2,5-thiadiazol-4-yl)-6-methylpyridine (0.85 g, 4 mmol) in DMF (20 ml) at room temperature and the reaction mixture was stirred for 1 h. Potassium carbonate (1.65 g, 12 mmol) and 1-hexylbromide (0.99 g, 6 mmol) were added and the reaction mixture was stirred for additionally 24 h. 1N HCl was added and the reaction mixture was extracted once with ether. The aqueous phase was basified with 50% NaOH and extracted with ether. The ether phases were dried and evaporated to give crude title compound.

D. 3-(3-Hexylthio-1,2,5-thiadiazol-4-yl)-1,6-dimethylpyridinium iodide

Methyl iodide (1 ml, 15 mmol) was added to a solution of 3-(3-hexylthio-1,2,5-thiadiazol-4-yl)-6-methylpyridine (4 mmol) in acetone (5 ml) and the reaction mixture was stirred at room temperature for 20 h. Evaporation of the reaction mixture gave the crude product, which was used without further purification.

E. 3-(3-Hexylthio-1,2,5-thiadiazol-4-yl)-1,2,5,6-tetrahydro-1,6-dimethylpyridine oxalate Under nitrogen, sodium borohydride (380 mg, 10 mmol) was added to a solution of 3-(3-hexylthio-1,2,5-thiadiazol-4-yl)-1,6-dimethylpyridinium iodide (4 mmol) in ethanol (99.9%, 20 ml) at −10° C. The reaction mixture was stirred at −10° C. for 1 h. After evaporation the residue was dissolved in water and extracted with ethyl acetate. The dried organic phases were evaporated and the residue purified by column chromatography (eluent: EtOAc:MeOH (4:1)). The title compound was crystallized as the oxalate salt from acetone. Recrystallization from acetone gave the wanted product in 700 mg yield. M.p. 127°–128° C. (Compound 147).

EXAMPLE 77

The following compounds were made in the same manner as described in example 76C through E using the appropriate alkylbromide instead of 1-hexylbromide:

3-(3-Pentylthio-1,2,5-thiadiazol-4-yl)-1,2,5,6-tetrahydro-1,6-dimethylpyridine oxalate. M.p. 112°–113° C. (Compound 148).

3-(3-(4-Cyanobenzylthio)-1,2,5-thiadiazol-4-yl)-1,2,5,6-tetrahydro-1,6-dimethylpyridine oxalate. M.p. 74°–76° C. (Compound 149).

3-(3-(4-Cyanobutylthio)-1,2,5-thiadiazol-4-yl)-1,2,5,6-tetrahydro-1,6-dimethylpyridine oxalate. M.p. 99°–101° C. (Compound 150).

3-(3-Butylthio-1,2,5-thiadiazol-4-yl)-1,2,5,6-tetrahydro-1,6-dimethylpyridine oxalate. M.p. 119°–120° C. (Compound 151).

3-(3-Ethylthio-1,2,5-thiadiazol-4-yl)-1,2,5,6-tetrahydro-1,6-dimethylpyridine oxalate. M.p. 154°–155° C. (Compound 152).

3-(3-(4-Pentynylthio)-1,2,5-thiadiazol-4-yl)-1,2,5,6-tetrahydro-1,6-dimethylpyridine oxalate. M.p. 111°–113° C. (Compound 153).

3-(3-Phenylpropylthio)-1,2,5-thiadiazol-4-yl)-1,2,5,6-tetrahydro-1,6-dimethylpyridine oxalate. M.p. 125°–126° C. (Compound 154).

EXAMPLE 78

A. 3-(3-Hexyloxy-1,2,5-thiadiazol-4-yl)-6-methylpyridine

Sodium hydride (0.72 g, 15 mmol) was dissolved in dry THF (20 ml) and 1-hexanol (1.53 g, 15 mmol) and a solution of 3-(3-chloro-1,2,5-thiadiazol-4-yl)-6-methylpyridine (1.06 g, 5 mmol) in dry THF (15 ml) was added. The reaction mixture was stirred for 2 h. After addition of water the mixture was extracted with ether, and the ether phase was dried and evaporated. The residue consisted of the crude title compound, which was used without further purification.

B. 3-(3-Hexyloxy-1,2,5-thiadiazol-4-yl)-1,2,5,6-tetrahydro-1,6-dimethylpyridine oxalate M.p. 99°–100° C. (Compound 155) was made in the same manner as described in example 76D through E.

EXAMPLE 79

The following compounds were prepared in the same manner as described in example 78 using the appropriate alcohol instead of 1-hexanol:

3-(3-Pentyloxy-1,2,5-thiadiazol-4-yl)-1,2,5,6-tetrahydro-1,6-dimethylpyridine oxalate. M.p. 122°–123° C. (Compound 156).

3-(3-Butoxy-1,2,5-thiadiazol-4-yl)-1,2,5,6-tetrahydro-1,6-dimethylpyridine oxalate. M.p. 133°–134° C. (Compound 157).

3-(3-(4-Pentenyloxy)-1,2,5-thiadiazol-4-yl)-1,2,5,6-tetrahydro-1,6-dimethylpyridine oxalate. M.p. 133°–134° C. (Compound 158).

3-(3-(3-Hexynyloxy)-1,2,5-thiadiazol-4-yl)-1,2,5,6-tetrahydro-1,6-dimethylpyridine oxalate. M.p. 126°–128° C. (Compound 159).

3-(3-Ethoxy-1,2,5-thiadiazol-4-yl)-1,2,5,6-tetrahydro-1,6-dimethylpyridine oxalate. M.p. 128°–129° C. (Compound 160).

EXAMPLE 80

3-(3-(3-Carboxypropylthio)-1,2,5-thiadiazol-4-yl)-1,2,5,6-tetrahydro-1-methylpyridine A solution of 3-(3-(3-carboxypropylthio)-1,2,5-thiadiazol-4-yl)-1,2,5,6-tetrahydro-1-methylpyridine hydrochloride (0.70 g, 2 mmol) in concentrated hydrochloric acid (10 ml) was heated at reflux for 6 hours. The reaction mixture was evaporated at reduced pressure. The residue was dissolved in water and neutralized with a sodiumhydroxide solution giving the title compound in 80 % yield. M.p. 99°–101° C. Compound 258.

In exactly the same manner the following compounds were prepared:

3-(3-(3-Carboxypropoxy)-1,2,5-thiadiazol-4-yl)-1,2,5,6-tetrahydro-1-methylpyridine. M.p. 113°–116° C. Compound 259.

3-(3-(5-Carboxypentylthio)-1,2,5-thiadiazol-4-yl)-1,2,5,6-tetrahydro-1-methylpyridine. M.p. 110°–112° C. Compound 260.

EXAMPLE 81

3-(3-(5-Mercaptopentylthio)-1,2,5-thiadiazol-4-yl)-1,2,5,6-tetrahydro-1-methylpyridine oxalate To a solution of 3-(3-(5-chloropentylthio)-1,2,5-thiadiazol-4-yl)-1,2,5,6-tetrahydro-1-methylpyridine (0.31 g, 1 mmol) in dimethylformamide (5 ml) was added sodium hydrogensulfide (0.35 g, 5 mmol) and the mixture was stirred at room temperature for 48 hours. Water was added and the free base extracted with ether. The free base was crystallized as the oxalate salt from acetone. Yield 50%. M.p. 106°–107° C. Compound 261.

In exactly the same manner the following compounds were prepared:

3-(3-(6-Mercaptohexylthio)-1,2,5-thiadiazol-4-yl)-1,2,5,6-tetrahydro-1-methylpyridine oxalate. M.p. 105°–106° C. Compound 262.

3-(3-(4-Mercaptobutylthio)-1,2,5-thiadiazol-4-yl)-1,2,5,6-tetrahydro-1-methylpyridine oxalate. M.p. 142°–144° C. Compound 263.

I claim:

1. A method of treating a gastrointestinal hypermotility disorder in a subject in need thereof comprising administering to said subject an effective amount of a compound of formula I

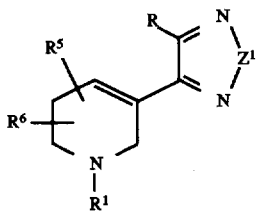

wherein $Z^1$ is oxygen or sulphur;

R is hydrogen; halogen; amino; —NHCO—$R^2$; $C_{3-7}$-cycloalkyl; $C_{4-10}$-(cycloalkylalkyl); —$Z^2$—$C_{3-7}$-cycloalkyl optionally substituted with $C_{1-6}$-alkyl; —$Z^2$—$C_{4-10}$-(cycloalkylalkyl); —$Z^2$—$C_{4-10}$-(cycloalkenylalkyl); —$Z^2$—$C_{4-10}$-(methylenecycloalkylakyl); —NH—$R^2$; —N$R^2R^3$; —NH—O$R^2$; phenyl; phenoxy; benzoyl; benzyloxycarbonyl; tetrahydronaphthyl; indenyl; $R^2$; —$Z^2R^2$; —SO$R^2$; —SO$_2R^2$; —$Z^2R^2$—$Z^3$—$R^3$; —$Z^2$—$R^2$—$Z^3$—$R^3$—$Z^4$—$R^4$; —$Z^2$—$R^2$—CO—$R^3$; —$Z^2$—$R^2$—CO$_2$—$R^3$; —$Z^2$—$R^2$—O$_2$C—$R^3$; —$Z^2$—$R^2$—CONH—$R^3$; or —$Z^2$—$R^2$—NHCO$R^3$; wherein $Z^2$, $Z^3$ and $Z^4$ independently are oxygen or sulphur, and $R^2$, $R^3$ and $R^4$ independently are straight or branched $C_{1-5}$-alkyl, straight or branched $C_{2-15}$-alkenyl, straight or branched $C_{2-15}$-alkynyl, each of which is optionally substituted with halogen(s), —OH, —CN, —CF$_3$, —SH, —COOH, —NH—$R^2$, —N$R^2R^3$, $C_{1-6}$-alkyl ester, one or two phenyl, phenoxy, benzoyl or benzyloxycarbonyl wherein each aromatic group is optionally substituted with one or two halogen, —CN, $C_{1-4}$-alkyl or $C_{1-4}$-alkoxy;

$R^5$ and $R^6$ may be present at any appropriate position and independently are hydrogen, straight or branched $C_{1-5}$-alkyl, straight or branched $C_{2-5}$-alkenyl, straight or branched $C_{2-5}$-alkynyl, straight or branched $C_{1-10}$-alkoxy, —OH, halogen, —NH$_2$, carboxy, or straight or branched $C_{1-5}$-alkyl substituted with —OH; and $R^1$ is hydrogen, straight or branched $C_{1-5}$-alkyl, straight or branched $C_{2-5}$-alkenyl or straight or branched $C_{2-5}$-alkynyl; or a pharmaceutically acceptable salt thereof.

2. The method according to claim 1, wherein $Z^1$ is sulphur.

3. The method according to claim 2, wherein $R^1$ is hydrogen or straight or branched $C_{1-5}$-alkyl, $R^5$ and $R^6$ independently are hydrogen, methyl, methoxy, hydroxy, halogen or amino.

4. The method according to claim 2, wherein $R^1$ is hydrogen or methyl, $R^5$ and $R^6$ are hydrogen, R is —$Z^2R^2$ wherein $Z^2$ is oxygen or sulphur and $R^2$ is straight or branched $C_{1-5}$-alkyl.

5. The method according to claim 2, wherein $R^1$ is hydrogen or methyl, $R^5$ and $R^6$ are hydrogen, R is —$Z^2R^2$ wherein $Z^2$ is oxygen or sulphur and $R^2$ is straight or branched $C_{1-5}$-alkyl substituted with halogen(s) or —CF$_3$.

6. The method according to claim 1, wherein the compound is:

1,2,5,6-Tetrahydro-3-(3-methoxy-1,2,5-thiadiazol-4-yl)-1-methylpyridine;

3-(3-Ethoxy-1,2,5-thiadiazol-4-yl)-1,2,5,6-tetrahydro-1-methylpyridine;

1,2,5,6-Tetrahydro-1-methyl-3-(3-propoxy-1,2,5-thiadiazol-4-yl)pyridine;

3-(3-Butoxy-1,2,5-thiadiazol-4-yl)-1,2,5,6-tetrahydro-1-methylpyridine;

1,2,5,6-Tetrahydro-3-(3-isopropoxy-1,2,5-thiadiazol-4-yl)-1-methylpyridine;

1,2,5,6-Tetrahydro-1-methyl-3-(3-pentyloxy-1,2,5-thiadiazol-4-yl)pyridine;

1,2,5,6-Tetrahydro-3-(3-isobutoxy-1,2,5-thiadiazol-4-yl)-1-methylpyridine;

1,2,5,6-Tetrahydro-3-(3-isopentyloxy-1,2,5-thiadiazol-4-yl)-1-methylpyridine;

3-(3-Hexyloxy-1,2,5-thiadiazol-4-yl)-1,2,5,6-tetrahydro-1-methylpyridine;

3-(3-(3-Butenyloxy)-1,2,5-thiadiazol-4-yl)-1,2,5,6-tetrahydro-1-methylpyridine;

3-(3-(2-Butynyloxy)-1,2,5-thiadiazol-4-yl)-1,2,5,6-tetrahydro-1-methylpyridine;

1,2,5,6-Tetrahydro-1-methyl-3-(3-propargyloxy-1,2,5-thiadiazol-4-yl)pyridine;

3-(3-Butoxy-1,2,5-thiadiazol-4-yl)-1,2,5,6-tetrahydropyridine;

3-(3-Ethoxy-1,2,5-thiadiazol-4-yl)-1-ethyl-1,2,5,6-tetrahydropyridine;

3-(3-Heptyloxy-1,2,5-thiadiazol-4-yl)-1,2,5,6-tetrahydro-1-methylpyridine;

3-(3-(3-Pentynyloxy)-1,2,5-thiadiazol-4-yl)-1,2,5,6-tetrahydro-1-methylpyridine;

3-(3-(4-Pentenyloxy)-1,2,5-thiadiazol-4-yl)-1,2,5,6-tetrahydro-1-methylpyridine;

3-(3-(2-Propenyloxy)-1,2,5-thiadiazol-4-yl)-1,2,5,6-tetrahydro-1-methylpyridine;

3-(3-Octyloxy-1,2,5-thiadiazol-4-yl)-1,2,5,6-tetrahydro-1-methylpyridine;

3-(3-(3-Hexynyloxy)-1,2,5-thiadiazol-4-yl)-1,2,5,6-tetrahydro-1-methylpyridine;

3-(3-(3-Methyl-2-butenyloxy)-1,2,5-thiadiazol-4-yl)-1,2,5,6-tetrahydro-1-methylpyridine;

3-(3-(3-Butenyl-2-oxy)-1,2,5-thiadiazol-4-yl)-1,2,5,6-tetrahydro-1-methylpyridine;

3-(3-(4-Hexenyloxy)-1,2,5-thiadiazol-4-yl)-1,2,5,6-tetrahydro-1-methylpyridine;

trans-3-(3-(3-Hexenyloxy)-1,2,5-thiadiazol-4-yl)-1,2,5,6-tetrahydro-1-methylpyridine;

cis-3-(3-(2-Pentenyloxy)-1,2,5-thiadiazol-4-yl)-1,2,5,6-tetrahydro-1-methylpyridine;

cis-3-(3-(2-Hexenyloxy)-1,2,5-thiadiazol-4-yl)-1,2,5,6-tetrahydro-1-methylpyridine;

3-(3-(5-Hexenyloxy)-1,2,5-thiadiazol-4-yl)-1,2,5,6-tetrahydro-1-methylpyridine;

cis-3-(3-(3-Hexenyloxy)-1,2,5-thiadiazol-4-yl)-1,2,5,6-tetrahydro-1-methylpyridine;

trans-3-(3-(2-Hexenyloxy)-1,2,5-thiadiazol-4-yl)-1,2,5,6-tetrahydro-1-methylpyridine;

1,2,5,6-Tetrahydro-3-(3-hexyloxy-1,2,5-thiadiazol-4-yl)pyridine;

1,2,5,6-Tetrahydro-3-(3-methoxy-1,2,5-thiadiazol-4-yl)-1,4-dimethylpyridine;

3-(3-Hexyloxy-1,2,5-thiadiazol-4-yl)-1,2,5,6-tetrahydro-1,4-dimethylpyridine;

3-(3-Hexyloxy-1,2,5-thiadiazol-4-yl)-1,2,5,6-tetrahydro-1,6-dimethylpyridine;

3-(3-Pentyloxy-1,2,5-thiadiazol-4-yl)-1,2,5,6-tetrahydro-1,6-dimethylpyridine;

3-(3-Butoxy-1,2,5-thiadiazol-4-yl)-1,2,5,6-tetrahydro-1,6-dimethylpyridine;

3-(3-(4-Pentenyloxy)-1,2,5-thiadiazol-4-yl)-1,2,5,6-tetrahydro-1,6-dimethylpyridine;

3-(3-(3-Hexynyloxy)-1,2,5-thiadiazol-4-yl)-1,2,5,6-tetrahydro-1,6-dimethylpyridine;

3-(3-Ethoxy-1,2,5-thiadiazol-4-yl)-1,2,5,6-tetrahydro-1,6-dimethylpyridine;

3-(3-(1-Ethylpentyloxy)-1,2,5-thiadiazol-4-yl)-1,2,5,6-tetrahydro-1-methylpyridine;

3-(3-(1-Ethylbutoxy)-1,2,5-thiadiazol-4-yl)-1,2,5,6-tetrahydro-1-methylpyridine;

3-(3-(1-Methylpentyloxy)-1,2,5-thiadiazol-4-yl)-1,2,5,6-tetrahydro-1-methylpyridine;

3-(3-(5-Hexynyloxy)-1,2,5-thiadiazol-4-yl)-1,2,5,6-tetrahydro-1-methylpyridine;

3-(3-(3-Methyl-4-pentenyloxy)-1,2,5-thiadiazol-4-yl)-1,2,5,6-tetrahydro-1-methylpyridine;

3-(3-(2,3-Dimethylpentyloxy)-1,2,5-thiadiazol-4-yl)-1,2,5,6-tetrahydro-1-methylpyridine;

3-(3-(4-Methylhexyloxy)-1,2,5-thiadiazol-4-yl)-1,2,5,6-tetrahydro-1-methylpyridine;

3-(3-(1-Methylhexyloxy)-1,2,5-thiadiazol-4-yl)-1,2,5,6-tetrahydro-1-methylpyridine;

3-(3-(3-Methylpentyloxy)-1,2,5-thiadiazol-4-yl)-1,2,5,6-tetrahydro-1-methylpyridine;

3-(3-Isoheptyloxy-1,2,5-thiadiazol-4-yl)-1,2,5,6-tetrahydro-1-methylpyridine;

3-(3-Isohexyloxy-1,2,5-thiadiazol-4-yl)-1,2,5,6-tetrahydro-1-methylpyridine;

3-(3-Hexyloxy-1,2,5-thiadiazol-4-yl)-1,2,5,6-tetrahydro-1-ethylpyridine;

3-(3-Ethoxy-1,2,5-thiadiazol-4-yl)-1,2,5,6-tetrahydropyridine; or a pharmaceutically acceptable salt thereof.

7. The method according to claim 1, wherein the compound is:

3-(3-Cyclopropylmethoxy-1,2,5-thiadiazol-4-yl)-1,2,5,6-tetrahydro-1-methylpyridine;

1,2,5,6-Tetrahydro-3-(3-methoxyethoxy-1,2,5-thiadiazol-4-yl)-1-methylpyridine;

3-(3-(2-(2-Methoxyethoxy)ethoxy)-1,2,5-thiadiazol-4-yl)-1,2,5,6-tetrahydro-1-methylpyridine;

3-(3-(3-Ethoxy-1-propoxy)-1,2,5-thiadiazol-4-yl)-1,2,5,6-tetrahydro-1-methylpyridine;

3-(3-(2-Ethoxyethoxy)-1,2,5-thiadiazol-4-yl)-1,2,5,6-tetrahydro-1-methylpyridine;

3-(3-(2-Butoxyethoxy)-1,2,5-thiadiazol-4-yl)-1,2,5,6-tetrahydro-1-methylpyridine;

3-(3-(2-(2-Butoxyethoxy)ethoxy)-1,2,5-thiadiazol-4-yl)-1,2,5,6-tetrahydro-1-methylpyridine;

3-(3-(2-(2-Ethoxyethoxy)ethoxy)-1,2,5-thiadiazol-4-yl)-1,2,5,6-tetrahydro-1-methylpyridine;

1,2,5,6-Tetrahydro-1-methyl-3-(3-(6,6,6-trifluorohexyloxy)-1,2,5-thiadiazol-4-yl)pyridine;

1,2,5,6-Tetrahydro-1-methyl-3-(3-(3-(4-methoxyphenyl)-1-propoxy)-1,2,5-thiadiazol-4-yl)pyridine;

1,2,5,6-Tetrahydro-1-methyl-3-(3-(2-(4-methoxyphenyl)-1-ethoxy)-1,2,5-thiadiazol-4-yl)pyridine;

1,2,5,6-Tetrahydro-1-methyl-3-(3-(3-hydroxy-1-propoxy)-1,2,5-thiadiazol-4-yl)pyridine;

1,2,5,6-Tetrahydro-1-methyl-3-(3-(2-phenyl-1-ethoxy)-1,2,5-thiadiazol-4-yl)pyridine;

1,2,5,6-Tetrahydro-1-methyl-3-(3-(3-hydroxy-1-hexyloxy)-1,2,5-thiadiazol-4-yl)pyridine;

1,2,5,6-Tetrahydro-1-methyl-3-(3-(3-phenyl-1-propoxy)-1,2,5-thiadiazol-4-yl)pyridine;

1,2,5,6-Tetrahydro-1-methyl-3-(3-(6-acetamido-1-hexyloxy)-1,2,5-thiadiazol-4-yl)pyridine;

1,2,5,6-Tetrahydro-1-methyl-3-(3-(2-acetamido-1-ethoxy)-1,2,5-thiadiazol-4-yl)pyridine;

1,2,5,6-Tetrahydro-1-methyl-3-(3-(2-propionamido-1-ethoxy)-1,2,5-thiadiazol-4-yl)pyridine;

1,2,5,6-Tetrahydro-1-methyl-3-(3-(2-benzylthio-1-ethoxy)-1,2,5-thiadiazol-4-yl)pyridine;

1,2,5,6-Tetrahydro-1-methyl-3-(3-(2-ureido-1-ethoxy)-1,2,5-thiadiazol-4-yl)pyridine;

1,2,5,6-Tetrahydro-1-methyl-3-(3-(2-ethylsulfinyl-1-ethoxy)-1,2,5-thiadiazol-4-yl)pyridine;

3-(3-(2,4-Dimethylphenylpropoxy)-1,2,5-thiadiazol-4-yl)-1,2,5,6-tetrahydro-1-methylpyridine;

3-(3-(3,4-Dimethylphenylpropoxy)-1,2,5-thiadiazol-4-yl)-1,2,5,6-tetrahydro-1-methylpyridine;

3-(3-(4-Fluorophenylpropoxy)-1,2,5-thiadiazol-4-yl)-1,2,5,6-tetrahydro-1-methylpyridine;

3-(3-(4-Chlorophenylpropoxy)-1,2,5-thiadiazol-4-yl)-1,2,5,6-tetrahydro-1-methylpyridine;

3-(3-(3-Methylphenylpropoxy)-1,2,5-thiadiazol-4-yl)-1,2,5,6-tetrahydro-1-methylpyridine;

3-(3-(4-Methylphenylpropoxy)-1,2,5-thiadiazol-4-yl)-1,2,5,6-tetrahydro-1-methylpyridine;

3-(3-Phenylbutoxy-1,2,5-thiadiazol-4-yl)-1,2,5,6-tetrahydro-1-methylpyridine;

3-(3-(2-Methylphenylpropoxy)-1,2,5-thiadiazol-4-yl)-1,2,5,6-tetrahydro-1-methylpyridine;

3-(3-(2,5-Dimethylphenylpropoxy)-1,2,5-thiadiazol-4-yl)-1,2,5,6-tetrahydro-1-methylpyridine;

3-(3-Methylthioethoxy-1,2,5-thiadiazol-4-yl)-1,2,5,6-tetrahydro-1-methylpyridine;

3-(3-Dimethylaminoethoxy-1,2,5-thiadiazol-4-yl)-1,2,5,6-tetrahydro-1-methylpyridine;

3-(3-(3,4-Dichlorophenylpropoxy)-1,2,5-thiadiazol-4-yl)-1,2,5,6-tetrahydro-1-methylpyridine;

3-(3-Dimethylaminopropoxy-1,2,5-thiadiazol-4-yl)-1,2,5,6-tetrahydro-1-methylpyridine;

3-(3-(4-Methylphenylpropoxy)-1,2,5-thiadiazol-4-yl)-1,2,5,6-tetrahydro-1-methylpyridine;

3-(3-(4-Cyclohexylbutoxy)-1,2,5-thiadiazol-4-yl)-1,2,5,6-tetrahydro-1-methylpyridine;

3-(3-(5-Hydroxyhexyloxy)-1,2,5-thiadiazol-4-yl)-1,2,5,6-tetrahydro-1-methylpyridine;

3-(3-(5-Oxyhexyloxy)-1,2,5-thiadiazol-4-yl)-1,2,5,6-tetrahydro-1-methylpyridine;

3-(3-(3-Cyclohexenylmethoxy)-1,2,5-thiadiazol-4-yl)-1,2,5,6-tetrahydro-1-methylpyridine;

3-(3-Isobutylthioethoxy-1,2,5-thiadiazol-4-yl)-1,2,5,6-tetrahydro-1-methylpyridine;

3-(3-Cyclopropylpropoxy-1,2,5-thiadiazol-4-yl)-1,2,5,6-tetrahydro-1-methylpyridine;

3-(3-(2-Methylcyclopropylmethoxy)-1,2,5-thiadiazol-4-yl)-1,2,5,6-tetrahydro-1-methylpyridine;

3-(3-Cyclopentylpropyloxy-1,2,5-thiadiazol-4-yl)-1,2,5,6-tetrahydro-1-methylpyridine;

3-(3-(4,4,4-Trifluorobutoxy)-1,2,5-thiadiazol-4-yl)-1,2,5,6-tetrahydro-1-methylpyridine;

3-(3-(6,6,6-Trifluorohexyloxy)-1,2,5-thiadiazol-4-yl)-1,2,5,6-tetrahydro-1-methylpyridine;

3-(3-(3-Cyclobutylpropoxy)-1,2,5-thiadiazol-4-yl)-1,2,5,6-tetrahydro-1-methylpyridine;

3-(3-Isopropoxyethoxy-1,2,5-thiadiazol-4-yl)-1,2,5,6-tetrahydro-1-methylpyridine;

3-(3-(2,2,2-Trifluoroethoxy)-1,2,5-thiadiazol-4-yl)-1,2,5,6-tetrahydro-1-methylpyridine;

3-(3-(2-Chlorophenylpropoxy)-1,2,5-thiadiazol-4-yl)-1,2,5,6-tetrahydro-1-methylpyridine;

3-(3-(3-Cyclohexylpropoxy)-1,2,5-thiadiazol-4-yl)-1,2,5,6-tetrahydro-1-methylpyridine;

3-(3-(2-Cyclohexylethoxy)-1,2,5-thiadiazol-4-yl)-1,2,5,6-tetrahydro-1-methylpyridine;

3-(3-(2,2,2-Trifluoroethoxy)-1,2,5-thiadiazol-4-yl)-1,2,5,6-tetrahydropyridine;

3-(3-(3-Carboxypropoxy)-1,2,5-thiadiazol-4-yl)-1,2,5,6-tetrahydro-1-methylpyridine; or a pharmaceutically acceptable salt thereof.

8. The method according to claim 1, wherein the compound is:

3-(3-Benzyloxy-1,2,5-thiadiazol-4-yl)-1,2,5,6-tetrahydro-1-methylpyridine;

3-(3-(2,3-Dihydro-1-indenyloxy)-1,2,5-thiadiazol-4-yl)-1,2,5,6-tetrahydro-1-methylpyridine;

3-(3-(1,2,3,4-Tetrahydro-2-naphthalyloxy)-1,2,5-thiadiazol-4-yl)-1,2,5,6-tetrahydro-1-methylpyridine;

3-(3-(4-Ethylbenzyloxy)-1,2,5-thiadiazol-4-yl)-1,2,5,6-tetrahydro-1-methylpyridine;

3-(3-(4-Butylbenzyloxy)-1,2,5-thiadiazol-4-yl)-1,2,5,6-tetrahydro-1-methylpyridine; or a pharmaceutically acceptable salt thereof.

9. The method according to claim 1, wherein the compound is:

3-(3-Propylthio-1,2,5-thiadiazol-4-yl)-1,2,5,6-tetrahydro-1-methylpyridine;

3-(3-Butylthio-1,2,5-thiadiazol-4-yl)-1,2,5,6-tetrahydro-1-methylpyridine;

3-(3-Methylthio-1,2,5-thiadiazol-4-yl)-1,2,5,6-tetrahydro-1-methylpyridine;

3-(3-Octylthio-1,2,5-thiadiazol-4-yl)-1,2,5,6-tetrahydro-1-methylpyridine;

3-(3-Ethylthio-1,2,5-thiadiazol-4-yl)-1,2,5,6-tetrahydro-1-methylpyridine;

3-(3-Pentylthio-1,2,5-thiadiazol-4-yl)-1,2,5,6-tetrahydro-1-methylpyridine;

3-(3-Hexylthio-1,2,5-thiadiazol-4-yl)-1,2,5,6-tetrahydro-1-methylpyridine;

3-(3-Hexylthio-1,2,5-thiadiazol-4-yl)-1,2,5,6-tetrahydro-1,6-dimethylpyridine;

3-(3-Pentylthio-1,2,5-thiadiazol-4-yl)-1,2,5,6-tetrahydro-1,6-dimethylpyridine;

3-(3-Butylthio-1,2,5-thiadiazol-4-yl)-1,2,5,6-tetrahydro-1,6-dimethylpyridine;

3-(3-Ethylthio-1,2,5-thiadiazol-4-yl)-1,2,5,6-tetrahydro-1,6-dimethylpyridine;

3-(3-(4-Pentynylthio)-1,2,5-thiadiazol-4-yl)-1,2,5,6-tetrahydro-1,6-dimethylpyridine;

3-(3-Hexylthio-1,2,5-thiadiazol-4-yl)-1,2,5,6-tetrahydro-1-ethylpyridine;

3-(3-Ethylthio-1,2,5-thiadiazol-4-yl)-1,2,5,6-tetrahydro-1-ethylpyridine;

3-(3-Ethylthio-1,2,5-thiadiazol-4-yl)-1,2,5,6-tetrahydropyridine;

3-(3-Propylthio-1,2,5-thiadiazol-4-yl)-1,2,5,6-tetrahydropyridine;

3-(3-Butylthio-1,2,5-thiadiazol-4-yl)-1,2,5,6-tetrahydropyridine;

3-(3-Pentylthio-1,2,5-thiadiazol-4-yl)-1,2,5,6-tetrahydropyridine;

3-(3-Hexylthio-1,2,5-thiadiazol-4-yl-1,2,5,6-tetrahydropyridine;

3-(3-(4-Pentynylthio)-1,2,5-thiadiazol-4-yl)-1,2,5,6-tetrahydropyridine;

3-(3-Isohexylthio-1,2,5-thiadiazol-4-yl)-1,2,5,6-tetrahydro-1-methylpyridine;

cis 3-(3-(3-Hexenylthio)-1,2,5-thiadiazol-4-yl)-1,2,5,6-tetrahydro-1-methylpyridine;

3-(3-(5-Hexenylthio)-1,2,5-thiadiazol-4-yl)-1,2,5,6-tetrahydro-1-methylpyridine;

3-(3-Cyclopentylthio-1,2,5-thiadiazol-4-yl)-1,2,5,6-tetrahydro-1-methylpyridine;

3-(3-(4-Pentynylthio)-1,2,5-thiadiazol-4-yl)-1,2,5,6-tetrahydro-1-methylpyridine;

3-(3-Heptylthio-1,2,5-thiadiazol-4-yl)-1,2,5,6-tetrahydro-1-methylpyridine;

3-(3-(7-Octenylthio)-1,2,5-thiadiazol-4-yl)-1,2,5,6-tetrahydro-1-methylpyridine;

3-(3-(3-Butenylthio)-1,2,5-thiadiazol-4-yl)-1,2,5,6-tetrahydro-1-methylpyridine;

3-(3-(4-Pentenylthio)-1,2,5-thiadiazol-4-yl)-1,2,5,6-tetrahydro-1-methylpyridine;

or a pharmaceutically acceptable salt thereof.

10. The method according to claim 1, wherein the compound is:

3-(3-(5-Cyanopentylthio)-1,2,5-thiadiazol-4-yl)-1,2,5,6-tetrahydro-1-methylpyridine;

3-(3-(3-Chloropropylthio)-1,2,5-thiadiazol-4-yl)-1,2,5,6-tetrahydro-1-methylpyridine;

3-(3-(3-Cyanopropylthio)-1,2,5-thiadiazol-4-yl)-1,2,5,6-tetrahydro-1-methylpyridine;

3-(3-(3-Phenylpropylthio)-1,2,5-thiadiazol-4-yl)-1,2,5,6-tetrahydro-1-methylpyridine;

3-(3-(2-Phenoxyethylthio)-1,2,5-thiadiazol-4-yl)-1,2,5,6-tetrahydro-1-methylpyridine;

3-(3-(4-Cyanobutylthio)-1,2,5-thiadiazol-4-yl)-1,2,5,6-tetrahydro-1-methylpyridine;

3-(3-(8-Hydroxyoctylthio)-1,2,5-thiadiazol-4-yl)-1,2,5,6-tetrahydro-1-methylpyridine;

3-(3-(4-Chlorobutylthio)-1,2,5-thiadiazol-4-yl)-1,2,5,6-tetrahydro-1-methylpyridine;

3-(3-(4,4-Bis-(4-fluorophenyl)-butylthio)-1,2,5-thiadiazol-4-yl)-1,2,5,6-tetrahydro-1-methylpyridine;

3-(3-(2-Phenylethylthio)-1,2,5-thiadiazol-4-yl)-1,2,5,6-tetrahydro-1-methylpyridine;

3-(3-(2-Benzoylethylthio)-1,2,5-thiadiazol-4-yl)-1,2,5,6-tetrahydro-1-methylpyridine;

3-(3-(4-Oxo-4-(4-fluorophenyl)-butylthio)-1,2,5-thiadiazol-4-yl)-1,2,5,6-tetrahydro-1-methylpyridine;

3-(3-Benzyloxycarbonylmethylthio-1,2,5-thiadiazol-4-yl)-1,2,5,6-tetrahydro-1-methylpyridine;

3-(3-(4,4,4-Trifluorobutylthio)-1,2,5-thiadiazol-4-yl)-1,2,5,6-tetrahydro-1-methylpyridine;

3-(3-(5,5,5-Trifluoropentylthio)-1,2,5-thiadiazol-4-yl)-1,2,5,6-tetrahydro-1-methylpyridine;

3-(3-(6,6,6-Trifluorohexylthio)-1,2,5-thiadiazol-4-yl)-1,2,5,6-tetrahydro-1-methylpyridine;

3-(3-Ethoxycarbonylpentylthio-1,2,5-thiadiazol-4-yl)-1,2,5,6-tetrahydro-1-methylpyridine;

3-(3-(4-Cyanobutylthio)-1,2,5-thiadiazol-4-yl)-1,2,5,6-tetrahydro-1,6-dimethylpyridine;

3-(3-(3-Phenylpropylthio)-1,2,5-thiadiazol-4-yl)-1,2,5,6-tetrahydro-1,6-dimethylpyridine;

3-(3-(2,2,2-Trifluoroethylthio)-1,2,5-thiadiazol-4-yl)-1,2,5,6-tetrahydropyridine;

3-(3-(2-Phenoxyethylthio)-1,2,5-thiadiazol-4-yl)-1,2,5,6-tetrahydropyridine;

3-(3-(2,2,2-Trifluoroethylthio)-1,2,5-thiadiazol-4-yl)-1,2,5,6-tetrahydro-1-methylpyridine;

3-(3-Ethoxycarbonylpropylthio-1,2,5-thiadiazol-4-yl)-1,2,5,6-tetrahydro-1-methylpyridine;

3-(3-(6-Hydroxyhexylthio)-1,2,5-thiadiazol-4-yl)-1,2,5,6-tetrahydro-1-methylpyridine;

3-(3-(1-Cyclopropylmethylthio)-1,2,5-thiadiazol-4-yl)-1,2,5,6-tetrahydro-1-methylpyridine;

3-(3-(1-Ethoxycarbonylpentylthio)-1,2,5-thiadiazol-4-yl)-1,2,5,6-tetrahydro-1-methylpyridine;

3-(3-(2-Methoxyethylthio)-1,2,5-thiadiazol-4-yl)-1,2,5,6-tetrahydro-1-methylpyridine;

3-(3-(2-(2-Ethoxymethoxy)-ethylthio)-1,2,5-thiadiazol-4-yl)-1,2,5,6-tetrahydro-1-methylpyridine;

3-(3-(2-Ethylbutylthio)-1,2,5-thiadiazol-4-yl)-1,2,5,6-tetrahydro-1-methylpyridine;

3-(3-Cyclohexylmethylthio-1,2,5-thiadiazol-4-yl)-1,2,5,6-tetrahydro-1-methylpyridine;

3-(3-(3,3,3-Trifluoropropylthio)-1,2,5-thiadiazol-4-yl)-1,2,5,6-tetrahydro-1-methylpyridine;

3-(3-(1-Oxo-1-phenylpropylthio-1,2,5-thiadiazol-4-yl)-1,2,5,6-tetrahydro-1-methylpyridine;

3-(3-(4-Phenylthiobutylthio)-1,2,5-thiadiazol-4-yl)-1,2,5,6-tetrahydro-1-methylpyridine;

3-(3-Cyanomethylthio-1,2,5-thiadiazol-4-yl)-1,2,5,6-tetrahydro-1-methylpyridine;

3-(3-(6-Chlorohexylthio)-1,2,5-thiadiazol-4-yl)-1,2,5,6-tetrahydro-1-methylpyridine;

3-(3-(5-Chloropentylthio)-1,2,5-thiadiazol-4-yl)-1,2,5,6-tetrahydro-1-methylpyridine;

3-(3-(3-Carboxypropylthio)-1,2,5-thiadiazol-4-yl)-1,2,5,6-tetrahydro-1-methylpyridine;

3-(3-(5-Carboxypentylthio)-1,2,5-thiadiazol-4-yl)-1,2,5,6-tetrahydro-1-methylpyridine;

3-(3-(5-Mercaptopentylthio)-1,2,5-thiadiazol-4-yl)-1,2,5,6-tetrahydro-1-methylpyridine;

3-(3-(6-Mercaptohexylthio)-1,2,5-thiadiazol-4-yl)-1,2,5,6-tetrahydro-1-methylpyridine;

3-(3-(4-Mercaptobutylthio)-1,2,5-thiadiazol-4-yl)-1,2,5,6-tetrahydro-1-methylpyridine; or a pharmaceutically acceptable salt thereof.

11. The method according to claim 1, wherein the compound is:

3-(3-(4-Cyanobenzylthio)-1,2,5-thiadiazol-4-yl)-1,2,5,6-tetrahydro-1-methylpyridine;

3-(3-(4-Bromobenzylthio)-1,2,5-thiadiazol-4-yl)-1,2,5,6-tetrahydro-1-methylpyridine;

3-(3-(4-Methylbenzylthio)-1,2,5-thiadiazol-4-yl)-1,2,5,6-tetrahydro-1-methylpyridine;

3-(3-Benzylthio-1,2,5-thiadiazol-4-yl)-1,2,5,6-tetrahydro-1-methylpyridine;

3-(3-(4-Cyanobenzylthio)-1,2,5-thiadiazol-4-yl)-1,2,5,6-tetrahydro-1,6-dimethylpyridine; or a pharmaceutically acceptable salt thereof.

12. The method according to claim 1, wherein the compound is:

3-(3-Chloro-1,2,5-thiadiazol-4-yl)-1,2,5,6-tetrahydro-1-methylpyridine;

3-(3-Chloro-1,2,5-thiadiazol-4-yl)-1,2,5,6-tetrahydropyridine;

3-(3-Chloro-1,2,5-thiadiazol-4-yl)-1-ethyl-1,2,5,6-tetrahydropyridine;

3-(1,2,5-Thiadiazol-3-yl)-1,2,5,6-tetrahydro-1-methylpyridine;

3-(3-Hexylamino-1,2,5-thiadiazol-4-yl)-1,2,5,6-tetrahydro-1-methylpyridine; or a pharmaceutically acceptable salt thereof.

13. The method according to claim 1, wherein the compound is:

3-(3-Pentyl-1,2,5-thiadiazol-4-yl)-1,2,5,6-tetrahydro-1-methylpyridine;

3-(3-Heptyl-1,2,5-thiadiazol-4-yl)-1,2,5,6-tetrahydro-1-methylpyridine;

3-(3-(5-Hexenyl)-1,2,5-thiadiazol-4-yl)-1,2,5,6-tetrahydro-1-methylpyridine;

3-(3-Octyl-1,2,5-thiadiazol-4-yl)-1,2,5,6-tetrahydro-1-methylpyridine;

3-(3-Isobutyl-1,2,5-thiadiazol-4-yl)-1,2,5,6-tetrahydro-1-methylpyridine;

3-(3 -Cyclopropylmethyl-1,2,5-thiadiazol-4-yl)-1,2,5,6-tetrahydro-1-methylpyridine;

3-(3-Propyl-1,2,5-thiadiazol-4-yl)-1,2,5,6-tetrahydro-1-methylpyridine;

1,2,5,6-Tetrahydro-3-(3-(5-oxohexyl)-1,2,5-thiadiazol-4-yl)-1-methylpyridine;

or a pharmaceutically acceptable salt thereof.

14. The method according to claim 1, wherein the compound is:

3-(3-Methylsulfonyl-1,2,5-thiadiazol-4-yl)-1,2,5,6-tetrahydro-1-methylpyridine;

3-(3-(4-Methylenecyclohexylmethyl)-1,2,5-thiadiazol-4-yl)-1,2,5,6-tetrahydro-1-methylpyridine; or a pharmaceutically acceptable salt thereof.

15. The method according to claim 1, wherein the compound is:

3-(3-Amino-1,2,5-oxadiazol-4-yl)-1,2,5,6-tetrahydro-1-methylpyridine;

3-(3-Acetylamino-1,2,5-oxadiazol-4-yl)-1,2,5,6-tetrahydro-1-methylpyridine;

3-(3-Chloro-1,2,5-oxadiazol-4-yl)-1,2,5,6-tetrahydro-1-methylpyridine;

3-(1,2,5-Oxadiazol-3-yl)-1,2,5,6-tetrahydro-1-methylpyridine; or a pharmaceutically acceptable salt thereof.

16. The method according to claim 1, wherein the compound is:

3-(3-Hexyloxy-1,2,5-oxadiazol-4-yl)-1,2,5,6-tetrahydro-1-methylpyridine;

3-(3-Butyloxy-1,2,5-oxadiazol-4-yl)-1,2,5,6-tetrahydro-1-methylpyridine;

3-(3-(3-Hexynyloxy)-1,2,5-oxadiazol-4-yl)-1,2,5,6-tetrahydro-1-methylpyridine;

or a pharmaceutically acceptable salt thereof.

17. The method according to claim 1, wherein the compound is:

3-(3-(3-Phenylpropylthio)-1,2,5-oxadiazol-4-yl)-1,2,5,6-tetrahydro-1-methylpyridine;

3-(3-(2-Phenoxyethylthio)-1,2,5-oxadiazol-4-yl)-1,2,5,6-tetrahydro-1-methylpyridine;

3-(3-Pentylthio-1,2,5-oxadiazol-4-yl)-1,2,5,6-tetrahydro-1-methylpyridine;

3-(3-Hexylthio-1,2,5-oxadiazol-4-yl)-1,2,5,6-tetrahydro-1-methylpyridine;

3-(3-(4-Pentynylthio)-1,2,5-oxadiazol-4-yl)-1,2,5,6-tetrahydro-1-methylpyridine;

or a pharmaceutically acceptable salt thereof.

* * * * *